United States Patent
Xu

(10) Patent No.: US 11,427,556 B2
(45) Date of Patent: Aug. 30, 2022

(54) UREA DERIVATIVES AS INHIBITORS OF ASK1

(71) Applicant: Hepagene Therapeutics (HK) Limited, Wan Chai (HK)

(72) Inventor: Xiaodong Xu, Doylestown, PA (US)

(73) Assignee: Hepagene Therapeutics (HK) Limited, Wan Chai (HK)

( * ) Notice: Subject to any disclaimer, the term of this patent is extended or adjusted under 35 U.S.C. 154(b) by 0 days.

(21) Appl. No.: 16/761,674

(22) PCT Filed: Nov. 9, 2018

(86) PCT No.: PCT/US2018/060161
§ 371 (c)(1),
(2) Date: May 5, 2020

(87) PCT Pub. No.: WO2019/099307
PCT Pub. Date: May 23, 2019

(65) Prior Publication Data
US 2020/0339530 A1    Oct. 29, 2020

Related U.S. Application Data

(60) Provisional application No. 62/587,613, filed on Nov. 17, 2017.

(51) Int. Cl.
| | |
|---|---|
| *C07D 401/04* | (2006.01) |
| *A61P 1/16* | (2006.01) |
| *C07D 401/14* | (2006.01) |
| *C07D 413/14* | (2006.01) |
| *C07D 417/14* | (2006.01) |
| *C07D 451/02* | (2006.01) |
| *C07D 491/08* | (2006.01) |

(52) U.S. Cl.
CPC .............. *C07D 401/04* (2013.01); *A61P 1/16* (2018.01); *C07D 401/14* (2013.01); *C07D 413/14* (2013.01); *C07D 417/14* (2013.01); *C07D 451/02* (2013.01); *C07D 491/08* (2013.01)

(58) Field of Classification Search
None
See application file for complete search history.

(56) References Cited

U.S. PATENT DOCUMENTS

2011/0009410 A1    1/2011    Corkey et al.

FOREIGN PATENT DOCUMENTS

| JP | WO 98/24785 | * 12/1997 | .......... C07D 403/12 |
|---|---|---|---|
| WO | WO-03/040131 A1 | 5/2003 | |
| WO | WO-2005/012254 A1 | 2/2005 | |
| WO | WO-2005/048932 A2 | 6/2005 | |
| WO | WO-2006/049941 A2 | 5/2006 | |
| WO | WO-2006/055734 A2 | 5/2006 | |
| WO | WO-2007/120600 A2 | 10/2007 | |
| WO | WO-2015/039333 A1 | 3/2015 | |
| WO | WO-2015/039334 | 3/2015 | |
| WO | WO-2018/157857 A1 | 9/2018 | |

OTHER PUBLICATIONS

International Preliminary Report on Patentability on PCT/US2018/060161 dated May 28, 2020 (10 pages).
Database extract—compound with Registry No. 727673-41-8.
Database extract—compound with Registry No. 897545-19-6.
Examination Report on EP 18812480.4 dated Feb. 11, 2022 (6 pages).
Gradler, Ulrich et al. "Fragment-based discovery of focal adhesion kinase inhibitors," Bioorg. & , Med. Chem. Letters, 23(19):5401-5409 (2013).
International Search Report and Written Opinion on Appl. No. PCT/US2018/060161 dated Jan. 23, 2019.
Teegarden, Bradley R. et al. "Discovery of 1-[3-{4-Bromo-2-methyl-2-H-pyrazol-3-yl)-4-methoxyphenyl]-3-(2,4-difluorophenyl)urea (Nelotanserin) and Related 5-Hydroxytryptamine 2A Inverse Agonists for the Treatment of Insomnia," J. of Med. Chem., 53(5):1923-1936 (2010).

* cited by examiner

*Primary Examiner* — Samantha L Shterengarts
(74) *Attorney, Agent, or Firm* — Foley & Lardner LLP

(57) ABSTRACT

The present technology is directed to compounds, compositions, and methods related to inhibition of ASK1. In particular, the present compounds (e.g., compounds of Formula I as defined herein) and compositions may be used to treat ASK1-mediated disorders and conditions, including, e.g., fibrotic diseases and acute and chronic liver diseases, among others.

18 Claims, No Drawings

UREA DERIVATIVES AS INHIBITORS OF ASK1

CROSS-REFERENCE TO RELATED APPLICATIONS

This application is a U.S. national stage application under 35 U.S.C. § 371 of International Application No. PCT/US2018/060161, filed Nov. 9, 2018, which claims the benefit of and priority to U.S. Provisional Patent Application No. 62/587,613, filed Nov. 17, 2017, each of which is hereby incorporated by reference in its entirety for any and all purposes.

FIELD

The present technology is directed to compounds, compositions, and methods related to inhibition of apoptosis signal regulating kinase 1 (ASK1). In particular, the present compounds and compositions may be used to treat ASK-mediated disorders and conditions, including, e.g., fibrotic diseases, acute and chronic liver diseases and kidney diseases.

BACKGROUND

ASK1 is a member of the mitogen-activated protein kinase family and activates c-Jun N-terminal kinase (JNK) and p38 mitogen-activated protein kinases. ASK1 contributes to the regulation of cell death, cytokine responses, cell differentiation and immune regulation, and has been found to be involved in fibrosis, non-alcoholic steatohepatitis (NASH), cancer, diabetes, cardiovascular and neurodegenerative diseases. Therefore, inhibitors of ASK1 are important compounds for pharmaceutical application.

SUMMARY

In one aspect, the present technology provides a compound according to Formula I

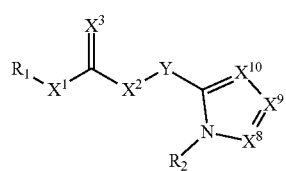

(I)

and pharmaceutically acceptable salts thereof;
wherein
$X^1$ is O or $NR^3$;
$X^2$ is O or $NR^4$;
$X^3$ is O, S, NH, or N—$OR^5$;
$X^8$, $X^9$, and $X^{10}$ are independently CH or N;
Y is a substituted or unsubstituted phenyl or 5- or 6-member heteroaryl group;
$R^1$ is a substituted or unsubstituted aryl or heteroaryl group;
$R^2$ is substituted or unsubstituted alkyl or cycloalkyl group;
$R^3$ and $R^4$ are independently H or a substituted or unsubstituted alkyl or cycloalkyl group, or $R^3$ and $R^4$ together are a $C_2$-$C_3$ alkylene or alkenylene group or a phenylene group;

$R^5$ is H or substituted or unsubstituted alkyl or cycloalkyl group.

In any embodiments, Y is a substituted or unsubstituted pyridinyl group.

In any embodiments of compounds of Formula I, there is provided a compound of Formula IA:

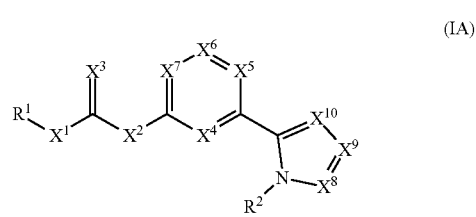

(IA)

and pharmaceutically acceptable salts thereof,
wherein
$X^4$ is $CR^6$ or N;
$X^5$ is $CR^7$ or N;
$X^6$ is $CR^8$ or N;
$X^7$ is $CR^9$ or N;
$R^6$, $R^7$, R, and $R^9$ are independently H, halo, OH, $NO_2$, CN, COOH, C(O)O(alkyl), C(O)O(aralkyl), C(O)O(alkenyl), C(O)(alkyl), $NH_2$, C(O)$NH_2$, NH(alkyl), N(alkyl)$_2$, thioalkyl, haloalkyl, alkoxy, haloalkoxy, hydroxyalkyl, or a substituted or unsubstituted alkyl, cycloalkyl group; and the remaining variables ($X^1$, $X^2$, $X^3$, $X^8$, $X^9$, $X^{10}$, $R^1$, $R^2$) are as defined for Formula I.

In a related aspect, a composition is provided that includes the compound of any one of the compounds disclosed herein, and a pharmaceutically acceptable carrier.

In another aspect, a pharmaceutical composition is provided, the pharmaceutical composition including an effective amount of any one of the compounds disclosed herein for treating an ASK1-mediated disorder or condition.

In another aspect, a method is provided that includes administering an effective amount of any one of the compounds disclosed herein, or administering a pharmaceutical composition including an effective amount of one of the compounds disclosed herein, to a subject suffering from an ASK1-mediated disorder or condition.

In another aspect, a method is provided that includes inhibiting ASK1 by contacting ASK1 with an effective amount of any one of the compounds disclosed herein.

DETAILED DESCRIPTION

In various aspects, the present technology provides compounds and methods for inhibition ASK1 and the treatment of ASK1-mediated disorders and conditions. The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In any embodiments, a substituted group is substituted with 1, 2, 3, 4, 5, or 6 substituents. Examples of substituent groups include: halogens (i.e., F, Cl, Br, and I); hydroxyls; alkoxy, haloalkoxy, alkenoxy, aryloxy, aralkyloxy, heterocyclyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; amines; ureas; amidines; guanidines; enamines; imides; isocyanates; isothiocyanates; cyanates; thiocyanates; imines; nitro groups; nitriles (e.g., CN); and the like.

Substituted ring groups such as substituted cycloalkyl, cycloalkylalkyl, aryl, heterocyclyl and heteroaryl groups also include rings and ring systems in which a bond to a hydrogen atom is replaced with a bond to a carbon atom. Therefore, substituted cycloalkyl, cycloalkylalkyl, aryl, heterocyclyl and heteroaryl groups may also be substituted with substituted or unsubstituted alkyl, cycloalkyl, cycloalkylalkyl, alkenyl, alkynyl, aryl, heterocyclyl, or heteroaryl groups as defined below.

Alkyl groups include straight chain and branched chain alkyl groups having from 1 to 12 carbon atoms, and typically from 1 to 10 carbons or, In any embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, In any embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In any embodiments, the cycloalkyl group has 3 to 8 ring members, whereas in other embodiments the number of ring carbon atoms range from 3 to 5, 3 to 6, or 3 to 7. Bi— and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In any embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, In any embodiments, from 2 to 8, 2 to 6, or 2 to 4 carbon atoms. In any embodiments, the alkenyl group has one, two, or three carbon-carbon double bonds. Examples include, but are not limited to vinyl, allyl, —CH=CH(CH$_3$), —CH=C (CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, In any embodiments, from 2 to 8, 2 to 6, or 2 to 4 carbon atoms. In any embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons having 6-14 carbons and that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In any embodiments, aryl groups contain 6 to 12 or even 6-10 carbon atoms in the ring portions of the groups. In any embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups of the present technology contain 7 to 16 carbon atoms, or In any embodiments, 7 to 14 carbon atoms, or even 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic carbon-containing ring compounds containing 3 or more ring members, of which one or more is a heteroatom such as, but not limited to, N, O, and S. In any embodiments, the heterocyclyl group contains 1, 2, 3 or 4 heteroatoms. In any embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo [1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, oxadiazolonyl (including 1,2, 4-oxazol-5(4H)-one-3-yl), isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic carbon-containing ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups; divalent aryl groups are arylene groups;

divalent heteroaryl groups are heteroarylene groups; and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In any embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In any embodiments, the amine is NH$_2$, alkylamino, dialkylamino, arylamino, or alkylarylamino. In any other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In any embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In any embodiments the sulfide is an alkylthio group, —S-alkyl.

With respect to substituents, the term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In any embodiments, the halogen is fluorine. In any embodiments, the halogen is chlorine or bromine.

The term "hydroxyl" as used herein can refer to —OH or its ionized form, —O—. A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The phrase "selectively inhibits" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum refers to the compounds acting through a specific mechanism of action, resulting in fewer off-target effects because the compounds target a particular receptor over other receptors, such as an ASK1 over other kinases. This phrase may further be modified as discussed herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, guanidines may exhibit the following isomeric forms in protic organic solution, also referred to as tautomers of each other:

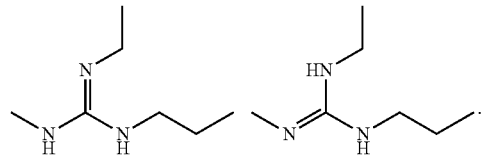

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

In one aspect, the present technology provides urea derivatives (including substituted ureas, thioureas, urethanes, guanidines, etc.) that include pyridines and other heterocycles that inhibit ASK1 and intermediates for making such compounds. The compounds include, but are not limited to compounds of Formulas I, IA, IB, IC, and ID as described herein.

In some aspects or embodiments of compounds of the present technology, compounds of Formula I are provided:

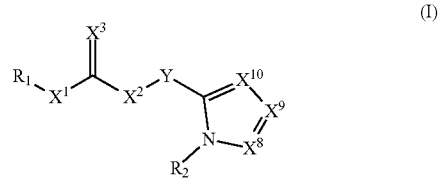

(I)

and pharmaceutically acceptable salts thereof;

wherein
X$^1$ is O or NR$^{3-}$;
X$^2$ is O or NR$^4$;
X$^3$ is O, S, NH, or N—OR$^5$;
X$^8$, X$^9$, and X$^{10}$ are independently CH or N;
Y is a substituted or unsubstituted phenyl group or a 5- or 6-member heteroaryl group;
R$^1$ is a substituted or unsubstituted aryl or heteroaryl group;
R$^2$ is substituted or unsubstituted alkyl or cycloalkyl group; and
R$^3$ and R$^4$ are independently H or a substituted or unsubstituted alkyl or cycloalkyl group, or R$^3$ and R$^4$ together are a C$_2$-C$_3$ alkylene or alkenylene group or a phenylene group.

In any embodiments of compounds of Formula I, Y is a substituted or unsubstituted 5-member heteroaryl group. In any other embodiments, Y is a substituted or unsubstituted phenyl or 6-member heteroaryl group. In any embodiments of compounds of Formula I, Y is a substituted or unsubstituted pyridinyl group. In others, Y is an unsubstituted pyridinyl group.

In any embodiments of compounds of Formula I, the compound has Formula IA:

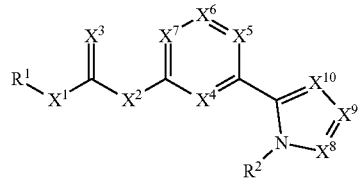

(IA)

or pharmaceutically acceptable salts thereof,
wherein
X$^4$ is CR$^6$ or N;
X$^5$ is CR$^7$ or N;
X$^6$ is CR$^8$ or N;
X$^7$ is CR$^9$ or N;
R$^6$, R$^7$, R, and R$^9$ are independently H, halo, OH, NO$_2$, CN, COOH, C(O)O(alkyl), C(O)O(aralkyl), C(O)O(alkenyl), C(O)(alkyl), NH$_2$, C(O)NH$_2$, NH(alkyl), N(alkyl)$_2$, thioalkyl, haloalkyl, alkoxy, haloalkoxy, hydroxyalkyl, or a substituted or unsubstituted alkyl, cycloalkyl group; and the remaining variables (X$^1$, X$^2$, X$^3$, X$^8$, X$^9$, X$^{10}$, R$^1$, R$^2$) are as defined for Formula I.

In any embodiments of the present compounds, X$^1$ may be NR$^3$. In others, X$^1$ may be O. In others X$^2$ may be NR$^4$. In some X$^2$ may be O. In any embodiments, X$^3$ may be O. In others X$^3$ may be S. In still others it may be NH or NOR$^5$. In any embodiments, X$^1$ may be NR$^3$, X$^2$ may be NR$^4$, X$^3$ may be O, and the compound is a urea of Formula IB:

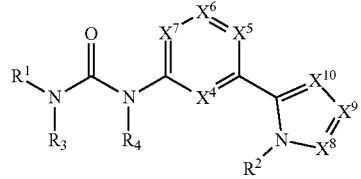

(IB)

or a pharmaceutically acceptable salt thereof.

In any embodiments of the present compounds, the urea derivative includes a heterocycle or phenyl group. For example, In any embodiments of compounds of Formula I, X$^4$ may be N. In others, X$^4$ may be CR$^6$. In some such embodiments, R$^6$ is H or an unsubstituted C$_1$-C$_6$ alkyl group such a methyl. In any embodiments, X$^5$ may be N. In others, X$^5$ may be CR$^7$. In some such embodiments, R$^7$ is H or an unsubstituted C$_1$-C$_6$ alkyl group such a methyl. In any embodiments, X$^6$ may be N. In any other embodiments, X$^6$ may be CR$^8$. In some such embodiments, R$^8$ may be H or an unsubstituted C$_1$-C$_6$ alkyl group such a methyl. In any embodiments X$^7$ may be N. In others, X$^7$ may be CR$^9$. In some such embodiments, R$^9$ may be H or an unsubstituted C$_1$-C$_6$ alkyl group such a methyl. In certain embodiments, X$^4$ is N, X$^5$ is CR$^7$, X$^6$ is CR$^8$, and X$^7$ is CR$^9$. In some such embodiments, R$^7$, R$^8$ and R$^9$ are all H and the compound is a compound of Formula IC:

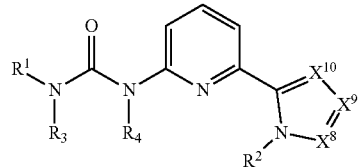

(IC)

or a pharmaceutically acceptable salt thereof.

In any embodiments of the present compounds, X$^8$ may be N. In others, X$^8$ may be CH. In any embodiments, X$^9$ may be N. In others, X$^9$ may be CH. In any embodiments, X$^{10}$ may be N. In others, X$^{10}$ may be CH. In certain embodiments, X$^8$ is CH, X$^9$ is N, and X$^{10}$ is N, and the compound has the Formula ID:

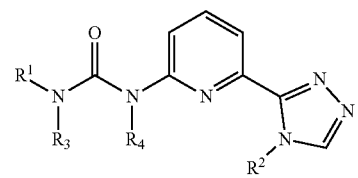

(ID)

or a pharmaceutically acceptable salt thereof.

In any embodiments, the compound may be a compound of Formula IE, IF, or IG:

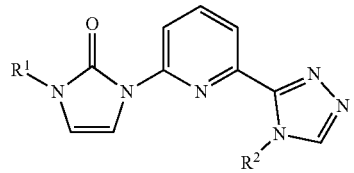

(IE)

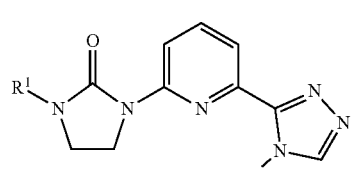

(IF)

-continued

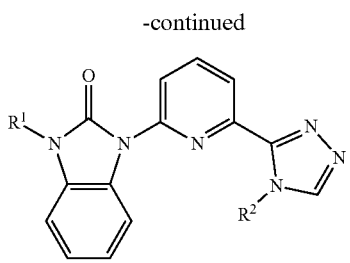

(IG)

or pharmaceutically acceptable salts thereof. $R^1$ and $R^2$ may be defined as in any embodiments disclosed herein.

The present compounds (including but not limited to any of the compounds of Formulae I, IA, IB, IC, and ID) may include a variety of $R^1$ groups as defined herein. In any embodiments, $R^1$ may be a substituted or unsubstituted phenyl, pyridinyl, pyrazinyl, pyrimidinyl, isoquinolinyl, quinolinyl, oxazolyl, benzoxazolyl, or benzthiazolyl group. In any embodiments, $R^1$ is a phenyl, pyridinyl, pyrazinyl, pyrimidinyl, quinolinyl, isoquinolinyl, or oxazolyl group, optionally substituted with one or more substituents. In any embodiments, $R^1$ is phenyl or pyridinyl, optionally substituted with one or more substituents. In any embodiments, the foregoing substituents may be selected from the group consisting of F, Cl, Br, I, OH, CN, COOH, C(O)O(unsubstituted alkyl), C(O)O(aralkyl), C(O)O(alkenyl), C(O)NH(cycloalkyl), C(O)NH(aryl), C(O)NH(pyridinyl), C(O)(aryl), C(O)(unsubstituted alkyl), C(O)(arlkyl), C(O)(alkenyl), C(O)(piperidinyl), C(O)(morpholinyl), C(O)(piperazinyl), C(O)(pyrrolidinyl), C(O)(azepanyl), C(O)(quinolyl), C(O)(tetrahydroquinolinyl), C(O)(decahydroquinolinyl), C(O)(isoquinolinyl), C(O)(tetrahydroisoquinolinyl), C(O)(3-azaspiro[5,5]-undecanyl), C(O)(8-azabicyclo[3.2.1]octanyl), NH$_2$, NO$_2$, C(O)NH$_2$, NH(alkyl), N(alkyl)$_2$, SO$_2$(alkyl), SO$_2$NH(phenyl), SO$_2$NH$_2$, NHSO$_2$(aryl), SO$_2$(piperidinyl), SO$_2$(morpholinyl), alkyl, thioalkyl, haloalkyl, alkoxy, aralkoxy, aralkylthio, haloalkoxy, hydroxyalkyl, cycloalkyl, phenyl, pyrrolidinyl, morpholinyl, 3-oxa-8-azabicyclo[3.2.1]octanyl, piperidinyl, piperazinyl, imidazolyl, triazolyl, tetrahydropyran, and pyridinyl, wherein the alkyl groups are unsubstituted except as indicated, and wherein the phenyl, pyridinyl, piperidinyl, piperazinyl, imidazolyl, triazolyl, and morpholinyl substituents are themselves optionally substituted with one or more secondary substituents selected from halo, OH, oxo, unsubstituted alkyl, hydroxyalkyl, cycloalkyl, phenyl, SO$_2$(alkyl), C(O)(alkyl), and morpholinyl. In any embodiments, the foregoing substituents may be selected from the group consisting of F, Cl, Br, I, OH, CN, COOH, C(O)O(alkyl), C(O)O(aralkyl), C(O)O(alkenyl), C(O)(alkyl), C(O)(arlkyl), C(O)(alkenyl), NH$_2$, C(O)NH$_2$, NH(alkyl), N(alkyl)$_2$, thioalkyl, haloalkyl, alkoxy, haloalkoxy, hydroxyalkyl, cycloalkyl, phenyl, pyrrolidinyl, morpholinyl, piperidinyl, piperazinyl, imidazolyl, and pyridinyl, wherein the alkyl groups are unsubstituted except as indicated. In some such embodiments the alkyl groups are $C_1$-$C_6$ alkyl groups. In any embodiments, the foregoing substituents may be selected from the group consisting of F, Cl, Br, I, OH, CN, COOH, C(O)O(unsubstituted alkyl), C(O)NH(cycloalkyl), C(O)NH(aryl), C(O)NH(pyridinyl), C(O)(aryl), C(O)(piperidinyl), C(O)(morpholinyl), C(O)(piperazinyl), C(O)(pyrrolidinyl), C(O)(azepanyl), C(O)(quinolyl), C(O)(tetrahydroquinolinyl), C(O)(decahydroquinolinyl), C(O)(isoquinolinyl), C(O)(tetrahydroisoquinolinyl), C(O)(3-azaspiro[5,5]-undecanyl), C(O)(8-azabicyclo[3.2.1]octanyl), NH$_2$, NO$_2$, C(O)NH$_2$, NH(alkyl), N(alkyl)$_2$, SO$_2$(alkyl), SO$_2$NH(phenyl), SO$_2$NH$_2$, NHSO$_2$(aryl), SO$_2$(piperidinyl), SO$_2$(morpholinyl), alkyl, haloalkyl, alkoxy, aralkoxy, aralkylthio, hydroxyalkyl, cycloalkyl, phenyl, pyrrolidinyl, morpholinyl, 3-oxa-8-azabicyclo[3.2.1]octanyl, piperidinyl, piperazinyl, imidazolyl, triazolyl, tetrahydropyran, and pyridinyl, wherein the alkyl groups are unsubstituted except as indicated, and wherein the phenyl, pyridinyl, piperidinyl, piperazinyl, imidazolyl, triazolyl, and morpholinyl groups are themselves optionally substituted with one or more secondary substituents selected from F, OH, oxo, unsubstituted alkyl, hydroxyalkyl, cyclopropyl, phenyl, SO$_2$(unsubstituted alkyl), C(O)(unsubstituted alkyl), and morpholinyl.

In any embodiments of the present compounds, $R^2$ may be a $C_1$-$C_6$ alkyl, $C_3$-$C_6$ cycloalkyl or $C_4$-$C_8$ cycloalkylalkyl group optionally substituted with one or more substituents selected from the group consisting of halo, OH, NH$_2$, OCH$_3$, OP(O)(OH)$_2$, OC(O)(substituted or unsubstituted alkyl), and OP(O)(OPh)NHC(unsubstituted alkyl)C(O)(unsubstituted alkyl). In any embodiments, the $C_1$-$C_6$ akyl, $C_3$-$C_6$ cycloalkyl or $C_4$-$C_8$ cycloalkylalkyl group may be substituted with one, two or three substituents.

In any embodiments, $R^3$ and $R^4$ are independently H or a substituted or unsubstituted alkyl or cycloalkyl group. In any embodiments $R^3$ and $R^4$ are independently H or a substituted or unsubstituted $C_1$-$C_6$ alkyl or $C_3$-$C_6$ cycloalkyl group. In any embodiments, $R^3$ and $R^4$ are both H. In certain embodiments, $R^3$ and $R^4$ together are a $C_2$-$C_3$ alkylene or alkenylene group or a phenylene group.

In any embodiments, $R^5$, $R^6$, $R^7$, $R^8$ and $R^9$ are independently H or a substituted or unsubstituted alkyl or cycloalkyl group. In others, R, $R^6$, $R^7$, $R^8$ and $R^9$ are independently H, or substituted or unsubstituted $C_1$-$C_6$ alkyl or $C_3$-$C_6$ cycloalkyl. In still others, R, $R^6$, $R^7$, R and $R^9$ are independently H, methyl, ethyl, n-propyl, i-propyl, cyclopropyl, n-butyl, i-butyl, s-butyl, or t-butyl.

In an aspect of the present technology, a composition is provided that includes any one of the aspects and embodiments of compounds disclosed herein (e.g., compounds of Formulas (I, IA, IB, IC, and ID) and a pharmaceutically acceptable carrier. In a related aspect, a pharmaceutical composition is provided which includes an effective amount of the compound of any one of the aspects and embodiments of compounds of Formulas I and IA-ID for treating an ASK1-mediated disorder or condition. The ASK1-mediated disorder or condition may be fibrotic diseases including liver fibrosis, lung fibrosis, kidney fibrosis and idiopathic pulmonary fibrosis (IPF), acute and chronic liver diseases including non-alcoholic steatohepatitis (NASH), kidney diseases, autoimmune disorders, inflammatory diseases, cardiovascular diseases, diabetes, diabetic nephropathy, cardio-renal diseases, and neurodegenerative diseases. For example, the disorder or condition may be liver fibrosis or NASH.

In a further related aspect, a method is provided that includes administering an effective amount of a compound of any one of the aspects and embodiments of the present compounds or administering a pharmaceutical composition comprising an effective amount of a compound of any one of the aspects and embodiments of the present compounds to a subject suffering from an ASK1-mediated disorder or condition. The ASK-mediated disorder or condition may be The ASK1-mediated disorder or condition may be fibrotic diseases including liver fibrosis, lung fibrosis, kidney fibrosis and IPF, acute and chronic liver diseases including NASH, kidney diseases, autoimmune disorders, inflammatory diseases, cardiovascular diseases, diabetes, diabetic nephropathy, cardio-renal diseases, and neurodegenerative diseases. For example, the disorder or condition may be liver fibrosis or NASH.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of liver fibrosis or NASH. Another example of an effective amount includes amounts or dosages that are capable of ameliorating or reducing symptoms associated with liver fibrosis or NASH. The effective amount of the compound may selectively inhibit ASK1. As used herein, a "subject" or "patient" is a mammal, such as a cat, dog, rodent or primate. Typically the subject is a human, and, preferably, a human suffering from or suspected of suffering from an ASK1-mediated disorder or condition. The term "subject" and "patient" can be used interchangeably.

In still another aspect, the present technology provides methods of inhibiting ASK1 by contacting ASK1 with an effective amount of any compound as described herein, including but not limited to a compound of Formulas I, IA, IB, IC, and ID. In any embodiments, the method includes inhibiting ASK1 in vitro.

Thus, the instant present technology provides pharmaceutical compositions and medicaments comprising any of the compounds disclosed herein (e.g., compounds of Formulas I and IA-ID) and a pharmaceutically acceptable carrier or one or more excipients or fillers. The compositions may be used in the methods and treatments described herein. Such compositions and medicaments include a therapeutically effective amount of any compound as described herein, including but not limited to a compound of Formulas I, IA, IB, IC, and ID. The pharmaceutical composition may be packaged in unit dosage form.

The pharmaceutical compositions and medicaments may be prepared by mixing one or more compounds of the present technology, and/or pharmaceutically acceptable salts thereof, with pharmaceutically acceptable carriers, excipients, binders, diluents or the like to prevent and treat disorders and conditions associated with or mediated by ASK1. The compounds and compositions described herein may be used to prepare formulations and medicaments that prevent or treat a variety of disorders and conditions, including but not limited to fibrotic diseases including liver fibrosis, lung fibrosis, kidney fibrosis and IPF, acute and chronic liver diseases including NASH, kidney diseases, autoimmune disorders, inflammatory diseases, cardiovascular diseases, diabetes, diabetic nephropathy, cardio-renal diseases, and neurodegenerative diseases. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant)

aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until for example, (for metabolic syndrome and/or obesity) the elevated plasma or elevated white blood cell count or hepatic cholesterol or triglycerides or progression of the disease state is reduced or stopped. For metabolic syndrome and/or obesity, the progression of the disease state can be assessed using in vivo imaging, as described, or by taking a tissue sample from a patient and observing the target of interest therein.

The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

Effectiveness of the compositions and methods of the present technology may also be demonstrated by a decrease in the symptoms of hyperlipidemia, such as, for example, a decrease in triglycerides in the blood stream. Effectiveness of the compositions and methods of the present technology may also be demonstrated by a decrease in the signs and symptoms of liver disease, hyperlipidemia, hypercholesteremia, obesity, metabolic syndrome, cardiovascular disease, gastrointestinal disease, atherosclerosis, or renal disease.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The compounds of the present technology can also be administered to a patient along with other conventional therapeutic agents that may be useful in the treatment of liver disease, hyperlipidemia, hypercholesteremia, obesity, metabolic syndrome, cardiovascular disease, gastrointestinal disease, atherosclerosis, or renal disease. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially be effective for the treatment of liver disease, hyperlipidemia, hypercholesteremia, obesity, metabolic syndrome, cardiovascular disease, gastrointestinal disease, atherosclerosis, or renal disease.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1 \times 10^{-4}$ g/kg to 1 g/kg, preferably, $1 \times 10^{-3}$ g/kg to 1.0 g/kg. Dosage of a compound of the present technology can also vary from 0.01 mg/kg to 100 mg/kg or, preferably, from 0.1 mg/kg to 10 mg/kg.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes.

Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

List of Abbreviations

ACN acetonitrile
AcOH acetic acid
Ad$_2$PBu butyldi-1-adamantylphosphine
t-Bu tert-butyl
CDI 1,1'-carbonyldiimidazole
DCM dichloromethane
DIAD diisopropyl azodicarboxylate
DMF dimethylformamide
DMA dimethylacetamide
DMAP 4-dimethylaminopyridine
DMP tert-2,2-dimethoxypropane
DMSO dimethyl sulfoxide
EDC 3-(ethyliminomethyleneamino)-N,N-dimethylpropan-1-amine
Et ethyl
HATU (1-[bis(dimethylamino)methylene]-1H-1,2,3-triazolo[4,5-b] pyridinium 3-oxid hexafluorophosphate)
LAH lithium aluminum hydride
Me methyl
MeCN acetonitrile
NCS N-chlorosuccinimide
PCC pyridinium chlorochromate
Pd$_2$(dba)$_3$ tris(dibenzylideneacetone)dipalladium
Pd(dppf)Cl$_2$ [1,1'-bis(diphenylphosphino)ferrocene]palladium(II) dichloride
PE petroleum ether
Ph phenyl
Py pyridine
Ruphos 2-dicyclohexylphosphino-2',6'-diisopropoxy-1,1'-biphenyl
STAB Sodium triacetoxyborohydride
TEA triethylamine
TFA trifluoroacetic acid
TFAA trifluoroacetic anhydride
THF tetrahydrofuran
TLC thin layer chromatography
TMS trimethylsilyl
TsOH p-toluenesulfonic acid
Xantphos 4,5-bis(diphenylphosphino)-9,9-dimethylxanthene Example 1: Synthesis of Compound I-001

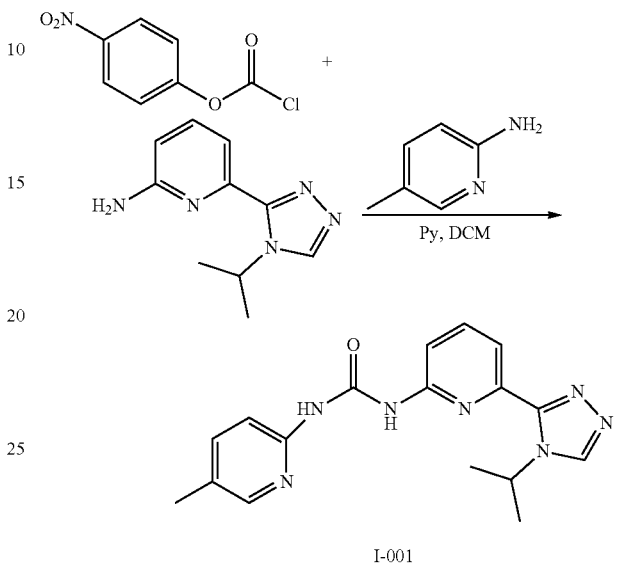

I-001

1-(6-(4-Isopropyl-4H-1,2,4-triazol-3-yl) pyridin-2-yl)-3-(5-methylpyridin-2-yl) urea (Compound I-001)

To a solution of 4-nitrophenyl chloroformate (201 mg, 1.0 mmol) in dichloromethane (4 mL) was added pyridine (80 mg, 1.0 mmol). After the mixture was stirred for a few min at 0° C., then a solution of 6-[4-(propan-2-yl)-4H-1,2,4-triazol-3-yl]pyridin-2-amine (203 mg, 1.0 mmol) in DCM (1 mL) was added dropwise. The mixture was stirred overnight at room temperature before a solution of pyridine (120 mg, 1.52 mmol) and 5-methylpyridin-2-amine (119 mg, 1.10 mmol) in DCM (1 mL) was added dropwise at 0° C. The resulting solution was stirred for 2 h at room temperature. The reaction mixture was concentrated under vacuum. The residue was applied onto a silica gel column with dichloromethane/methanol (93:7). This resulted in 19.7 mg (6%) of the title compound as a white solid. LCMS (ESI, m/z): [M+H]$^+$=338.1. $^1$HNMR (300 MHz, DMSO-d$_6$, ppm): δ 11.06 (s, 1H), 9.91 (s, 1H), 8.91 (s, 1H), 8.08-8.06 (m, 2H), 7.98-7.93 (m, 1H), 7.75-7.73 (m, 1H), 7.65-7.62 (m, 1H), 7.46-7.44 (m, 1H), 5.44-5.35 (m, 1H), 2.27 (s, 3H), 1.54 (d, J=6.9 Hz, 6H).

Example 2: Synthesis of Compound I-002

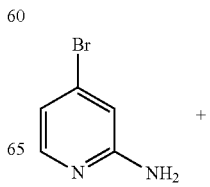

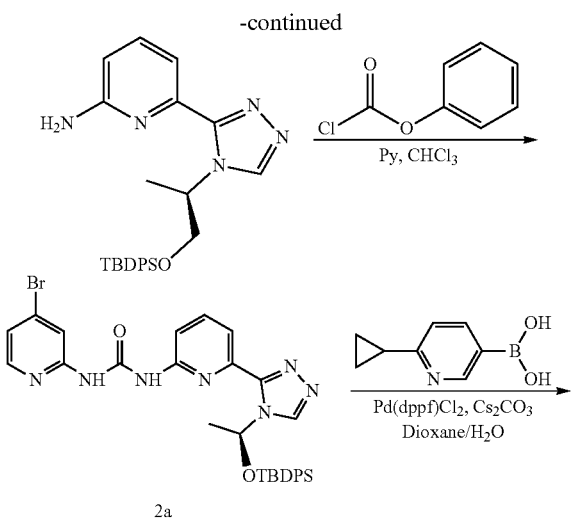

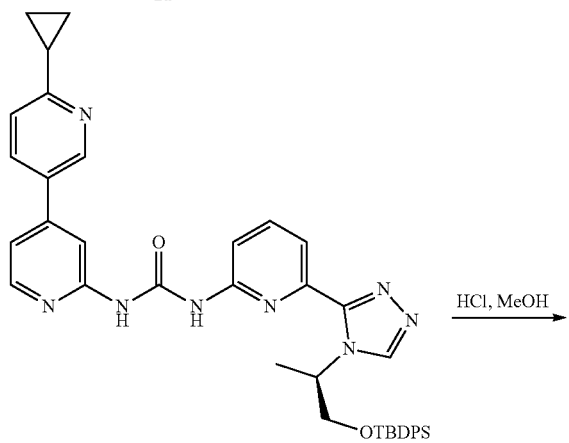

2b

I-002

(R)-1-(4-Bromopyridin-2-yl)-3-(6-(4-(1-(tert-butyl-diphenylsilyloxy)propan-2-yl)-4H-1,2,4-triazol-3-yl)pyridin-2-yl)urea (Compound 2a)

To a solution of 4-bromopyridin-2-amine (2.2 g, 12.8 mmol) in CHCl₃ (20 mL) was added pyridine (2.0 g, 25.6 mmol). Then phenyl carbonochloridate (2.0 g, 12.8 mmol) was added dropwise to the mixture at 0° C. The reaction mixture was stirred at room temperature for 16 h. Then a mixture of pyridine (2.0 g, 25.6 mmol) and 6-{4-[(2R)-1-[(tert-butyldiphenylsilyl)oxy]propan-2-yl]-4H-1,2,4-triazol-3-yl}pyridin-2-amine (2 g, 4.38 mmol) in CHCl₃ (5.0 mL) was added dropwise to the mixture at room temperature. The resulting mixture was stirred at 70° C. for 16 h. The resulting mixture was diluted with H₂O and extracted with ethyl acetate. The combined organic layer was washed with brine, dried over anhydrous sodium sulfate and filtered. The filtrate was evaporated in vacuo. The residue was purified by flash column chromatography with dichloromethane/methanol (9/1, v/v) to afford the title compound (1.5 g, 60%) as a light yellow solid. LCMS (ESI, m/z): [M+H]+=656.2.

1-(6-{4-[(2R)-1-[(tert-Butyldiphenylsilyl)oxy]propan-2-yl]-4H-1,2,4-triazol-3-yl}pyridin-2-yl)-3-[4-(6-cyclopropylpyridin-3-yl)pyridin-2-yl]urea (Compound 2b)

To a solution of Compound 2a (130 mg, 0.20 mmol) in dioxane (4.0 mL) and H₂O (1 mL) was added Pd(dppf)Cl₂ (14.5 mg, 0.02 mmol), Cs₂CO₃ (194 mg, 0.59 mmol) and (6-cyclopropylpyridin-3-yl)boronic acid (48.4 mg, 0.30 mmol). The mixture was stirred at 80° C. for 16 h under N₂ atmosphere. The resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with dichloromethane/methanol (9/1, v/v) to afford the title compound (88.0 mg, 67%) as a white solid. LCMS (ESI, m/z): [M+H]⁺=695.3.

3-[4-(6-Cyclopropylpyridin-3-yl)pyridin-2-yl]-1-(6-{4-[(2R)-1-hydroxypropan-2-yl]-4H-1,2,4-triazol-3-yl}pyridin-2-yl)urea (Compound I-002)

To a solution of Compound 2b (88.0 mg, 0.13 mmol) in MeOH (20.0 mL) was added HCl (6 mL, 1 mol/L). The resulting mixture was stirred at room temperature for 16 h. The mixture was concentrated under vacuum. The residue was purified by Prep-HPLC with the following conditions: Column: YMC-Actus Triart C18 30×250 mm, 5 um; Mobile Phase A: Water (10 mmol/L NH₄HCO₃), Mobile Phase B: ACN; Flow rate: 60 mL/min; Gradient: 34% B to 58% B in 7 min; 254/220 nm; Rt: 6.32 min to afford the title compound (8 mg, 14%) as a white solid. LCMS (ESI, m/z): [M+H]⁺=457.2. ¹H NMR (400 MHz, DMSO-d₆, ppm): δ 11.05 (s, 1H), 10.07 (s, 1H), 8.80 (s, 1H), 8.76 (d, J=2.0 Hz, 1H), 8.35 (d, J=5.2 Hz, 1H), 8.08 (d, J=8.0 Hz, 1H), 7.99-7.94 (m, 2H), 7.84 (s, 1H), 7.75-7.73 (m, 1H), 7.48-7.41 (m, 2H), 5.35-5.33 (m, 1H), 5.07-5.04 (m, 1H), 3.75-3.72 (m, 2H), 2.22-2.10 (m, 1H), 1.53 (d, J=6.8 Hz, 3H), 1.03-0.98 (m, 4H).

Example 3: Synthesis of Compound I-003

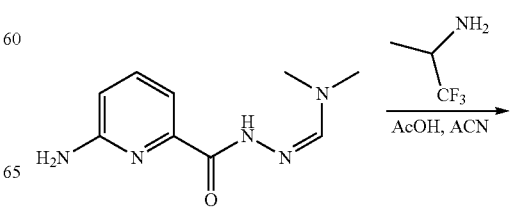

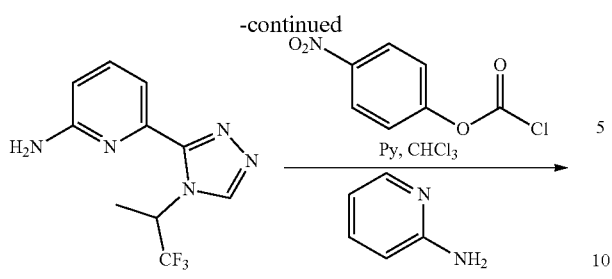

6-[4-(1,1,1-Trifluoropropan-2-yl)-4H-1,2,4-triazol-3-yl]pyridin-2-amine (Compound 3a)

To a solution of (Z)—N-(6-aminopicolinoyl)-N,N-dimethylformohydrazonamide (3.0 g, 14.5 mmol) in ACN (44 mL) was added $CH_3COOH$ (11 mL) at 0° C. The reaction mixture was stirred at 0° C. for 5 min. Then 1,1,1-trifluoropropan-2-amine (6.5 g, 57.5 mmol) was added to the mixture. The reaction mixture was stirred at 0° C. for 30 min and then stirred at 95° C. for 16 h. The resulting mixture was diluted with ethyl acetate. The resulted organic phase was washed with water, dried over anhydrous sodium sulfate and filtered. The filtrate was concentrated under vacuum. The residue was purified by flash column chromatography with dichloromethane/methanol (14/1, v/v) to afford the title compound (1.2 g, 34%) as a white solid, LCMS (ESI, m/z): [M+H]$^+$=258.1. 3-(Pyridin-2-yl)-1-[6-[4-(1,1,1-trifluoropropan-2-yl)-4H-1,2,4-triazol-3-yl]pyridin-2-yl]urea (Compound I-003):

To a solution of pyridin-2-amine (44.0 mg, 0.47 mmol) in $CHCl_3$ (2 mL) was added pyridine (75.0 mg, 0.95 mmol). Then a solution of 4-nitrophenyl carbonochloridate (94.0 mg, 0.47 mmol) in $CHCl_3$ (2 mL) was added dropwise to the mixture at 0° C. The reaction mixture was stirred at room temperature for 16 h. Then a mixture of pyridine (75.0 mg, 0.95 mmol) and Compound 3a (60.0 mg, 0.23 mmol) in $CHCl_3$ (2 mL) was added dropwise to the mixture at 0° C. The resulting mixture was stirred at room temperature for another 2 h. The reaction mixture was diluted with DCM. The resulted mixture was washed with brine, dried over anhydrous sodium sulfate and filtered. The filtrate was concentrated under vacuum. The residue was purified by flash column chromatography with dichloromethane/methanol (93/7, v/v) to afford the crude product. The crude product was purified by Prep-HPLC with the following conditions: Column: XBridge Shield RP18 OBD Column 30×150 mm, 5 um; Mobile Phase A: Water (10 mmol/L $NH_4HCO_3$), Mobile Phase B: ACN; Flow rate: 60 mL/min; Gradient: 25% B to 55% B in 7 min; 254/220 nm; Rt: 5.73 min to the title compound (53.7 mg, 61%) as a white solid. LCMS (ESI, m/z): [M+H]$^+$=378.2. $^1$H NMR (400 MHz, DMSO-$d_6$, ppm): δ 11.25 (s, 1H), 9.92 (s, 1H), 9.15 (s, 1H), 8.26-8.24 (m, 1H), 8.11-8.09 (m, 1H), 8.01-7.97 (m, 1H), 7.89-7.86 (m, 1H), 7.83-7.78 (m, 1H), 7.51 (d, J=8.4 Hz, 1H), 7.09-7.06 (m, 1H), 6.83-6.76 (m, 1H), 1.86 (d, J=7.2 Hz, 3H).

Example 4: Synthesis of Compound I-004

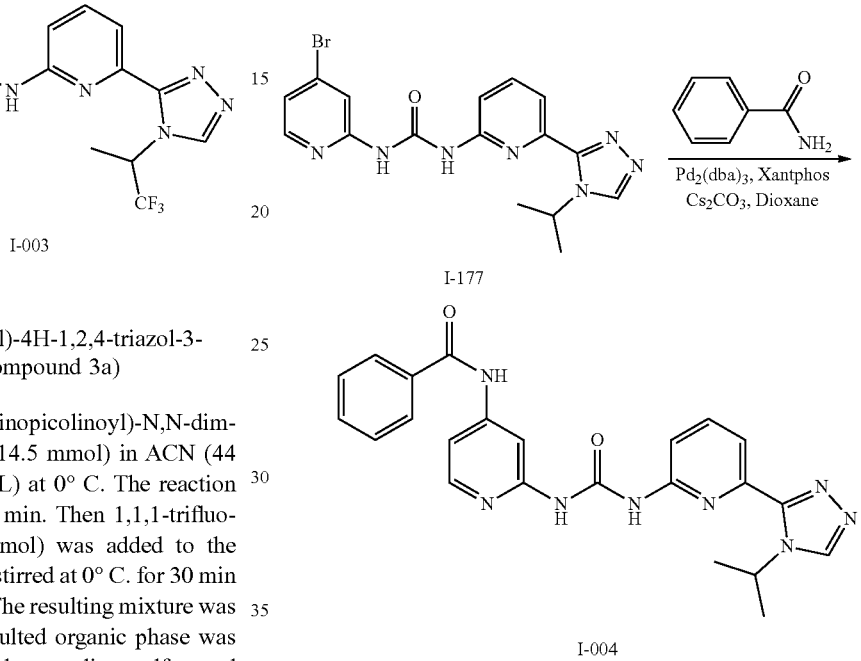

N-(2-(3-(6-(4-Isopropyl-4H-1,2,4-triazol-3-yl)pyridin-2-yl)ureido)pyridin-4-yl)benzamide (Compound I-004)

To a solution of Compound I-177 (100 mg, 0.25 mmol) in dioxane (4 mL) was added $Pd_2(dba)_3$ (25.9 mg, 0.03 mmol), Xantphos (28.9 mg, 0.05 mmol), $Cs_2CO_3$ (245 mg, 0.75 mmol) and benzamide (200 mg, 1.65 mmol). The mixture was stirred at 100° C. for 16 h under $N_2$ atmosphere. The resulting mixture was diluted with $H_2O$ and extracted with ethyl acetate. The combined organic layer was washed with brine, dried over anhydrous sodium sulfate and filtered. The filtrate was concentrated under vacuum. The residue was purified by Prep-HPLC with the following conditions: Column: XBridge Prep OBD C18 Column 30×150 mm, 5 um; Mobile Phase A: Water (10 mmol/L $NH_4HCO_3$), Mobile Phase B: ACN; Flow rate: 60 mL/min; Gradient: 26% B to 49% B in 7 min; 254 nm; Rt: 6.82 min to afford the title compound (22.1 mg, 20%) as a white solid. LCMS (ESI, m/z): [M+H]$^+$=443.2. $^1$HNMR (400 MHz, DMSO-$d_6$, ppm): δ 11.32 (s, 1H), 10.68 (s, 1H), 9.99 (s, 1H), 8.89 (s, 1H), 8.16 (d, J=5.6 Hz, 1H), 8.09-8.07 (m, 2H), 7.99-7.94 (m, 3H), 7.74 (d, J=7.2 Hz, 1H), 7.65-7.49 (m, 4H), 5.44-5.37 (m, 1H), 1.54 (d, J=6.4 Hz, 6H).

Example 5: Synthesis of Compound I-005

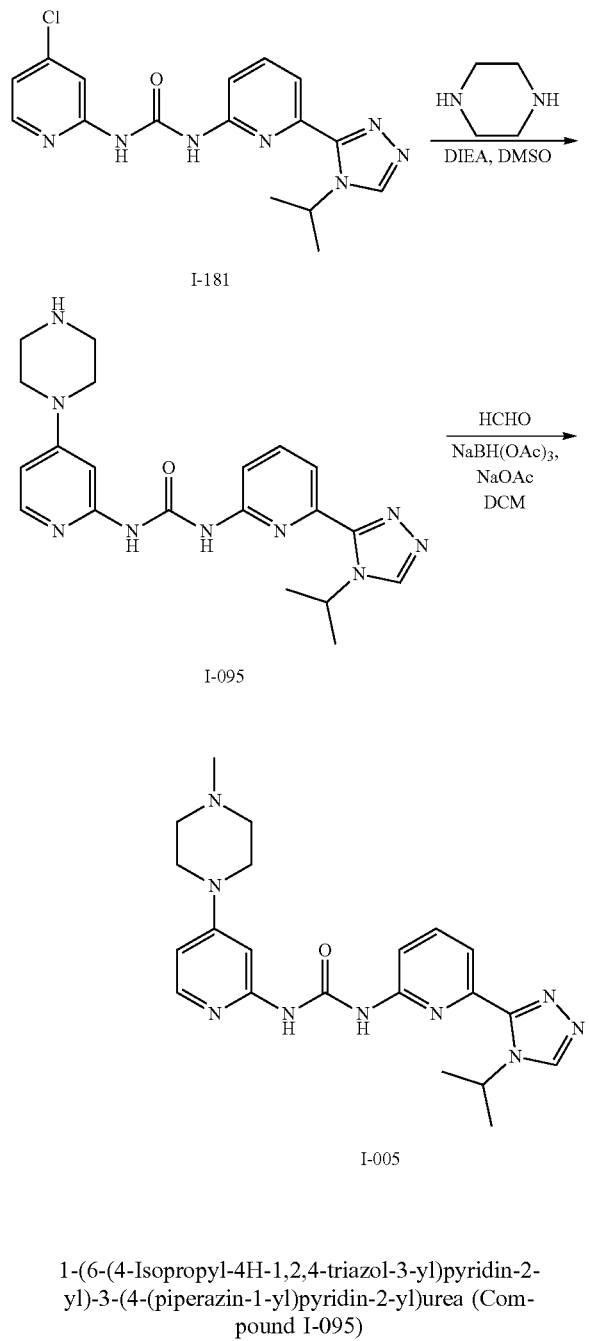

1-(6-(4-Isopropyl-4H-1,2,4-triazol-3-yl)pyridin-2-yl)-3-(4-(piperazin-1-yl)pyridin-2-yl)urea (Compound I-095)

To a solution of Compound I-181 (200 mg, 0.56 mmol) in DMSO (5 mL) was added piperazine (58.0 mg, 0.67 mmol) and DIEA (0.2 ml, 1.33 mmol). The reaction mixture was stirred at 100° C. for 16 h. The reaction mixture was diluted with H$_2$O and extracted with EtOAc. The combined organic phase was washed with brine, dried over anhydrous sodium sulfate and filtered. The filtrate was concentrated under vacuum. The residue was purified by flash column chromatography with ethyl acetate/petroleum ether (7/3, v/v) to afford the title compound (100.0 mg, 90%) as a white solid. LCMS (ESI, m/z): [M+H]$^+$=408.2.

1-(6-(4-Isopropyl-4H-1,2,4-triazol-3-yl)pyridin-2-yl)-3-(4-(4-methylpiperazin-1-yl)pyridin-2-yl)urea (Compound I-005)

To a mixture of Compound I-095 (50.0 mg, 0.12 mmol) and HCHO (5.4 mg, 0.18 mmol) in dichloromethane (5 mL) was added NaOAc (10.0 mg, 0.07 mmol). The reaction mixture was stirred at room temperature for 1 h. Then NaBH(OAc)$_3$ (19.8 mg, 0.09 mmol) was added to the mixture. The resulting mixture was stirred at room temperature for 16 h. The reaction mixture was concentrated under vacuum. The residue was purified by Prep-HPLC with the following conditions (IntelFlash-1): Column: XBridge Shield RP18 OBD Column 30×150 mm, 5 um; Mobile Phase A: Water (10 mmol/L NH$_4$HCO$_3$), Mobile Phase B: ACN; Flow rate: 60 mL/min; Gradient: 16% B to 45% B in 7 min; 254/220 nm; Rt: 6.23 min to afford the title compound (11.2 mg, 21%) as a white solid. LCMS (ESI, m/z): [M+H]$^+$=422.2. $^1$H NMR (300 MHz, DMSO-d$_6$, ppm): δ 11.94 (s, 1H), 9.61 (s, 1H), 8.89 (s, 1H), 8.10-8.08 (m, 1H), 7.96-7.86 (m, 2H), 7.73 (d, J=6.9 Hz, 1H), 6.77 (s, 1H), 6.62-6.52 (m, 1H), 5.42-5.33 (m, 1H), 3.29-3.27 (m, 4H), 2.43-2.40 (m, 4H), 2.22 (s, 3H), 1.54 (d, J=6.9 Hz, 6H).

Example 6: Synthesis of Compound I-006

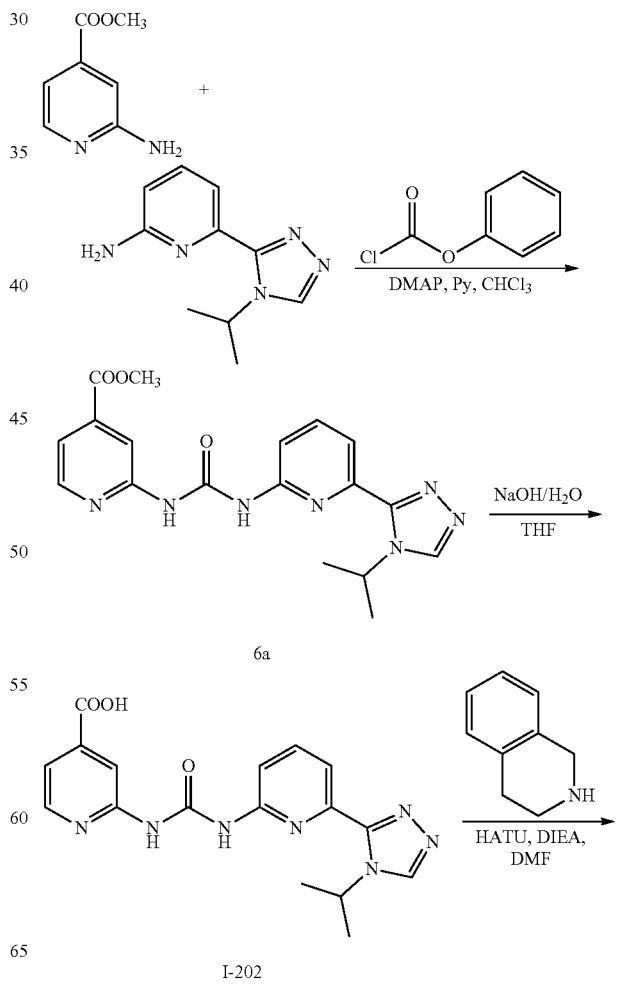

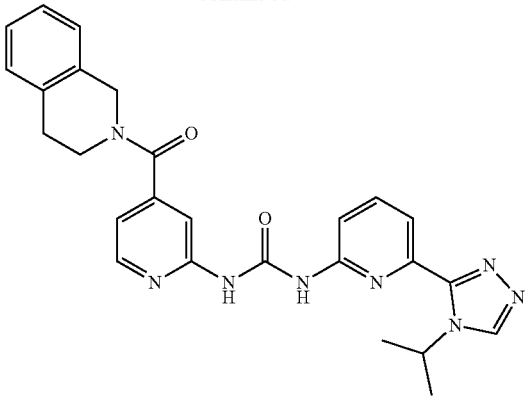

I-006

Methyl 2-(3-(6-(4-isopropyl-4H-1,2,4-triazol-3-yl)pyridin-2-yl)ureido)isonicotinate (Compound 6a)

To a solution of phenyl carbonochloridate (1.03 g, 6.57 mmol) in CHCl₃ (5 mL) was added pyridine (526 mg, 6.57 mmol) and DMAP (80.3 mg, 0.66 mmol) at 0° C. Then a solution of methyl 2-aminoisonicotinate (500 mg, 3.29 mmol) in CHCl₃ (3 mL) was added dropwise to the mixture. The reaction mixture was stirred at room temperature for 16 h. Then a mixture of pyridine (526 mg, 6.57 mmol) and 6-(4-isopropyl-4H-1,2,4-triazol-3-yl)pyridin-2-amine (668 mg, 3.29 mmol) in CHCl₃ (2 mL) was added dropwise to the mixture at 0° C. The resulting mixture was stirred at 70° C. for 5 h. The reaction mixture was diluted with DCM. The organic layer was washed with brine, dried over anhydrous sodium sulfate and filtered. The filtrate was concentrated under vacuum. The residue was purified by flash column chromatography with dichloromethane/methanol (10/1, v/v) to afford the title compound (32 mg, 26%) as a yellow solid. LCMS (ESI, m/z): [M+H]⁺=382.2.

2-(3-(6-(4-Isopropyl-4H-1,2,4-triazol-3-yl)pyridin-2-yl)ureido)isonicotinic acid (Compound I-202)

To a solution of Compound 6a (320 mg, 0.84 mmol) in THF (20 mL) was added a solution of NaOH (67.0 mg, 1.67 mmol) in water (5 mL). The resulting mixture was stirred at room temperature for 1 h. The resulting mixture was diluted with H₂O. The pH value of the mixture was adjusted to 6 with HCl (1 mol/L) and extracted with ethyl acetate. The combined organic layer was washed with brine, dried over anhydrous sodium sulfate and filtered. The filtrate was concentrated under vacuum. The residue was purified by flash column chromatography with dichloromethane/methanol (7/1, v/v) to afford the title compound (150 mg, 48%) as a white solid. LCMS (ESI, m/z): [M+H]⁺=368.1.

1-(6-(4-Isopropyl-4H-1,2,4-triazol-3-yl)pyridin-2-yl)-3-(4-(1,2,3,4-tetrahydroisoquinoline-2-carbonyl)pyridin-2-yl)urea (Compound I-006)

To a solution of Compound I-202 (30.0 mg, 0.08 mmol) in DMF (3 mL) was added HATU (37.4 mg, 0.10 mmol), DIEA (31.7 mg, 0.25 mmol) and 1,2,3,4-tetrahydroisoquinoline (10.9 mg, 0.08 mmol). The resulting mixture was stirred at room temperature for 2 h. The resulting mixture was diluted with H₂O and extracted with ethyl acetate. The combined organic layer was washed with brine, dried over anhydrous sodium sulfate and filtered. The filtrate was concentrated under vacuum. The residue was purified by Prep-HPLC with the following conditions: Column: XBridge Shield RP18 OBD Column 30×150 mm, 5 um; Mobile Phase A: Water (10 mmol/L NH₄HCO₃), Mobile Phase B: ACN; Flow rate: 60 mL/min; Gradient: 14% B to 30% B in 10 min; 220/254 nm; Rt: 9.85 min to afford the title compound (10.6 mg, 27%) as a white solid. LCMS (ESI, m/z): [M+H]⁺=483.2. ¹H NMR (400 MHz, DMSO-d₆, ppm): δ 10.83 (s, 1H), 10.15 (s, 1H), 8.90 (s, 1H), 8.36 (d, J=4.8 Hz, 1H), 8.04 (d, J=8.4 Hz, 1H), 7.98-7.96 (m, 1H), 7.76-7.74 (m, 1H), 7.60-7.55 (m, 1H), 7.27-7.13 (m, 5H), 5.48-5.35 (m, 1H), 4.79 and 4.52 (s, total 2H), 3.55-3.53 (m, 2H), 2.90-2.80 (m, 2H), 1.54 (d, J=6.8 Hz, 6H).

Example 7: Synthesis of Compound I-007

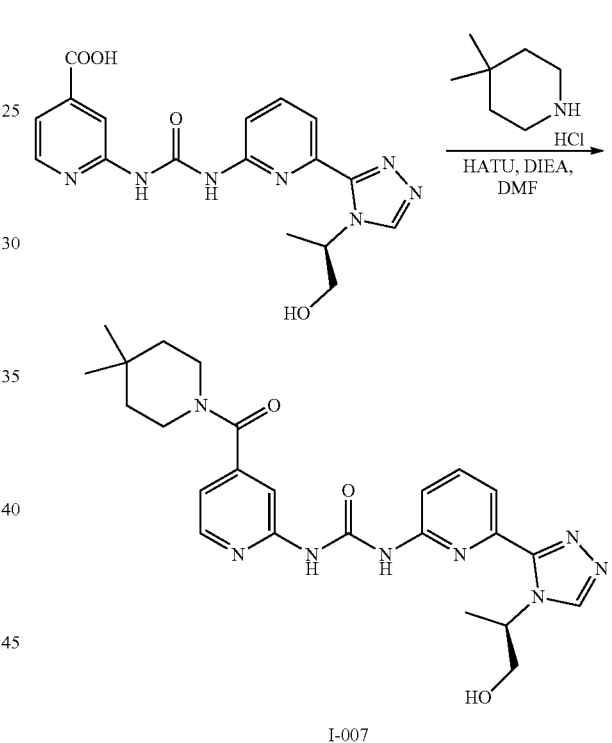

I-007

(R)-1-(4-(4,4-Dimethylpiperidine-1-carbonyl)pyridin-2-yl)-3-(6-(4-(1-hydroxypropan-2-yl)-4H-1,2,4-triazol-3-yl)pyridin-2-yl)urea (Compound I-007)

To a solution of (R)-2-(3-(6-(4-(1-hydroxypropan-2-yl)-4H-1,2,4-triazol-3-yl)pyridin-2-yl)ureido)isonicotinic acid (100 mg, 0.26 mmol) in DMF (3 mL) was added HATU (149 mg, 0.39 mmol), DIEA (101 mg, 0.78 mmol) and 4,4-dimethylpiperidine hydrochloride (58.1 mg, 0.39 mmol). The mixture was stirred at room temperature for 2 h. The resulting mixture was concentrated under vacuum. The residue was purified by Prep-HPLC with the following conditions: Column: XBridge Prep OBD C18 Column 30×150 mm, 5 um; Mobile Phase A: Water (10 mmol/L NH₄HCO₃), Mobile Phase B: ACN; Flow rate: 60 mL/min; Gradient: 21% B to 38% B in 10 min; 254/220 nm; Rt: 10.27 min to afford the title compound (4.8 mg, 4%) as a white solid. LCMS (ESI, m/z): [M+H]⁺=479.2. ¹HNMR (400 MHz, DMSO-d₆, ppm): δ 10.78 (s, 1H), 10.11 (s, 1H), 8.79 (s, 1H), 8.33 (d, J=5.2 Hz, 1H), 8.04 (d, J=8.4 Hz, 1H), 7.98-7.94 (m, 1H), 7.74 (d, J=7.6 Hz, 1H), 7.55 (s, 1H), 7.03 (d, J=5.2 Hz, 1H), 5.35-5.30 (m, 1H), 5.06-5.03 (m, 1H), 3.73-3.70 (m, 2H), 3.62-3.60 (m, 2H), 3.28-3.20 (m, 2H), 1.51 (d, J=6.8 Hz, 3H), 1.40-1.32 (m, 2H), 1.31-1.25 (m, 2H), 0.97 (s, 6H).

Example 8: Synthesis of Compound I-008

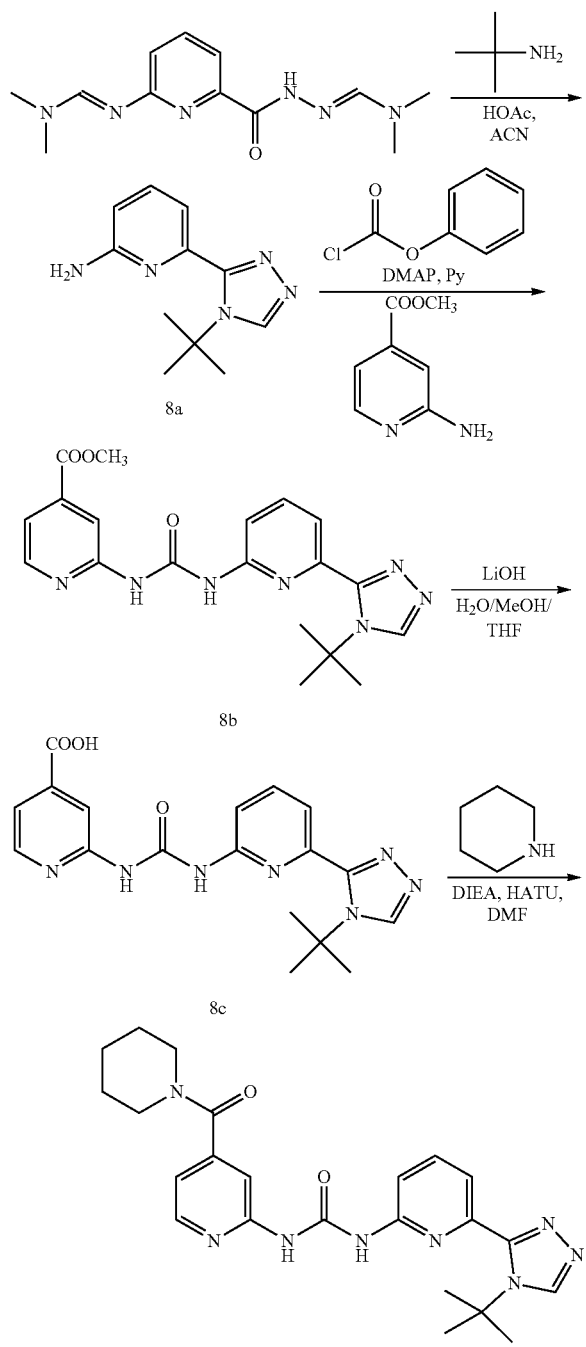

6-(4-tert-butyl-4H-1,2,4-Triazol-3-yl)pyridin-2-amine (Compound 8a)

To a solution of (E)-N'-(6-((E)-2-((dimethylamino)methylene)hydrazinecarbonyl)pyridin-2-yl)-N,N-dimethylformimidamide (1.7 g, 6.49 mmol) in HOAc (2 mL) and ACN (8 mL) was added 2-methylpropan-2-amine (2.4 g, 32.4 mmol). The resulting mixture was stirred at 95° C. for 5 h. After the reaction was completed, the pH value of the mixture was adjusted to 8 with NaOH (50%) and then evaporated in vacuo. The residue was purified by reverse phase flash column chromatography with 5-50% ACN in H₂O to afford the title compound (470 mg, 33%) as a yellow solid. LCMS (ESI, m/z): [M+H]⁺=218.1

Methyl 2-([[6-(4-tert-butyl-4H-1,2,4-triazol-3-yl)pyridin-2-yl]carbamoyl]amino)pyridine-4-carboxylate (Compound 8b)

To a solution of methyl 2-aminopyridine-4-carboxylate (330 mg, 2.17 mmol) in pyridine (5 mL) was added DMAP (13.2 mg, 0.11 mmol) and phenyl carbonochloridate (507.0 mg, 3.25 mmol). The resulting mixture was stirred at room temperature for 16 h. Then Compound 6a (470 mg, 1.0 mmol) was added to the mixture. The reaction mixture was stirred at 70° C. for 48 h. The resulting mixture was concentrated. The residue was purified by flash column chromatography with DCM/MeOH (20/1, v/v) to afford the title compound (300 mg, 35%) as a white solid. LCMS (ESI, m/z): [M+H]⁺=396.2

2-([[6-(4-tert-Butyl-4H-1,2,4-triazol-3-yl)pyridin-2-yl]carbamoyl]amino)pyridine-4-carboxylic acid (Compound 8c)

To a solution of Compound 8b (300 mg, 0.76 mmol) in MeOH/H₂O/THF (2/2/2 mL) was added LiOH (182 mg, 7.59 mmol). The resulting mixture was stirred at room temperature for 2 h. The pH value of the mixture was adjusted to 6 with HCl (1 mol/L) and then filtered. The solid was collected and dried to afford the title compound (260 mg, 90%) as an off-white solid. LCMS (ESI, m/z): [M+H]⁺=382.

3-[6-(4-tert-Butyl-4H-1,2,4-triazol-3-yl)pyridin-2-yl]-1-[4-(piperidine-1-carbonyl)pyridin-2-yl]urea (Compound I-008)

To a solution of Compound 8c (170 mg, 0.45 mmol) in DMF (2.5 mL) was added piperidine (45.5 mg, 0.54 mmol) and DIEA (288.0 mg, 2.23 mmol). The reaction mixture was stirred at room temperature for 0.5 h. Then HATU (203 mg, 0.54 mmol) was added to the mixture. The resulting mixture was stirred at room temperature for 2 h. After the reaction was completed, the mixture was diluted with H₂O and extracted with ethyl acetate. The combined organic layer was concentrated under vacuum. The residue was purified by Prep-HPLC with the following conditions: Column: XBridge Prep OBD C18 Column 30×150 mm, 5 um; Mobile Phase A: Water (10 mmol/L NH₄HCO₃), Mobile Phase B: ACN; Flow rate: 60 mL/min; Gradient: 21% B to 44% B in 7 min; 254/220 nm; Rt: 6.5 min to afford the title compound (77.9 mg, 39%) as a white solid. LCMS (ESI, m/z): [M+H]⁺=449.2; ¹H NMR (300 MHz, DMSO-d₆, ppm): δ 10.85 (s, 1H), 10.12 (s, 1H), 8.74 (s, 1H), 8.28 (d, J=4.8 Hz, 1H), 8.06

(d, J=8.1 Hz, 1H), 7.96-7.91 (m, 1H), 7.55 (s, 1H), 7.41-7.39 (m, 1H), 7.01-6.98 (m, 1H), 3.60-3.50 (m, 2H), 3.22-3.15 (m, 2H), 1.56-1.45 (m, 15H).

Example 9: Synthesis of Compound I-009

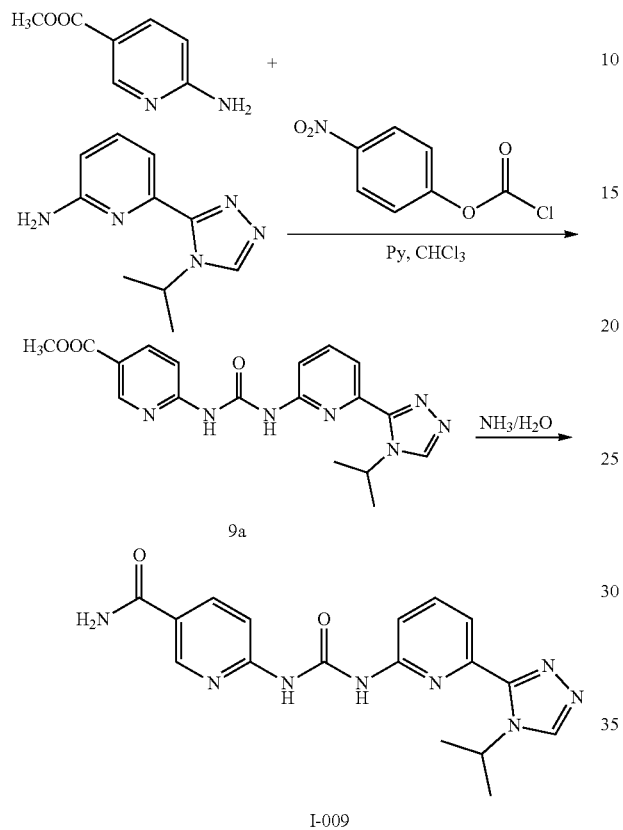

Methyl-6-(3-(6-(4-isopropyl-4H-1,2,4-triazol-3-yl)pyridin-2-yl)ureido)nicotinate (Compound 9a)

To a solution of methyl 6-aminonicotinate (76.0 mg, 0.50 mmol) in CHCl₃ (2 mL) was added pyridine (80.0 mg, 1.01 mmol). Then a solution of 4-nitrophenyl chloroformate (100 mg, 0.50 mmol) in CHCl₃ (1 mL) was added dropwise to the mixture at 0° C. The mixture was stirred at room temperature for 16 h. Then a mixture of pyridine (80.0 mg, 1.01 mmol) and 6-[4-(propan-2-yl)-4H-1,2,4-triazol-3-yl]pyridin-2-amine (100 mg, 0.50 mmol) in CHCl₃ (1 mL) was added dropwise to the mixture at 0° C. The resulting mixture was stirred at room temperature for another 2 h. The reaction mixture was diluted with DCM. The resulted mixture was washed with brine, dried over anhydrous sodium sulfate and filtered. The filtrate was concentrated under vacuum. The residue was purified by flash column chromatography with dichloromethane/methanol (93/7, v/v) to afford the title compound (25 mg, 13%) as a white solid. LCMS (ESI, m/z): [M+H]⁺=382.1

6-(3-(6-(4-Isopropyl-4H-1,2,4-triazol-3-yl)pyridin-2-yl)ureido)nicotinamide (Compound I-009)

The solution of Compound 9a (25.0 mg, 0.07 mmol) in NH₃/H₂O (3 mL) was stirred at room temperature for 16 h. The mixture was concentrated under vacuum. The residue was purified by Prep-HPLC with the following conditions: Column: XBridge Prep C18 OBD Column 19×150 mm 5 um; Mobile Phase A: Water (10 mmol/L NH₄HCO₃), Mobile Phase B: ACN; Flow rate: 25 mL/min; Gradient: 14% B to 55% B in 7 min; 254/220 nm; Rt: 4.73, 6.53 min to afford the title compound (8.5 mg, 35%) as a white solid. LCMS (ESI, m/z): [M+H]⁺=367.2. ¹H NMR (300 MHz, DMSO-d₆, ppm): δ 10.74 (s, 1H), 10.22 (s, 1H), 8.90 (s, 1H), 8.73 (d, J=1.5 Hz, 1H), 8.24-8.20 (m, 1H), 8.08-7.95 (m, 3H), 7.77-7.70 (m, 1H), 7.67-7.62 (m, 1H), 7.45 (s, 1H), 5.44-5.37 (m, 1H), 1.54 (d, J=6.9 Hz, 6H).

Example 10: Synthesis of Compound I-010

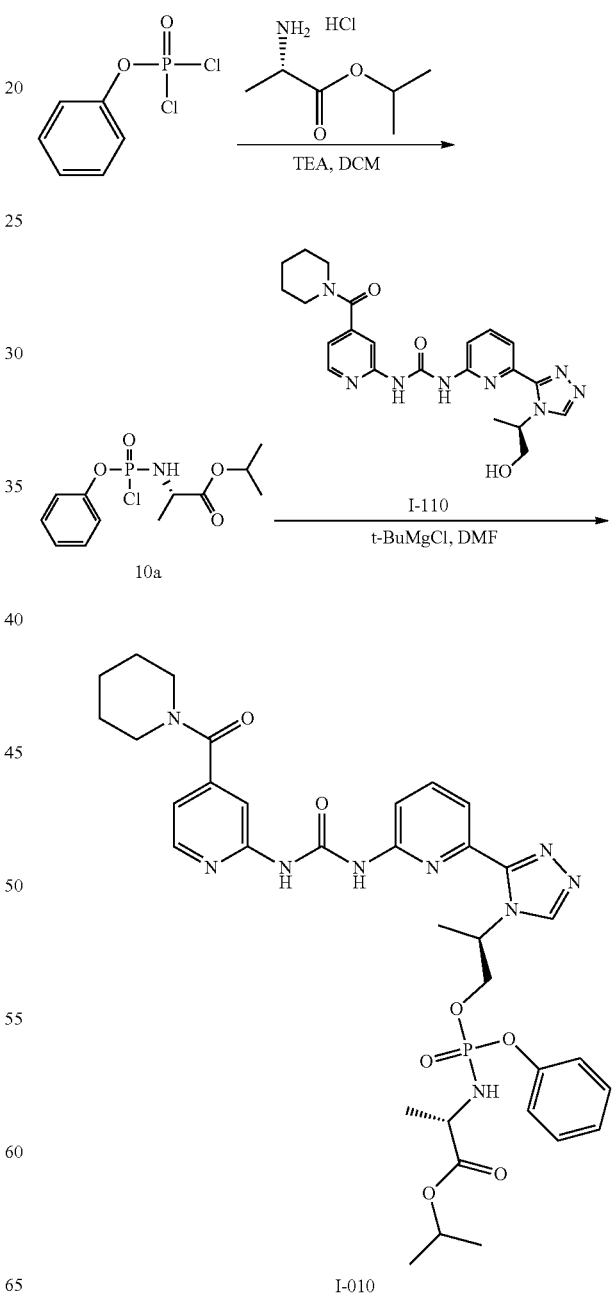

Propan-2-yl (2S)-2-[[chloro(phenoxy)phosphoryl]amino]propanoate (Compound 10a)

To a mixture of phenyl chlorophosphonochloridate (3.5 g, 16.5 mmol) and propan-2-yl (2S)-2-aminopropanoate (2.0 g, 14.9 mmol) in DCM (55 mL) was added TEA (2.5 g, 25.00 mmol) at −78° C. under $N_2$. The mixture was stirred at −78° C. for 1 h and then stirred at room temperature for 2.5 h. The mixture was evaporated in vacuo. The residue was dissolved with $Et_2O$ and then filtered. The filtrate was purified by flash column chromatography with petroleum ether/EtOAc (4/1, v/v) to afford the title compound (1.2 g, 26%) as a colorless oil.

Propan-2-yl (2S)-2-([phenoxy[(2R)-2-[3-[6-([[4-(piperidine-1-carbonyl)pyridin-2-yl]carbamoyl]amino)pyridin-2-yl]-4H-1,2,4-triazol-4-yl]propoxy]phosphoryl]amino)-propanoate (Compound I-010)

To a mixture of Compound I-110 (300 mg, 0.67 mmol) and Compound 10a (1.2 g, 3.93 mmol) in DMF (15 mL) was added t-BuMgCl (6.1 mL, 10.4 mmol, 1.7 mol/L) at −40° C. under $N_2$. The mixture was stirred at −40° C. to room temperature for 16 h. The mixture was quenched by $NH_4Cl$ solution and then diluted with $H_2O$. The mixture was extracted with EtOAc. The combined organic layer was washed with brine, dried over $Na_2SO_4$ and filtered. The filtrate was evaporated in vacuo. The residue was purified by flash column chromatography with DCM/$CH_3OH$ (92/8, v/v) to afford the title compound (272 mg, 56%) as a white solid. LCMS (ESI, m/z): [M+H]$^+$=720.3. $^1$H NMR (300 MHz, DMSO-$d_6$, ppm): δ 10.86 (s, 1H), 9.99 (s, 1H), 8.89 and 8.81 (s, total 1H), 8.38-8.36 (m, 1H), 8.08-8.05 (m, 1H), 8.00-7.95 (m, 1H), 7.79-7.73 (m, 1H), 7.61-7.50 (m, 1H), 7.36-6.95 (m, 6H), 6.10-5.96 (m, 1H), 5.76-5.50 (m, 1H), 4.80-4.76 (m, 1H), 4.52-4.24 (m, 2H), 3.60-3.49 (m, 3H), 3.30-3.19 (m, 2H), 1.68-1.42 (m, 9H), 1.14-1.07 (m, 9H).

Example 11: Synthesis of Compound I-011

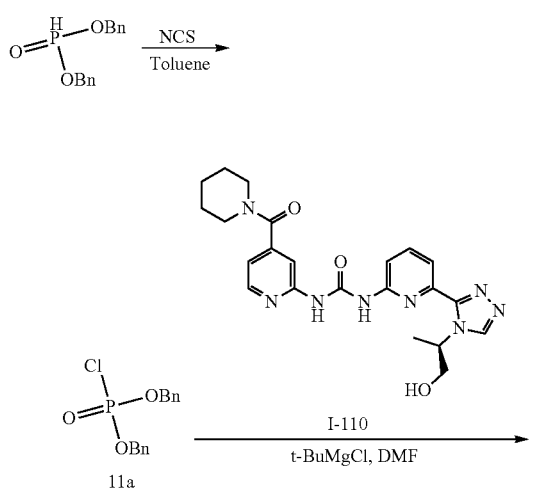

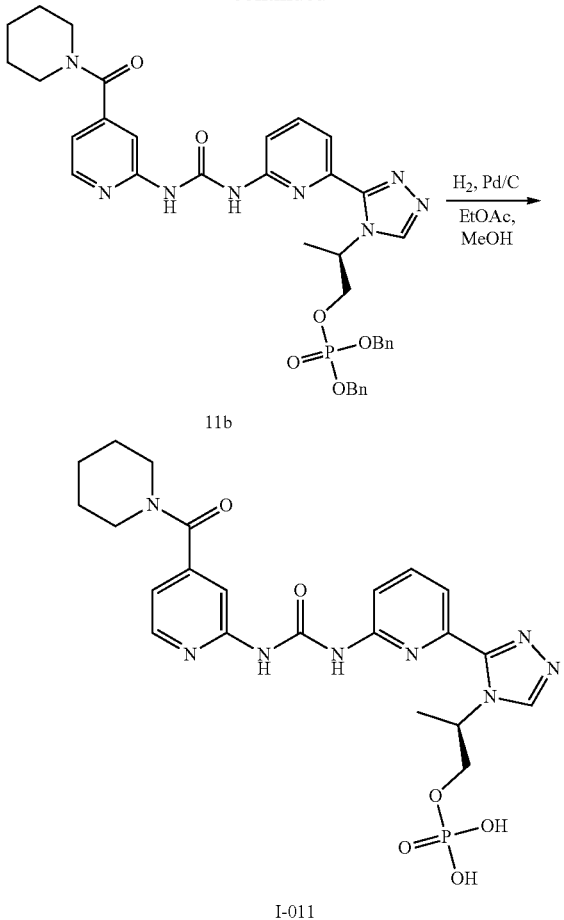

Dibenzyl Phosphorochloridate (Compound 11a):

A mixture of dibenzyl phosphonate (3.0 g, 11.4 mmol) and NCS (1.5 g, 11.4 mmol) in toluene (50 mL) was stirred at room temperature for 2 h. After the reaction was completed, the reaction mixture was filtered. The filtrate was evaporated in vacuo. The residue was purified by flash column chromatography with petroleum ether/EtOAc (4/1, v/v) to afford the title compound (1.8 g, 55%) as a colorless oil.

Dibenzyl (2R)-2-[3-[6-([[4-(piperidine-1-carbonyl)pyridin-2-yl]carbamoyl]amino)pyridin-2-yl]-4H-1,2,4-triazol-4-yl]propyl phosphate (Compound 11b)

To a mixture of Compound 11a (1.8 g, 6.30 mmol) and Compound I-110 (460 mg, 1.02 mmol) in DMF (40 mL) was dropwise added t-BuMgCl (6.0 mL, 10.2 mmol, 1.7 mol/L) at −40° C. under $N_2$. The mixture was stirred at −40° C. to room temperature for 2 h. The mixture was quenched by $NH_4Cl$ solution and then extracted with EtOAc. The combined organic layer was washed with brine, dried over Na2SO4 and filtered. The filtrate was evaporated in vacuo. The residue was purified by flash column chromatography with DCM/$CH_3OH$ (94/6, v/v) to afford the title compound (120 mg, 16%) as a light yellow solid. LCMS (ESI, m/z): [M+H]$^+$=711.3

[(2R)-2-[3-[6-([[4-(Piperidine-1-carbonyl)pyridin-2-yl]carbamoyl]amino)pyridin-2-yl]-4H-1,2,4-triazol-4-yl]propoxy]phosphonic acid (Compound I-011)

To a mixture of Compound 11b (120 mg, 0.17 mmol) in EtOAc (5 mL) and CH$_{30}$H (5 mL) was added Pd/C (80.0 mg, wet). The mixture was stirred at room temperature for 2 h under H$_2$. After the reaction was completed, the reaction mixture was filtered. The filtrate was evaporated in vacuo. The residue was purified by Prep-HPLC with the following conditions: Column: XBridge Prep OBD C18 Column 30×150 mm, 5 um; Mobile Phase A: Water (10 mmol/L NH$_4$HCO$_3$), Mobile Phase B: ACN; Flow rate: 60 m/min; Gradient: 5% B to 22% B in 7 min; 254/220 nm; Rt: 5.57 min to afford the title compound (14.1 mg, 15%) as a white solid. LCMS (ESI, m/z): [M+H]$^+$=531.4. $^1$H NMR (300 MHz, DMSO-d$_6$+D$_2$O, ppm): δ 8.84 (s, 1H), 8.32-8.30 (m, 1H), 8.03-7.90 (m, 3H), 7.70-7.67 (m, 1H), 6.99-6.97 (m, 1H), 5.17-5.10 (m, 1H), 4.73-4.65 (m, 1H), 3.61-3.48 (m, 3H), 3.30-3.19 (m, 2H), 1.68-1.43 (m, 9H).

Example 12: Synthesis of Compound I-012

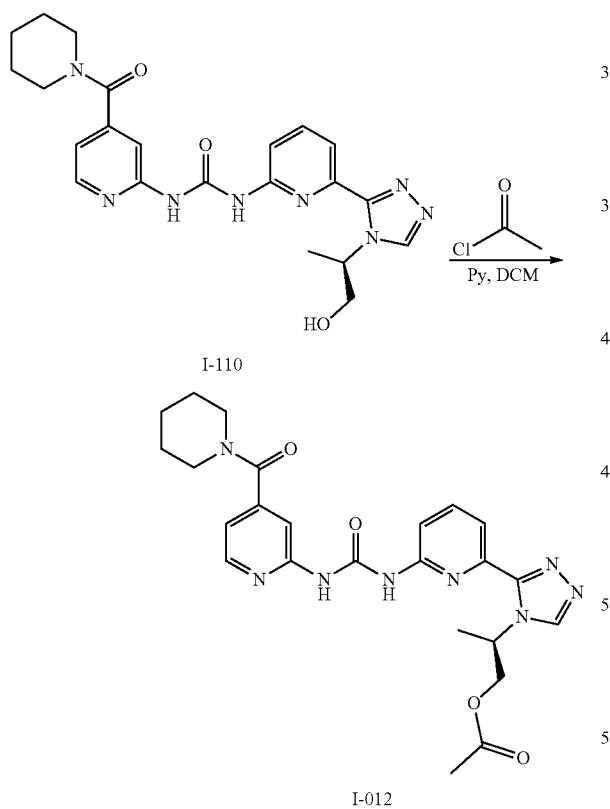

(2R)-2-[3-[6-([[4-(Piperidine-1-carbonyl)pyridin-2-yl]carbamoyl]amino)pyridin-2-yl]-4H-1,2,4-triazol-4-yl]propyl acetate (Compound I-012)

To a solution of Compound I-110 (100 mg, 0.22 mmol) in DCM (3 mL) was added pyridine (88.9 mg, 1.11 mmol).

Then acetyl chloride (52.3 mg, 0.67 mmol) was added to the mixture at 0° C. The resulting mixture was stirred at room temperature for 2 h. The mixture was diluted with H$_2$O and extracted with dichloromethane. The combined organic layer was washed with brine, dried over anhydrous sodium sulfate and filtered. The filtrate was concentrated under vacuum. The residue was purified by Prep-HPLC with the following conditions: Column: XSelect CSH Prep C18 OBD Column, 5 um; 19×150 mm; Mobile Phase A: Water (0.1% FA), Mobile Phase B: ACN; Flow rate: 25 mL/min; Gradient: 30% B to 56% B in 7 min; 254/220 nm; Rt: 6.53 min to afford the title compound (42.4 mg, 39%) as a white solid. LCMS (ESI, m/z): [M+H]$^+$=493.2. $^1$H NMR (300 MHz, DMSO-d$_6$, ppm): δ 10.79 (s, 1H), 10.12 (s, 1H), 8.93 (s, 1H), 8.36 (d, J=5.1 Hz, 1H), 8.06-7.95 (m, 2H), 7.78-7.75 (m, 1H), 7.57 (s, 1H), 7.05-7.02 (m, 1H), 5.68-5.62 (m, 1H), 4.47-4.42 (m, 1H), 4.34-4.30 (m, 1H), 3.65-3.52 (m, 2H), 3.30-3.17 (m, 2H), 1.83 (s, 3H), 1.60 (d, J=6.9 Hz, 7H), 1.52-1.43 (m, 2H).

Example 13: Synthesis of Compound I-013

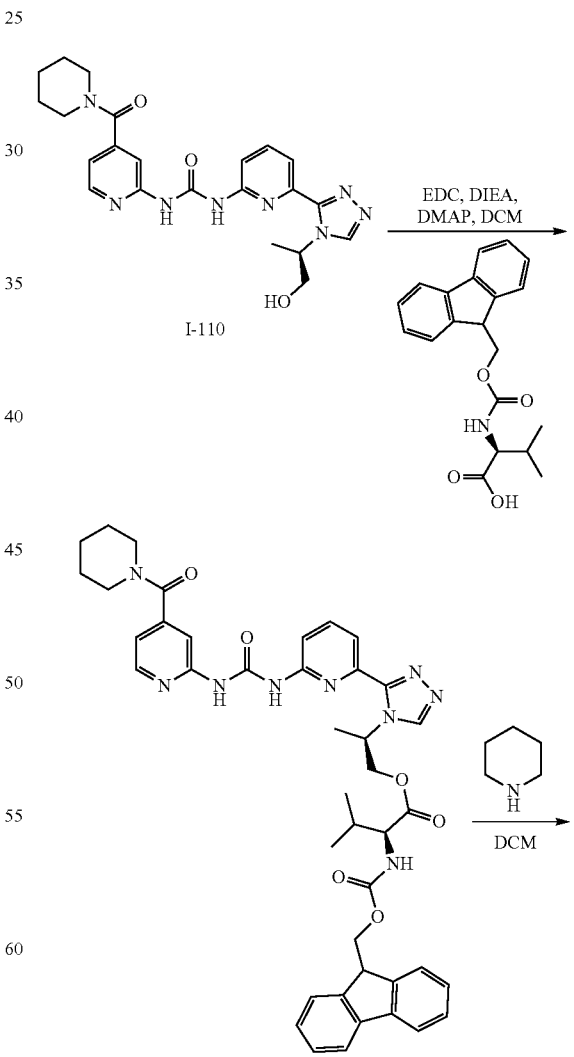

13a 3.64-3.55 (m, 2H), 3.30-3.20 (m, 2H), 2.96 (d, J=5.1 Hz, 1H), 1.68-1.44 (m, 12H), 0.68 (d, J=6.9 Hz, 3H), 0.59 (d, J=6.9 Hz, 3H).

Example 14: Synthesis of Compound I-014

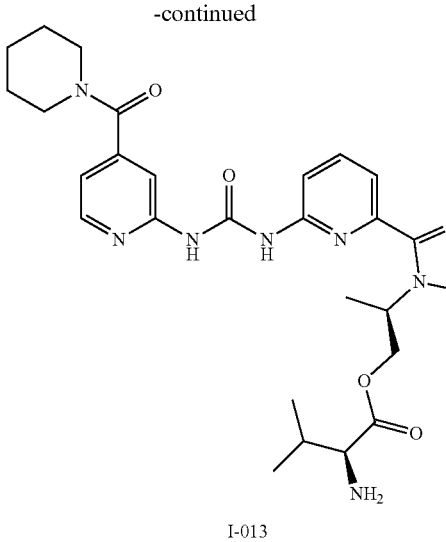

I-013

(2R)-2-[3-[6-([[4-(Piperidine-1-carbonyl)pyridin-2-yl]carbamoyl]amino)pyridin-2-yl]-4H-1,2,4-triazol-4-yl]propyl (2S)-2-([[(9H-fluoren-9-yl)methoxy]carbonyl]amino)-3-methylbutanoate (Compound 13a)

To a solution of Compound I-110 (398 mg, 0.88 mmol) in DCM (8 mL) was added (2S)-2-([[(9H-fluoren-9-yl)methoxy]carbonyl]amino)-3-methylbutanoic acid (300 mg, 0.88 mmol), DIEA (343 mg, 2.65 mmol) and DMAP (21.6 mg, 0.18 mmol). Then EDC (275 mg, 1.77 mmol) was added to the mixture at 0° C. The resulting mixture was stirred at room temperature for 3 h. The mixture was diluted with H₂O and extracted with dichloromethane. The combined organic layer was washed with brine, dried over anhydrous sodium sulfate and filtered. The filtrate was concentrated under vacuum. The residue was purified by flash column chromatography with DCM/CH₃OH (10/1, v/v) to afford the title compound (350 mg, 68%) as a white solid. LCMS (ESI, m/z): [M+H]+=772.3.

(2R)-2-[3-[6-([[4-(Piperidine-1-carbonyl)pyridin-2-yl]carbamoyl]amino)pyridin-2-yl]-4H-1,2,4-triazol-4-yl]propyl (2S)-2-amino-3-methylbutanoate (Compound I-013)

To a solution of Compound 13a (150 mg, 0.19 mmol) in DCM (3 mL) was added piperidine (82.7 mg, 0.97 mmol). The resulting mixture was stirred at room temperature for 5 h. The mixture was diluted with water and extracted with dichloromethane. The combined organic layer was washed with brine, dried over anhydrous sodium sulfate and filtered. The filtrate was concentrated under vacuum. The residue was purified by Prep-HPLC with the following conditions: Column: XBridge Prep OBD C18 Column 30×150 mm, 5 um; Mobile Phase A: Water (10 mmol/L NH₄HCO₃), Mobile Phase B: ACN; Flow rate: 60 mL/min; Gradient: 19% B to 39% B in 7 min; 254/220 nm; Rt: 6.82 min to afford the title compound (31.6 mg, 30%) as a white solid. LCMS (ESI, m/z): [M+H]+=550.3. ¹H NMR (300 MHz, DMSO-d₆, ppm): δ 10.85 (s, 1H), 10.12 (s, 1H), 8.97 (s, 1H), 8.39-8.37 (m, 1H), 8.08-7.96 (m, 2H), 7.78-7.75 (m, 1H), 7.55 (s, 1H), 7.05-7.03 (m, 1H), 5.80-5.60 (m, 1H), 4.55-4.30 (m, 2H),

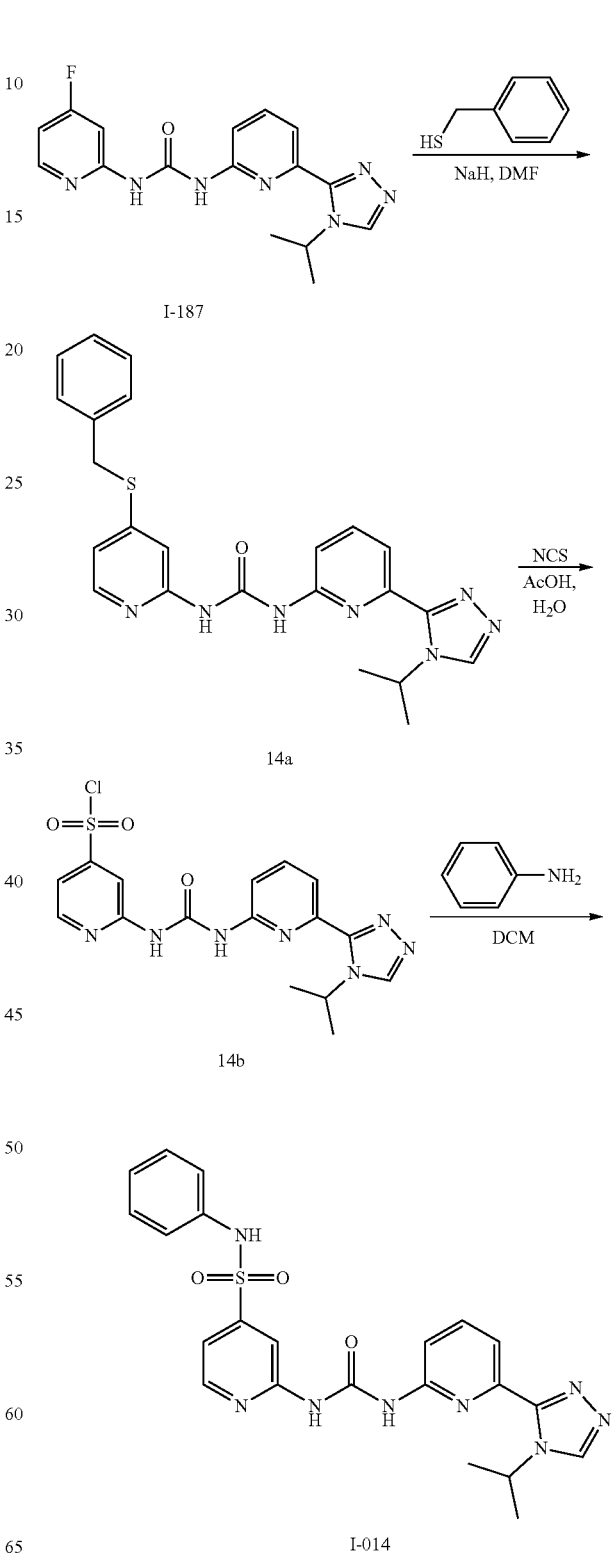

1-[4-(Benzylsulfanyl)pyridin-2-yl]-3-[6-[4-(propan-2-yl)-4H-1,2,4-triazol-3-yl]pyridin-2-yl]urea (Compound 14a)

To a solution of phenyl methanethiol (8.7 g, 70.4 mmol) in DMF (20 mL) was added NaH (2.0 g, 50.0 mmol). The resulting mixture was stirred at 0° C. for 2 h. Then Compound I-187 (4.8 g, 14.1 mmol) was added to the mixture. The reaction mixture was stirred at room temperature for 3 h. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with DCM/MeOH (10/1, v/v) to the title compound (6.0 g, 95%) as a white solid. LCMS (ESI, m/z): $[M+H]^+=446.2$.

2-[([6-[4-(Propan-2-yl)-4H-1,2,4-triazol-3-yl]pyridin-2-yl]carbamoyl)amino]pyridine-4-sulfonyl chloride (Compound 14b)

To a solution of Compound 14a (300 mg, 0.67 mmol) in AcOH (3 mL) and water (1 mL) was added NCS (269 mg, 2.02 mmol). The resulting mixture was stirred at 0° C. for 0.5 h then stirred at room temperature for 2 h. After the reaction was completed, the resulting mixture was diluted with $H_2O$ and extracted with ethyl acetate. The combined organic layer was concentrated under vacuum to afford the title compound (100 mg, crude) as a white solid. LCMS (ESI, m/z): $[M+H]^+=422.1$.

1-[4-(Phenylsulfamoyl)pyridin-2-yl]-3-[6-[4-(propan-2-yl)-4H-1,2,4-triazol-3-yl]pyridin-2-yl]urea (Compound I-014)

To a solution of Compound 14b (100 mg, 0.24 mmol) in DCM (2 mL) was added aniline (2 ml). The resulting mixture was stirred at room temperature for 2 h. After the reaction was completed, the mixture was concentrated under vacuum. The residue was purified by flash column chromatography with DCM/MeOH (10/1, v/v) and then purified by Prep-HPLC with the following conditions: Column: XBridge Prep OBD C18 Column 30×150 mm, 5 um; Mobile Phase A: Water (10 mmol/L $NH_4HCO_3$), Mobile Phase B: ACN; Flow rate: 60 mL/min; Gradient: 24% B to 34% B in 10 min; 254/220 nm; Rt: 10.73 min to afford the title compound (9.5 mg, 8%) as a white solid. LCMS (ESI, m/z): $[M+H]^+=479.2$. $^1H$ NMR (300 MHz, DMSO-$d_6$, ppm): δ 10.36 (s, 1H), 10.25 (s, 1H), 8.90 (s, 1H), 8.43 (d, J=6.0 Hz, 1H), 8.15 (s, 1H), 8.05-7.95 (m, 2H), 7.75 (d, J=6.6 Hz, 1H), 7.29-7.22 (m, 3H), 7.10-7.02 (m, 3H), 5.43-5.37 (m, 1H), 1.50 (d, J=6.9 Hz, 6H).

Example 15: Synthesis of Compound I-015

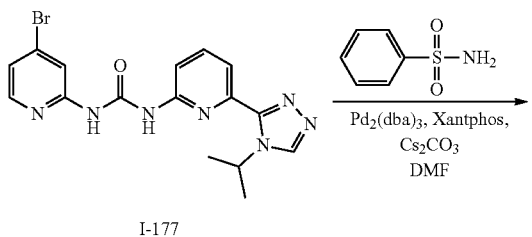

I-177

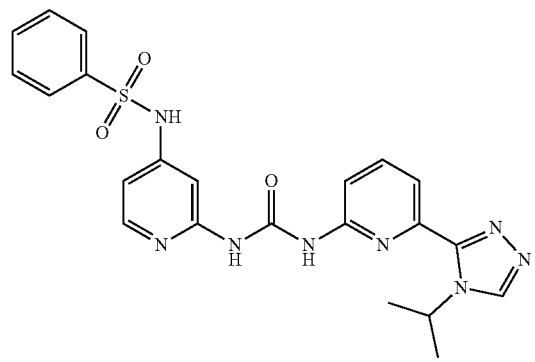

I-015

3-(4-Benzenesulfonamidopyridin-2-yl)-1-[6-[4-(propan-2-yl)-4H-1,2,4-triazol-3-yl]pyridin-2-yl]urea (Compound I-015)

To a mixture of Compound I-177 (100 mg, 0.25 mmol) in DMF (10 mL) was added benzenesulfonamide (46.9 mg, 0.30 mmol), $Cs_2CO_3$ (97.2 mg, 0.30 mmol), $Pd_2(dba)_3$ (25.7 mg, 0.03 mmol) and Xantphos (28.8 mg, 0.05 mmol). The resulting mixture was stirred at 100° C. for 16 h. After the reaction was completed, the mixture was diluted with $H_2O$ and extracted with EtOAc. The combined organic layer was washed with brine, dried over anhydrous $Na_2SO_4$ and filtered. The filtrate was concentrated under vacuum. The residue was purified by Prep-HPLC with the following conditions: Column: XSelect CSH Prep C18 OBD Column, 5 um, 19×150 mm; Mobile Phase A: Water (0.1% FA), Mobile Phase B: ACN; Flow rate: 25 mL/min; Gradient: 18% B to 48% B in 7 min; 254/220 nm; Rt: 6.77 min to afford the title compound (6.8 mg, 6%) as a white solid. LCMS (ESI, m/z): $[M+H]^+=479.2$. $^1H$ NMR (400 MHz, DMSO-$d_6$, ppm): δ 11.20 (s, 1H), 9.91 (s, 1H), 8.89 (s, 1H), 8.06 (d, J=8.0 Hz, 1H), 7.97-7.89 (m, 4H), 7.74-7.72 (m, 1H), 7.67-7.55 (m, 3H), 7.38-7.18 (m, 1H), 6.72-6.65 (m, 1H), 5.43-5.31 (m, 1H), 1.51 (d, J=6.4 Hz, 6H).

Example 16: Synthesis of Compounds I-016 to I-218

Following the procedures described above and substituting the appropriate reagents, starting materials and purification methods known to those skilled in the art, the following compounds of the present invention were prepared.

TABLE 1

| Compound | R₁ | R₂ | LC-MS (M + H)⁺ | ¹HNMR (ppm) |
|---|---|---|---|---|
| I-016 | phenyl-CH(CH₃)- | isopropyl | 323.1 | DMSO-d₆: δ 9.37 (s, 1H), 9.24-9.23 (m, 1H), 8.89-8.88 (m, 1H), 8.01-7.99 (m, 1H), 7.95-7.91 (m, 1H), 7.70-7.69 (m, 1H), 7.51-7.49 (m, 2H), 7.34-7.30 (m, 2H), 7.05-7.01 (m, 1H), 5.48-5.41 (m, 1H), 1.49 (d, J = 6.4 Hz, 6H). |
| I-017 | 4-methylphenyl-CH(CH₃)- | isopropyl | 337.2 | CD₃OD-d₄: δ 9.35 (s, 1H), 8.07-7.95 (m, 2H), 7.74-7.72 (m, 1H), 7.38-7.35 (m, 2H), 7.17-7.14 (m, 2H), 5.65-7.60 (m, 1H), 2.32 (s, 3H), 1.643-1.61 (d, J = 9.0 Hz, 6H). |
| I-018 | 2-fluoro-4-methylphenyl-CH(CH₃)- | isopropyl | 355.2 | DMSO-d₆: δ 9.59 (s, 1H), 9.30 (s, 1H), 8.88 (s, 1H), 8.04-7.90 (m, 3H), 7.71-7.66 (m, 1H), 7.11-7.07 (m, 1H), 7.00-6.97 (m, 1H), 5.42-5.33 (m, 1H), 2.28 (s, 3H), 1.48-1.46 (d, J = 6.6 Hz, 6H). |
| I-019 | 5-bromo-2-fluoro-4-methylphenyl-CH(CH₃)- | isopropyl | 433.2 | DMSO-d₆: δ 9.67 (s, 1H), 9.49 (s, 1H), 8.89 (s, 1H), 8.45 (d, J = 7.5 Hz, 1H), 7.97-7.95 (m, 2H), 7.71-7.68 (m, 1H), 7.37 (d, J = 12.0 Hz, 1H), 5.45-5.25 (m, 1H), 2.30 (s, 3H), 1.48 (d, J = 6.9 Hz, 6H). |
| I-020 | 5-(4-cyclopropyl-1H-imidazol-1-yl)-2-fluoro-4-methylphenyl-CH(CH₃)- | isopropyl | 461.4 | DMSO-d₆: δ 9.76 (s, 1H), 9.64 (s, 1H), 8.89 (s, 1H), 8.19-8.17 (m, 2H), 7.95-7.91 (m, 2H), 7.73-7.70 (m, 1H), 7.43-7.32 (m, 2H), 5.43-5.36 (m, 1H), 2.12 (s, 3H), 1.95-1.92 (m, 1H), 1.49 (d, J = 6.9 Hz, 6H), 0.91-0.86 (m, 2H), 0.83-0.75 (m, 2H). |
| I-021 | 2-methoxyphenyl-CH(CH₃)- | isopropyl | 353.2 | DMSO-d₆: δ 9.88 (s, 1H), 9.73 (s, 1H), 8.90 (s, 1H), 8.18-8.15 (m, 1H), 7.95-7.91 (m, 1H), 7.79-7.77 (m, 1H), 7.60-7.57 (m, 1H), 7.02-6.98 (m, 2H), 6.93-6.89 (m, 1H), 5.22-5.19 (m, 1H), 3.63 (s, 3H) 1.41 (d, J = 6.8 Hz, 6H). |

TABLE 1-continued

| Compound | R₁ | R₂ | LC-MS (M + H)⁺ | ¹HNMR (ppm) |
|---|---|---|---|---|
| I-022 | 4-methoxy-3-biphenyl (attached via CH(CH₃)) | isopropyl | 429.2 | DMSO-d₆: δ 9.94 (s, 1H), 9.82 (s, 1H), 8.92 (s, 1H), 8.54 (d, J = 2.4 Hz, 1H), 7.97-7.92 (m, 1H), 7.85-7.82 (m, 1H), 7.62-7.58 (m, 3H), 7.49-7.44 (m, 2H), 7.36-7.28 (m, 2H), 7.10 (d, J = 8.4 Hz, 1H), 5.28-5.19 (m, 1H), 3.70 (s, 3H), 1.44 (d, J = 6.6 Hz, 6H). |
| I-023 | 4-methoxy-3-(piperazin-1-yl)phenyl (attached via CH(CH₃)) | isopropyl | 437.4 | CD₃OD-d₄: δ 8.87 (s, 1H), 8.02 (d, J = 2.8 Hz, 1H), 7.95-7.91 (m, 1H), 7.64 (d, J = 8.4 Hz, 1H), 7.57 (d, J = 7.2 Hz, 1H), 6.86 (d, J = 8.8 Hz, 1H), 6.65-6.62 (m, 1H), 5.29-5.22 (m, 1H), 3.54 (s, 3H), 3.09-3.06 (m, 4H), 3.02-2.99 (m, 4H), 1.47 (d, J = 6.8 Hz, 6H). |
| I-024 | 3-carbamoyl-4-methoxyphenyl (attached via CH(CH₃)) | isopropyl | 396.2 | DMSO-d₆: δ 9.85 (s, 1H), 9.75 (s, 1H), 8.84 (s, 1H), 8.60 (s, 1H), 7.98-7.86 (m, 1H), 7.73-7.68 (m, 2H), 7.53-7.47 (m, 2H), 7.10 (s, 1H), 6.97 (d, J = 8.8 Hz, 1H), 5.14-5.10 (m, 1H), 3.61 (s, 3H), 1.34 (d, J = 6.4 Hz, 6H). |
| I-025 | pyridin-2-yl (attached via CH(CH₃)) | isopropyl | 324.3 | DMSO-d₆: δ 11.15 (s, 1H), 9.98 (s, 1H), 8.90 (s, 1H), 8.26-8.25 (m, 1H), 8.08-8.06 (d, J = 8.0 Hz, 1H), 7.98-7.94 (m, 1H), 7.82-7.74 (m, 2H), 7.55-7.52 (d, J = 12.0 Hz, 1H), 7.09-7.05 (m, 1H), 5.43-5.36 (m, 1H), 1.55-1.53 (d, J = 8.0 Hz, 6H). |
| I-026 | pyridin-2-yl (attached via CH(CH₃)) | 1-hydroxy-3-methylbutan-2-yl | 340.1 | DMSO-d₆: δ 11.15 (s, 1H), 9.97 (s, 1H), 8.79 (s, 1H), 8.28 (d, J = 4.0 Hz, 1H), 8.06 (d, J = 8.0 Hz, 1H), 7.98-7.94 (m, 1H), 7.82-7.73 (m, 2H), 7.55-7.52 (m, 1H), 7.08-7.05 (m, 1H), 5.35-5.32 (m, 1H), 5.06-5.03 (m, 1H), 3.74-3.71 (m, 2H), 1.51 (d, J = 6.8 Hz, 3H). |
| I-027 | pyridin-2-yl (attached via CH(CH₃)) | 1-hydroxypropan-2-yl | 340.2 | DMSO-d₆: δ 11.09 (s, 1H), 10.08 (s, 1H), 8.95 (s, 1H), 8.29-8.27 (m, 1H), 8.08 (d, J = 8.4 Hz, 1H), 7.99-7.95 (m, 1H), 7.83-7.74 (m, 2H), 7.55-7.53 (m, 1H), 7.09-7.06 (m, 1H), 5.38-5.20 (m, 2H), 3.78-3.70 (m, 2H), 1.53 (d, J = 6.8 Hz, 3H). |

TABLE 1-continued

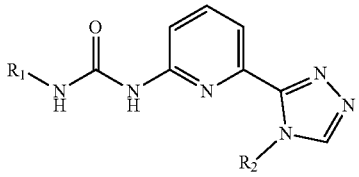

| Compound | R₁ | R₂ | LC-MS (M + H)⁺ | ¹HNMR (ppm) |
|---|---|---|---|---|
| I-028 | 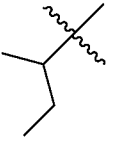 [SMILES: *C(C)CC] | 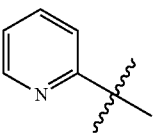 [SMILES: *c1ccccn1] | 338.2 | DMSO-d₆: δ 11.16 (s, 1H), 10.01 (s, 1H), 8.89 (s, 1H), 8.26-8.25 (m, 1H), 8.08 (d, J = 8.0 Hz, 1H), 7.98-7.94 (m, 1H) 7.82-7.74 (m, 2H), 7.53-7.50 (m, 1H), 7.09-7.06 (m, 1H), 5.32-5.23 (m, 1H), 1.94-1.82 (m, 2H), 1.53 (d, J = 6.8 Hz, 3H), 0.81-0.77 (m, 3H). |
| I-029 | 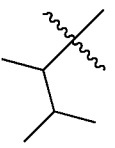 [SMILES: *C(C)C(C)C] | 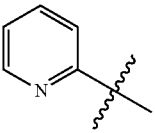 [SMILES: *c1ccccn1] | 353.2 | DMSO-d₆: δ 11.15 (s, 1H), 10.03 (s, 1H), 8.88 (s, 1H), 8.26-8.25 (m, 1H), 8.08 (d, J = 8.0 Hz, 1H), 7.98-7.94 (m, 1H), 7.82-7.74 (m, 2H), 7.52-7.49 (m, 1H), 7.09-7.06 (m, 1H), 5.26-5.18 (m, 1H), 2.10-2.02 (m, 1H), 1.52 (d, J = 6.8 Hz, 3H), 0.92-0.88 (m, 3H), 0.73 (d, J = 6.8 Hz, 3H). |
| I-030 | 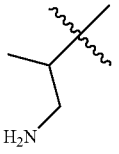 [SMILES: *C(C)CN] | 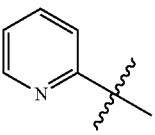 | 339.2 | DMSO-d₆: δ 11.15 (s, 1H), 10.00 (s, 1H), 8.82-8.80 (m, 1H), 8.30-8.26 (m, 1H), 8.08-8.04 (m, 1H), 7.98-7.92 (m, 1H), 7.82-7.70 (m, 2H), 7.59-7.53 (m, 1H), 7.08-7.03 (m, 1H), 5.21-5.16 (m, 1H), 3.42-3.37 (m, 2H), 2.98-2.93 (m, 2H), 1.51 (d, J = 6.8 Hz, 3H). |
| I-031 | 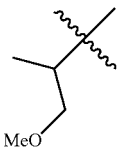 | 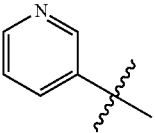 [SMILES: *c1cccnc1] | 354.2 | DMSO-d₆: δ 11.12 (s, 1H), 9.97 (s, 1H), 8.84 (s, 1H), 8.28-8.27 (m, 1H), 8.09-8.06 (m, 1H), 7.98-7.94 (m, 1H), 7.82-7.75 (m, 2H), 7.54 (d, J = 8.0 Hz, 1H), 7.09-7.06 (m, 1H), 5.59-5.54 (m, 1H), 3.76-3.72 (m, 1H), 3.67-3.63 (m, 1H), 3.19 (s, 3H), 1.54 (d, J = 6.8 Hz, 3H). |
| I-032 | 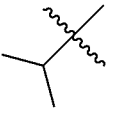 [SMILES: *C(C)C] | 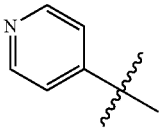 | 324.2 | DMSO-d₆: δ 9.54 (s, 1H), 9.38 (s, 1H), 8.88-8.87 (m, 1H), 8.65-8.64 (m, 1H), 8.25-8.23 (m, 1H), 8.01-7.92 (m, 3H), 7.72-7.70 (m, 1H), 7.37-7.34 (m, 1H), 5.48-5.44 (m, 1H), 1.48 (d, J = 6.8 Hz, 6H). |
| I-033 | 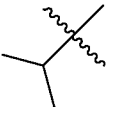 [SMILES: *C(C)C] | 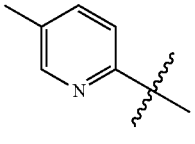 [SMILES: *c1ccc(C)cn1] | 324.2 | DMSO-d₆: δ 9.63-9.40 (m, 2H), 8.90 (s, 1H), 8.42-8.40 (m, 2H), 8.02-7.94 (m, 2H), 7.75-7.73 (m, 1H), 7.49-7.47 (m, 2H), 5.50-5.43 (m, 1H), 1.49 (d, J = 6.8 Hz, 6H). |
| I-034 | 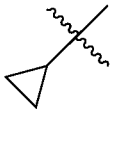 | 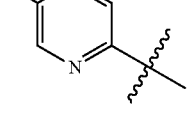 | 336.2 | DMSO-d₆: δ 10.79 (s, 1H), 10.21 (s, 1H), 8.71 (s, 1H), 8.09 (s, 1H), 7.98-7.94 (m, 2H), 7.75-7.73 (d, J = 8.0 Hz, 1H), 7.64-7.60 (m, 2H), 4.08-4.03 (m, 1H), 2.24 (s, 3H), 1.10-1.04 (m, 2H), 1.01-0.97 (m, 2H). |
| I-035 | 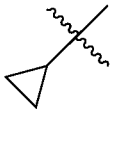 | 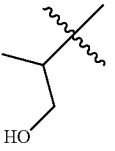 [SMILES: *C(C)CO] | 354.2 | DMSO-d₆: δ 11.10 (s, 1H), 9.88 (s, 1H), 8.79 (s, 1H), 8.10-8.04 (m, 2H), 7.97-7.93 (m, 1H), 7.73 (d, J = 6.8 Hz, 1H), 7.64-7.61 (m, 1H), 7.45 (d, J = 8.4 Hz, 1H), 5.35-5.30 (m, 1H), 5.06-5.03 (m, 1H), 3.75-3.70 (m, 2H), 2.25 (s, 3H), 1.52 (d, J = 6.8 Hz, 3H). |

TABLE 1-continued

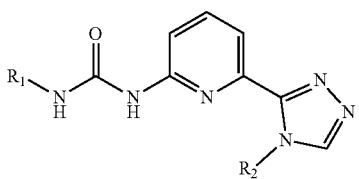

| Compound | R₁ | R₂ | LC-MS (M + H)⁺ | ¹HNMR (ppm) |
|---|---|---|---|---|
| I-036 | 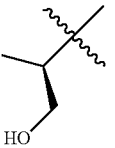 [SMILES: *[C@H](C)CO] | 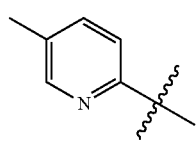 [SMILES: *c1ccc(C)cn1] | 354.1 | DMSO-d₆: δ 11.09 (s, 1H), 9.90 (s, 1H), 8.80 (s, 1H), 8.13-8.02 (m, 2H), 7.97-7.93 (m, 1H), 7.72 (d, J = 7.2 Hz, 1H), 7.64-7.61 (m, 1H), 7.44 (d, J = 8.0 Hz, 1H), 5.35-5.30 (m, 1H), 5.07-5.04 (m, 1H), 3.74-3.71 (m, 2H), 2.25 (s, 3H), 1.52 (d, J = 6.8 Hz, 3H). |
| I-037 | 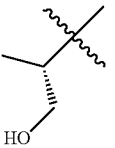 [SMILES: *[C@@H](C)CO] | 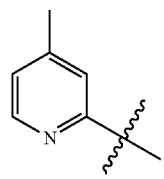 [SMILES: *c1cc(C)ccn1] | 354.2 | DMSO-d₆: δ 11.09 (s, 1H), 9.88 (s, 1H), 8.79 (s, 1H), 8.10 (s, 1H), 8.05 (d, J = 8.0 Hz, 1H), 7.97-7.93 (m, 1H), 7.73 (d, J = 6.8 Hz, 1H), 7.64-7.62 (m, 1H), 7.46-7.44 (m, 1H), 5.35-5.29 (m, 1H), 5.06-5.03 (m, 1H), 3.76-3.70 (m, 2H), 2.25 (s, 3H), 1.52 (d, J = 6.8 Hz, 3H). |
| I-038 |  | 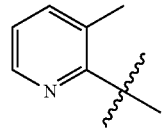 | 338.1 | CD₃OD-d₄: δ 8.86 (s, 1H), 8.16-8.11 (m, 2H), 7.98-7.94 (m, 1H), 7.78-7.76 (m, 1H), 7.14 (s, 1H), 6.93-6.92 (m, 1H), 5.56-5.50 (m, 1H), 2.37 (s, 3H), 1.65-1.64 (d, J = 6.8 Hz, 6H). |
| I-039 | 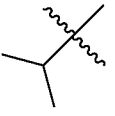 | 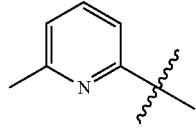 [SMILES: *c1cccc(C)n1] | 338.0 | DMSO-d₆: δ 12.50 (s, 1H), 8.95 (s, 1H), 8.91 (s, 1H), 8.15 (d, J = 8.8 Hz, 2H), 8.00-7.96 (m, 1H), 7.79 (d, J = 7.2 Hz, 1H), 7.69 (d, J = 7.2 Hz, 1H), 7.09-7.06 (m, 1H), 5.43-5.36 (m, 1H), 2.23 (s, 3H), 1.58 (d, J = 6.4 Hz, 6H). |
| I-040 |  | 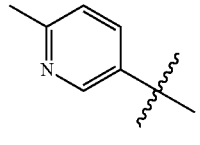 [SMILES: *c1ccc(C)nc1] | 338.1 | DMSO-d₆: δ 9.71 (s, 1H), 8.21-8.19 (m, 1H), 8.08-8.04 (m, 1H), 7.84-7.78 (m, 2H), 7.40-7.39 (m, 1H), 7.03-7.01 (m, 1H), 5.68-5.61 (m, 1H), 2.51-2.49 (m, 3H), 1.56 (d, J = 6.4 Hz, 6H). |
| I-041 |  | 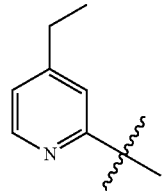 [SMILES: *c1cc(CC)ccn1] | 338.3 | DMSO-d₆: δ 10.78 (s, 1H), 10.04 (s, 1H), 9.14 (s, 1H), 8.99-8.98 (d, J = 4.0 Hz, 1H), 8.28-8.26 (m, 1H), 8.01-7.99 (d, J = 8.0 Hz, 2H), 7.85-7.77 (m, 2H), 5.56 (s, 1H), 2.67 (s, 3H), 1.51-1.49 (m, 6H). |
| I-042 | 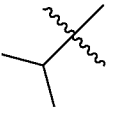 [SMILES: *C(C)C] | 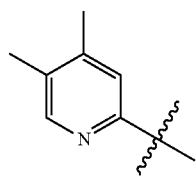 [SMILES: *c1cc(C)c(C)cn1] | 352.2 | DMSO-d₆: δ 11.30 (s, 1H), 9.91 (s, 1H), 8.89 (s, 1H), 8.14 (d, J = 5.2 Hz, 1H), 8.08 (d, J = 8.0 Hz, 1H), 7.97-7.93 (m, 1H), 7.74 (d, J = 7.2 Hz, 1H), 7.37 (s, 1H), 6.94 (d, J = 4.8 Hz, 1H), 5.43-5.36 (m, 1H), 2.67-2.59 (m, 2H), 1.54 (d, J = 6.8 Hz, 6H), 1.21-1.17 (m, 3H). |
| I-043 | 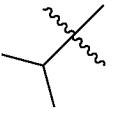 [SMILES: *C(C)C] |  | 352.1 | DMSO-d₆: δ 9.83 (s, 1H), 8.89 (s, 1H), 8.08-8.06 (d, J = 8.0 Hz, 1H), 7.97-7.95 (m, 2H), 7.94-7.92 (d, J = 8.0 Hz, 1H), 7.31 (s, 1H), 5.41-5.37 (m, 1H), 2.24 (s, 3H), 2.17 (s, 3H), 1.55-1.53 (d, J = 8.0 Hz, 6H). |

TABLE 1-continued
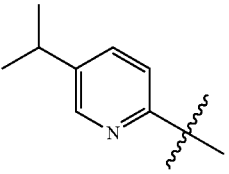 [SMILES: *c1ccc(C(C)C)cn1]
| Compound | R₁ | R₂ | LC-MS (M + H)⁺ | ¹HNMR (ppm) |
|---|---|---|---|---|
| I-044 |  | 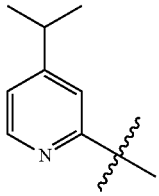 [SMILES: *c1cc(C(C)C)ccn1] | 366.3 | DMSO-d₆: δ 11.00 (s, 1H), 9.90 (s, 1H), 8.90 (s, 1H), 8.13 (s, 1H), 8.08-8.06 (m, 1H), 7.98-7.94 (m, 1H), 7.75-7.71 (m, 2H), 7.52-7.50 (m, 1H), 5.43-5.36 (m, 1H), 2.95-2.88 (m, 1H), 1.54 (d, J = 6.8 Hz, 6H), 1.22 (d, J = 6.8 Hz, 6H). |
| I-045 |  | 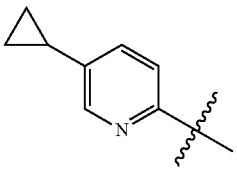 [SMILES: *c1ccc(C2CC2)cn1] | 366.2 | DMSO-d₆: δ 11.28 (s, 1H), 9.90 (s, 1H), 8.89 (s, 1H), 8.15 (d, J = 5.2 Hz, 1H), 8.08 (d, J = 8.0 Hz, 1H), 7.97-7.93 (m, 1H), 7.74 (d, J = 6.8 Hz, 1H), 7.40 (s, 1H), 6.99-6.97 (m, 1H), 5.43-5.36 (m, 1H), 2.91-2.84 (m, 1H), 1.54 (d, J = 6.8 Hz, 6H), 1.21 (d, J = 6.8 Hz, 6H). |
| I-046 |  | 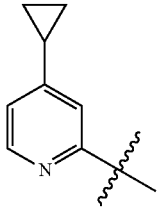 [SMILES: *c1cc(C2CC2)ccn1] | 364.0 | DMSO-d₆: δ 10.96 (s, 1H), 9.88 (s, 1H), 8.90 (s, 1H), 8.08-8.04 (m, 2H), 7.98-7.92 (m, 1H), 7.74-7.72 (m, 1H), 7.45 (s, 2H), 5.40-5.36 (m, 1H), 1.97-1.90 (m, 1H), 1.54 (d, J = 6.8 Hz, 6H), 0.96-0.94 (m, 2H), 0.69-0.67 (m, 2H). |
| I-047 |  | 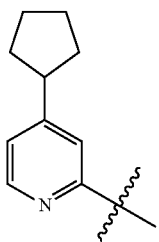 [SMILES: *c1cc(C2CCCC2)ccn1] | 364.2 | DMSO-d₆: δ 11.30 (s, 1H), 9.85 (s, 1H), 8.89 (s, 1H), 8.09-8.06 (m, 2H), 7.97-7.93 (m, 1H), 7.75-7.73 (m, 1H), 7.23 (s, 1H), 6.76-6.75 (m, 1H), 5.42-5.35 (m, 1H), 1.96-1.90 (m, 1H), 1.53 (d, J = 6.8 Hz, 6H), 1.11-1.06 (m, 2H), 0.79-0.72 (m, 2H). |
| I-048 | 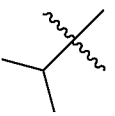 | 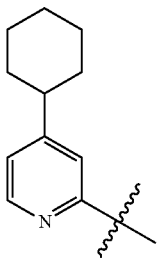 [SMILES: *c1cc(C2CCCCC2)ccn1] | 392.3 | DMSO-d₆: δ 9.92 (s, 1H), 8.90 (s, 1H), 8.14-8.13 (m, 1H), 8.09-8.07 (m, 1H), 7.97-7.93 (m, 1H), 7.75-7.73 (m, 1H), 7.40 (s, 1H), 6.97 (d, J = 5.6 Hz, 1H), 5.42-5.36 (m, 1H), 3.02-2.94 (s, 1H), 2.07-2.03 (m, 2H), 1.77-1.74 (m, 2H), 1.72-1.66 (m, 2H), 1.55-1.53 (m, 8H). |
| I-049 | 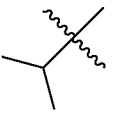 [SMILES: *C(C)C] |  | 406.2 | CD₃OD-d₄: δ 8.85 (s, 1H), 8.15-8.12 (m, 2H), 7.97-7.93 (m, 1H), 7.75 (d, J = 7.6 Hz, 1H), 7.15 (s, 1H), 6.95 (d, J = 5.2 Hz, 1H), 5.55-5.48 (m, 1H), 2.60-2.45 (m, 1H), 1.89-1.87 (m, 4H), 1.80-1.73 (m, 1H), 1.63 (d, J = 6.8 Hz, 6H), 1.49-1.40 (m, 4H), 1.33-1.28 (m, 1H). |

TABLE 1-continued
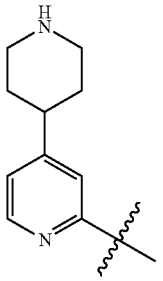 [SMILES: *c1cc(C2CCNCC2)ccn1]
| Compound | R₁ | R₂ | LC-MS (M + H)⁺ | ¹HNMR (ppm) |
|---|---|---|---|---|
| I-050 |  | 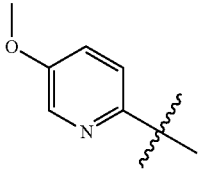 [SMILES: *c1ccc(OC)cn1] | 407.2 | DMSO-d₆: δ 11.23 (s, 1H), 9.98 (s, 1H), 8.89 (s, 1H), 8.36 (s, 1H), 8.17 (d, J = 5.2 Hz, 1H), 8.08-8.06 (m, 1H), 7.97-7.93 (m, 1H), 7.75-7.74 (m, 1H), 7.43 (s, 1H), 6.95 (d, J = 4.8 Hz, 1H), 5.43-5.36 (m, 1H), 3.26-3.20 (m, 2H), 2.80-2.58 (m, 3H), 1.83-1.80 (m, 2H), 1.67-1.59 (m, 2H), 1.53 (d, J = 6.8 Hz, 6H). |
| I-051 | 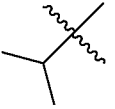 [SMILES: *C(C)C] | 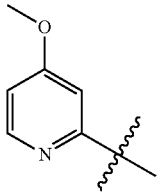 [SMILES: *c1cc(OC)ccn1] | 354.2 | DMSO-d₆: δ 10.74 (s, 1H), 10.11 (s, 1H), 9.67 (s, 1H), 8.15-8.13 (d, J = 8.0 Hz, 1H), 8.04-7.96 (m, 2H), 7.78-7.77 (m, 1H), 7.67-7.64 (m, 1H), 7.55-7.52 (m, 1H), 5.56-5.53 (m, 1H), 3.81 (s, 3H), 1.58-1.56 (d, J = 8.0 Hz, 6H). |
| I-052 |  | 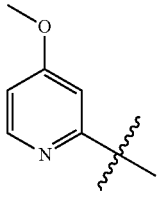 [SMILES: *c1cc(OC)ccn1] | 354.2 | DMSO-d₆: δ 11.33 (s, 1H), 9.90 (s, 1H), 8.90 (s, 1H), 8.09-8.07 (m, 2H), 7.98-7.94 (s, 1H), 7.76-7.74 (d, J = 8.0 Hz, 1H), 7.08 (s, 1H), 6.70-6.69 (m, 1H), 5.76 (s, 1H), 3.83 (s, 3H), 1.55-1.53 (d, J = 8.0 Hz, 6H). |
| I-053 | 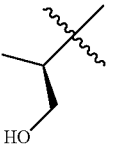 [SMILES: *[C@H](C)CO] | 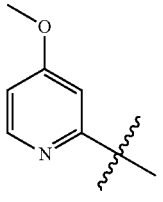 [SMILES: *c1cc(OC)ccn1] | 370.1 | DMSO-d₆: δ 11.30 (s, 1H), 9.88 (s, 1H), 8.79 (s, 1H), 8.10-8.05 (m, 2H), 7.97-7.93 (m, 1H), 7.74 (d, J = 7.6 Hz, 1H), 7.07 (s, 1H), 6.70-6.68 (m, 1H), 5.35-5.31 (m, 1H), 5.06-5.03 (m, 1H), 3.83 (s, 3H), 3.74-3.72 (m, 2H), 1.51 (d, J = 6.8 Hz, 3H). |
| I-054 | 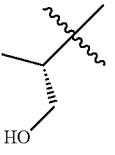 [SMILES: *[C@@H](C)CO] | 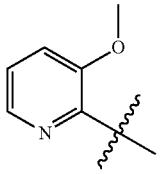 [SMILES: *c1ncccc1OC] | 370.2 | DMSO-d₆: δ 11.19 (s, 1H), 9.89 (s, 1H), 8.79 (s, 1H), 8.10-8.05 (m, 2H), 7.97-7.93 (m, 1H), 7.74 (d, J = 6.8 Hz, 1H), 7.08 (s, 1H), 6.70-6.08 (m, 1H), 5.35-5.31 (m, 1H), 5.07-5.04 (m, 1H), 3.83 (s, 3H), 3.74-3.72 (m, 2H), 1.51 (d, J = 6.8 Hz, 3H). |
| I-055 | 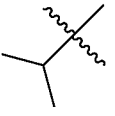 [SMILES: *C(C)C] | | 354.2 | DMSO-d₆: δ 12.48 (s, 1H), 8.99 (s, 1H), 8.65 (s, 1H), 8.13 (d, J = 8.0 Hz, 1H), 8.01-7.97 (m, 1H), 7.86-7.74 (m, 2H), 7.48 (d, J = 7.2 Hz, 1H), 7.12 (s, 1H), 5.46-5.38 (m, 1H), 3.98 (s, 3H), 1.58 (d, J = 6.0 Hz, 6H). |

TABLE 1-continued
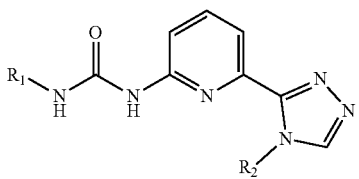
| Compound | R₁ | R₂ | LC-MS (M + H)⁺ | ¹HNMR (ppm) |
|---|---|---|---|---|
| I-056 | 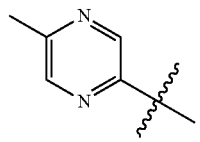 [SMILES: *c1cnc(C)cn1] | 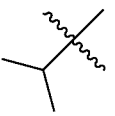 [SMILES: *C(C)C] | 339.1 | CD₃OD-d₄: δ 8.89-8.77 (m, 2H), 8.20 (s, 1H), 8.08-8.05 (m, 1H), 8.00-7.94 (m, 1H), 7.77-7.74 (m, 1H), 5.55-7.46 (m, 1H), 2.51 (s, 3H), 1.63-1.53 (d, J = 6.0 Hz, 6H). |
| I-057 | 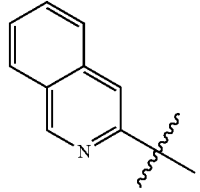 [SMILES: *c1cc2ccccc2cn1] |  | 374.4 | DMSO-d₆: δ 10.06 (s, 1H), 9.13 (s, 1H), 8.91 (s, 1H), 8.23-8.22 (m, 1H), 8.07-8.04 (m, 2H), 7.99-7.97 (m, 1H), 7.95-7.94 (m, 1H), 7.91-7.89 (m, 1H), 7.73-7.70 (m, 2H), 7.51-7.49 (m, 1H), 5.45-5.42 (m, 1H), 1.53 (d, J = 6.8 Hz, 6H). |
| I-058 | 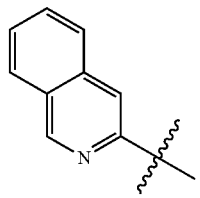 [SMILES: *c1cc2ccccc2cn1] |  | 390.1 | DMSO-d₆: δ 10.07 (s, 1H), 10.02 (s, 1H), 9.13 (s, 1H), 8.81 (s, 1H), 8.22 (s, 1H), 8.07-8.02 (m, 2H), 7.99-7.94 (m, 1H), 7.91-7.89 (m, 1H), 7.74-7.68 (m, 2H), 7.54-7.48 (m, 1H), 5.38-5.32 (m, 1H), 5.06-5.02 (m, 1H), 3.72-3.68 (m, 2H), 1.53 (d, J = 6.9 Hz, 3H). |
| I-059 | 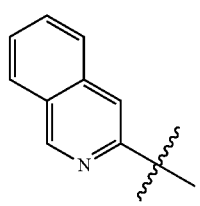 [SMILES: *c1cc2ccccc2cn1] | 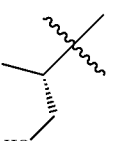 | 390.2 | DMSO-d₆: δ 10.07-10.04 (m, 2H), 9.13 (s, 1H), 8.80 (s, 1H), 8.22 (s, 1H), 8.06-8.02 (m, 2H), 7.98-7.94 (m, 1H), 7.91-7.89 (m, 1H), 7.72-7.69 (m, 2H), 7.53-7.49 (m, 1H), 5.37-5.34 (m, 1H), 5.06-5.03 (m, 1H), 3.71-3.69 (m, 2H), 1.52 (d, J = 6.8 Hz, 3H). |
| I-060 | 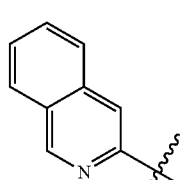 | 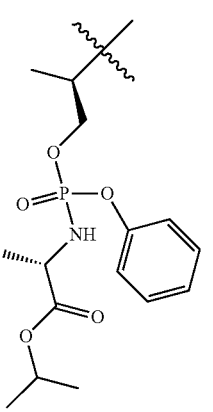 [SMILES: *[C@H](C)COP(=O)(N[C@@H](C)C(=O)OC(C)C)Oc1ccccc1] | 659.2 | DMSO-d₆: δ 10.15 (s, 1H), 9.88 and 9.81 (s, total 1H), 9.15 and 9.13 (s, total 1H), 8.88 and 8.80 (s, total 1H), 8.19 (s, 1H), 8.07-8.02 (m, 2H), 7.97-7.88 (m, 2H), 7.78-7.68 (m, 2H), 7.52-7.45 (m, 1H), 7.33-7.28 (m, 1H), 7.27-7.21 (m, 1H), 7.16-6.98 (m, 3H), 6.09-6.03 (m, 1H), 5.75-5.50 (m, 1H), 4.80-4.75 (m, 1H), 4.45-4.27 (m, 2H), 3.66-3.64 (m, 1H), 1.65-1.57 (m, 3H), 1.12-1.06 (m, 9H). |
| I-061 | 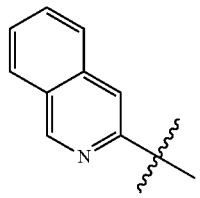 [SMILES: *c1cc2ccccc2cn1] | 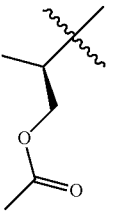 [SMILES: *[C@H](C)COC(C)=O] | 432.2 | DMSO-d₆: δ 10.06 (s, 2H), 9.14 (s, 1H), 8.95 (s, 1H), 8.23 (s, 1H), 8.07-7.96 (m, 3H), 7.91 (d, J = 8.1 Hz, 1H), 7.76-7.69 (m, 2H), 7.54-7.49 (m, 1H), 5.71-5.65 (m, 1H), 4.44-4.27 (m, 2H), 1.83 (s, 3H), 1.63 (d, J = 6.9 Hz, 3H). |

TABLE 1-continued

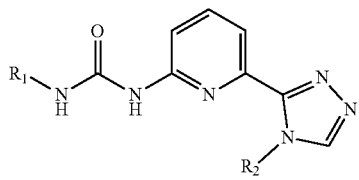

| Compound | R₁ | R₂ | LC-MS (M + H)⁺ | ¹HNMR (ppm) |
|---|---|---|---|---|
| I-062 | isoquinolin-3-yl | valine isobutyl ester group | 489.4 | DMSO-d₆: δ 10.11 (s, 1H), 10.05 (s, 1H), 9.15 (s, 1H), 8.98 (s, 1H), 8.20 (d, J = 10.0 Hz, 1H), 8.06 (d, J = 8.4 Hz, 2H), 8.05-7.97 (m, 1H), 7.92-7.89 (m, 1H), 7.76-7.70 (m, 2H), 7.54-7.50 (m, 1H), 5.75-5.72 (m, 1H), 4.48-4.44 (m, 1H), 4.39-4.34 (m, 1H), 3.00 (d, J = 5.2 Hz, 1H), 1.65 (d, J = 7.2 Hz, 3H), 1.57-1.53 (m, 1H), 0.68 (d, J = 6.8 Hz, 3H), 0.60 (d, J = 6.8 Hz, 3H). |
| I-063 | isoquinolin-3-yl | 2,2-dimethylbutanoate ester | 488.2 | DMSO-d₆: δ 10.08 (s, 1H), 10.01 (s, 1H), 9.14 (s, 1H), 8.94 (s, 1H), 8.20 (s, 1H), 8.07-7.88 (m, 4H), 7.77-7.68 (m, 2H), 7.53-7.48 (m, 1H), 5.83-5.76 (m, 1H), 4.39-4.31 (m, 2H), 1.64 (d, J = 6.9 Hz, 3H), 1.29-1.24 (m, 2H), 0.90 (s, 6H), 0.58-0.50 (m, 3H). |
| I-064 | isoquinolin-3-yl | heptanoate ester | 502.3 | DMSO-d₆: δ 10.04 (s, 2H), 9.14 (s, 1H), 8.94 (s, 1H), 8.22 (s, 1H), 8.07-7.95 (m, 3H), 7.90 (d, J = 7.8 Hz, 1H), 7.76-7.69 (m, 2H), 7.54-7.49 (m, 1H), 5.84-5.69 (m, 1H), 4.50-4.23 (m, 2H), 2.10-1.90 (m, 2H), 1.63 (d, J = 6.9 Hz, 3H), 1.36-1.00 (m, 8H), 0.81-0.76 (m, 3H). |
| I-065 | 6-(piperazin-1-yl)isoquinolin-3-yl | isobutyl | 458.2 | DMSO-d₆: δ 9.69 (s, 1H), 9.05 (s, 1H), 8.92-8.86 (m, 2H), 8.22-8.10 (m, 1H), 8.06-8.02 (m, 1H), 7.91-7.82 (m, 2H), 7.56-7.47 (m, 2H), 7.17-7.07 (m, 1H), 5.55-5.52 (m, 1H), 3.89-3.50 (m, 5H), 2.98-2.95 (m, 3H), 1.56-1.42 (m, 6H). |
| I-066 | isoquinolin-1-yl | isobutyl | 374.1 | DMSO-d₆: δ 13.23 (s, 1H), 10.20 (s, 1H), 8.92 (s, 1H), 8.85-8.72 (m, 1H), 8.22-8.11 (m, 2H), 8.03-7.95 (m, 2H), 7.82-7.62 (m, 3H), 7.55-7.54 (m, 1H), 5.45-5.35 (m, 1H), 1.61 (d, J = 6.0 Hz, 6H). |

TABLE 1-continued

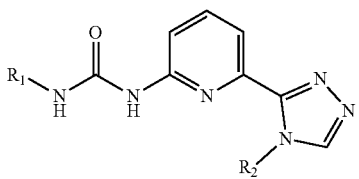

| Compound | R₁ | R₂ | LC-MS (M + H)⁺ | ¹HNMR (ppm) |
|---|---|---|---|---|
| I-067 |  | 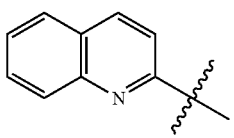 [SMILES: *c1ccc2ccccc2n1] | 374.1 | DMSO-d₆: δ 12.31 (s, 1H), 10.40 (s, 1H), 8.94 (s, 1H), 8.35 (d, J = 8.8 Hz, 1H), 8.21 (d, J = 7.6 Hz, 1H), 8.02-7.98 (m, 1H), 7.93-7.91 (m, 1H), 7.85 (d, J = 7.2 Hz, 1H), 7.78-7.72 (m, 2H), 7.52-7.47 (m, 2H), 5.74-5.68 (m, 1H), 1.57 (d, J = 6.8 Hz, 6H). |
| I-068 | 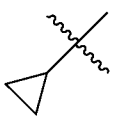 [SMILES: *C1CC1] | 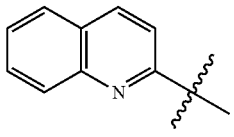 [SMILES: *c1ccc2ccccc2n1] | 372.2 | DMSO-d₆: δ 12.02 (s, 1H), 10.57 (s, 1H), 8.74 (s, 1H), 8.34 (d, J = 8.8 Hz, 1H), 8.10 (d, J = 8.4 Hz, 1H), 8.02-7.98 (m, 1H), 7.92-7.90 (m, 1H), 7.83-7.81 (m, 1H), 7.77-7.73 (m, 1H), 7.62-7.58 (m, 2H), 7.51-7.47 (m, 1H), 4.31-4.25 (m, 1H), 1.11-1.02 (m, 4H). |
| I-069 |  | 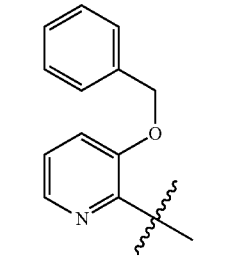 [SMILES: *c1ncccc1OCc1ccccc1] | 390.2 | CD₃OD-d₄: δ 8.87 (s, 1H), 8.29-8.23 (m, 2H), 8.01-7.97 (m, 1H), 7.93-7.90 (m, 1H), 7.86-7.83 (m, 2H), 7.75-7.71 (m, 1H), 7.51-7.47 (m, 1H), 7.27-7.25 (m, 1H), 5.81-5.77 (m, 1H), 3.96-3.92 (m, 1H), 3.88-3.84 (m, 1H), 1.69 (d, J = 6.8 Hz, 3H). |
| I-070 |  | 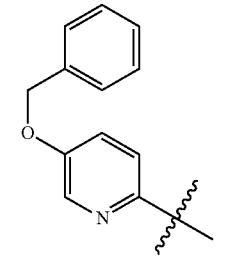 [SMILES: *c1ccc(OCc2ccccc2)cn1] | 430.2 | DMSO-d₆: δ 12.40 (s, 1H), 8.91 (s, 1H), 8.56 (s, 1H), 8.13 (d, J = 8.4 Hz, 1H), 8.00-7.96 (m, 1H), 7.86-7.84 (m, 1H), 7.78 (d, J = 7.6 Hz, 1H), 7.56-7.54 (m, 3H), 7.43-7.33 (m, 3H), 7.10-7.07 (m, 1H), 5.41-5.34 (m, 1H), 5.28 (s, 2H), 1.56 (d, J = 6.8 Hz, 6H). |
| I-071 |  | 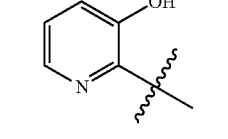 | 430.2 | DMSO-d₆: δ 10.59 (s, 1H), 9.83 (s, 1H), 8.90 (m, 1H), 8.05-8.00 (m, 2H), 7.97-7.93 (m, 1H), 7.72 (d, J = 7.6 Hz, 1H), 7.60-7.55 (m, 2H), 7.48-7.41 (m, 2H), 7.39-7.35 (m, 3H), 5.39-5.36 (m, 1H), 5.17 (s, 2H), 1.51 (d, J = 6.8 Hz, 6H). |
| I-072 |  | 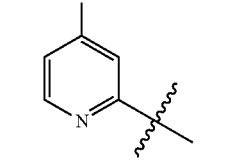 | 340.3 | DMSO-d₆: δ 12.35 (s, 1H), 10.92 (s, 1H), 8.91 (s, 1H), 8.44 (s, 1H), 8.13 (d, J = 8.0 Hz, 1H), 8.00-7.96 (m, 1H), 7.79-7.74 (m, 2H), 7.23-7.21 (m, 1H), 7.01-6.97 (m, 1H), 5.43-5.36 (m, 1H), 1.57 (d, J = 6.8 Hz, 6H). |
| I-073 | 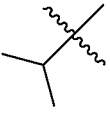 [SMILES: *C(C)C] |  | 340.2 | DMSO-d₆: δ 11.64 (s, 1H), 9.82 (s, 1H), 8.90 (s, 1H), 8.15 (s, 1H), 8.07 (d, J = 8.4 Hz, 1H), 7.97-7.93 (m, 2H), 7.74 (d, J = 6.8 Hz, 1H), 6.86 (s, 1H), 6.50-6.48 (m, 1H), 5.42-5.35 (m, 1H), 1.54 (d, J = 6.8 Hz, 6H). |

TABLE 1-continued
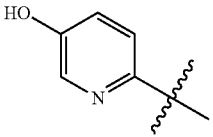 [SMILES: *c1ccc(O)cn1]
| Compound | R₁ | R₂ | LC-MS (M + H)⁺ | ¹HNMR (ppm) |
|---|---|---|---|---|
| I-074 | 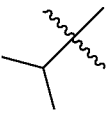 [SMILES: *C(C)C] | 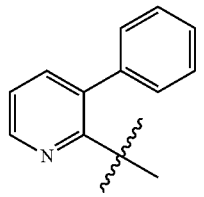 [SMILES: *c1ncccc1-c1ccccc1] | 340.2 | DMSO-d₆: δ 9.73 (s, 1H), 9.61 (d, J = 3.3 Hz, 1H), 8.89 (s, 1H), 8.04 (d, J = 7.8 Hz, 1H), 7.96-7.91 (m, 1H), 7.81 (d, J = 2.4 Hz, 1H), 7.71 (d, J = 7.2 Hz, 1H), 7.41 (s, 1H), 7.27-7.23 (m, 1H), 5.44-5.35 (m, 1H), 1.53 (d, J = 6.6 Hz, 6H). |
| I-075 |  | 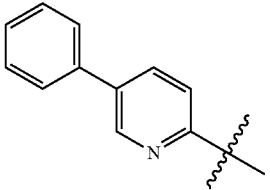 [SMILES: *c1ccc(-c2ccccc2)cn1] | 400.2 | DMSO-d₆: δ 11.86 (s, 1H), 8.90 (s, 1H), 8.36-8.35 (m, 1H), 8.12 (s, 1H), 8.02-7.93 (m, 2H), 7.79-7.75 (m, 2H), 7.67-7.47 (m, 5H), 7.30-7.29 (m, 1H), 5.40-5.37 (m, 1H), 1.56 (d, J = 6.4 Hz, 6H). |
| I-076 | 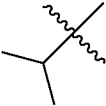 [SMILES: *C(C)C] | 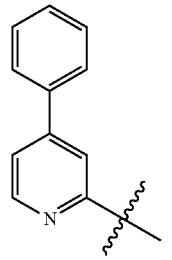 [SMILES: *c1cc(-c2ccccc2)ccn1] | 400.3 | DMSO-d₆: δ 10.80 (s, 1H), 10.08 (s, 1H), 8.90 (s, 1H), 8.57 (s, 1H), 8.14-8.07 (m, 2H), 8.00-7.96 (m, 1H), 7.76-7.69 (m, 4H), 7.51-7.47 (m, 2H), 7.41-7.37 (m, 1H), 5.43-5.37 (m, 1H), 1.55-1.53 (d, J = 8.0 Hz, 6H). |
| I-077 | 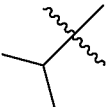 [SMILES: *C(C)C] | 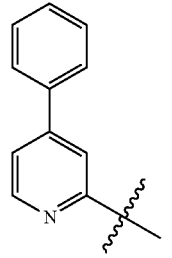 [SMILES: *c1cc(-c2ccccc2)ccn1] | 400.2 | DMSO-d₆: δ 11.07 (brs, 1H), 10.06 (s, 1H), 8.90 (s, 1H), 8.34-8.32 (m, 1H), 8.11-8.09 (m, 1H), 7.99-7.97 (m, 1H), 7.86 (s, 1H), 7.95-7.77 (m, 3H), 7.58-7.51 (m, 3H), 7.40-7.38 (m, 1H), 5.43-5.39 (m, 1H), 1.55 (d, J = 6.8 Hz, 6H). |
| I-078 | 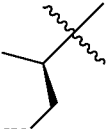 | 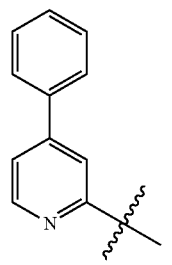 [SMILES: *c1cc(-c2ccccc2)ccn1] | 416.2 | DMSO-d₆: δ 11.15 (s, 1H), 10.06 (s, 1H), 8.81 (s, 1H), 8.35-8.33 (m, 1H) 8.10-8.07 (m, 1H), 7.99-7.93 (m, 1H), 7.86 (s, 1H), 7.76-7.72 (m, 3H), 7.59-7.50 (m, 3H), 7.40-7.38 (m, 1H), 5.35-5.33 (m, 1H), 5.09-5.03 (m, 1H), 3.80-3.70 (m, 2H), 1.53 (d, J = 6.9 Hz, 3H). |
| I-079 | 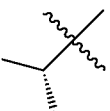 |  | 416.2 | DMSO-d₆: δ 11.10 (s, 1H), 10.06 (s, 1H), 8.80 (s, 1H), 8.34 (d, J = 5.2 Hz, 1H), 8.09 (d, J = 8.4 Hz, 1H), 7.98-7.94 (m, 1H), 7.86 (s, 1H), 7.76-7.73 (m, 3H), 7.58-7.53 (m, 3H), 7.40-7.38 (m, 1H), 5.37-5.33 (m, 1H), 5.08-5.05 (m, 1H), 3.76-3.73 (m, 2H), 1.53 (d, J = 6.8 Hz, 3H). |

TABLE 1-continued
| Compound | R₁ | R₂ | LC-MS (M + H)⁺ | ¹HNMR (ppm) |
|---|---|---|---|---|
| I-080 | 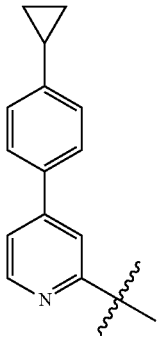 [SMILES: *c1cc(-c2ccc(C3CC3)cc2)ccn1] | 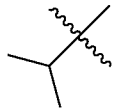 [SMILES: *C(C)C] | 440.3 | DMSO-d₆: δ 11.18 (s, 1H), 10.03 (s, 1H), 8.91 (s, 1H), 8.28 (d, J = 5.6 Hz, 1H), 8.10 (d, J = 8.0 Hz, 1H), 7.99-7.95 (m, 1H), 7.82 (s, 1H), 7.76-7.74 (m, 1H), 7.62 (d, J = 8.4 Hz, 2H), 7.37-7.35 (m, 1H), 7.25 (d, J = 8.4 Hz, 2H), 5.44-5.38 (m, 1H), 2.03-1.96 (m, 1H), 1.55 (d, J = 6.8 Hz, 6H), 1.04-0.99 (m, 2H), 0.77-0.74 (m, 2H). |
| I-081 | 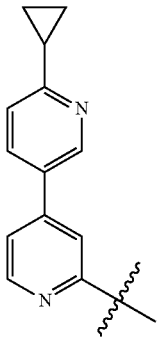 [SMILES: *c1cc(-c2ccc(C3CC3)nc2)ccn1] |  | 441.2 | DMSO-d₆: δ 11.05 (s, 1H), 10.07 (s, 1H), 8.89 (s, 1H), 8.76 (d, J = 2.0 Hz, 1H), 8.33 (d, J = 5.2 Hz, 1H), 8.09-8.07 (m, 1H), 7.99-7.95 (m, 2H), 7.85 (s, 1H), 7.76-7.74 (m, 1H), 7.48-7.46 (m, 1H), 7.42-7.40 (m, 1H), 5.42-5.39 (m, 1H), 2.21-2.17 (m, 1H), 1.54 (d, J = 6.8 Hz, 6H), 1.03-0.98 (m, 4H). |
| I-082 | 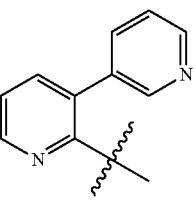 [SMILES: *c1ncccc1-c1cccnc1] |  | 401.2 | DMSO-d₆: δ 11.41 (s, 1H), 8.96 (s, 1H), 8.91 (s, 1H), 8.68-8.65 (m, 1H), 8.61-8.60 (m, 1H), 8.41-8.39 (m, 1H), 7.95-7.90 (m, 3H), 7.85-7.83 (m, 1H), 7.76-7.71 (m, 1H), 7.52-7.48 (m, 1H), 7.34-7.31 (m, 1H), 5.43-5.36 (m, 1H), 1.54 (d, J = 6.8 Hz, 6H). |
| I-083 | 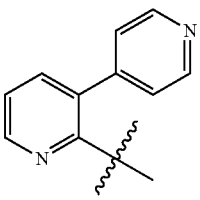 [SMILES: *c1ncccc1-c1ccncc1] |  | 401.2 | DMSO-d₆: δ 11.22 (s, 1H), 9.01 (s, 1H), 8.89 (s, 1H), 8.67-8.65 (m, 2H), 8.43-8.41 (m, 1H), 7.95-7.84 (m, 3H), 7.74-7.72 (m, 1H), 7.54-7.52 (m, 2H), 7.35-7.32 (m, 1H), 5.42-5.36 (m, 1H), 1.54 (d, J = 6.8 Hz, 6H). |
| I-084 | 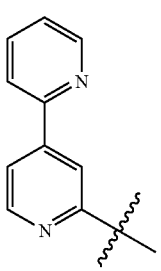 [SMILES: *c1cc(-c2ccccn2)ccn1] |  | 401.2 | DMSO-d₆: δ 11.04 (s, 1H), 10.10 (s, 1H), 8.90 (s, 1H), 8.77 (d, J = 4.0 Hz, 1H), 8.38 (d, J = 5.2 Hz, 1H), 8.33 (s, 1H), 8.10 (d, J = 8.0 Hz, 1H), 8.05-7.95 (m, 3H), 7.77-7.70 (m, 2H), 7.53-7.50 (m, 1H), 5.45-5.39 (m, 1H), 1.55 (d, J = 6.8 Hz, 6H). |

TABLE 1-continued

| Compound | R₁ | R₂ | LC-MS (M + H)⁺ | ¹HNMR (ppm) |
|---|---|---|---|---|
| I-085 | 2,4'-bipyridine | CH(CH₃)CH₂OH | 417.2 | CD₃OD-d₄: δ 8.85 (s, 1H), 8.73-8.71 (m, 1H), 8.42 (d, J = 5.6 Hz, 1H), 8.14 (d, J = 8.4 Hz, 1H), 7.99-7.95 (m, 4H), 7.78 (d, J = 7.2 Hz, 1H), 7.67-7.66 (m, 1H), 7.51-7.48 (m, 1H), 5.55-5.50 (m, 1H), 4.00-3.89 (m, 2H), 1.67 (d, J = 7.2 Hz, 3H). |
| I-086 | 3,4'-bipyridine | iPr | 401.2 | DMSO-d₆: δ 10.95 (s, 1H), 10.10 (s, 1H), 8.95 (s, 1H), 8.90 (s, 1H), 8.75-8.69 (m, 1H), 8.39-8.37 (m, 1H), 8.12-8.10 (m, 1H), 8.09-8.07 (m, 1H), 8.00-7.96 (m, 2H), 7.77-7.75 (m, 1H), 7.62-7.59 (m, 1H), 7.47-7.45 (m, 1H), 5.50-5.41 (m, 1H), 1.55 (d, J = 6.8 Hz, 6H). |
| I-087 | 4,4'-bipyridine | iPr | 401.2 | DMSO-d₆: δ 10.84 (s, 1H), 10.15 (s, 1H), 8.91 (s, 1H), 8.77-8.75 (m, 2H), 8.41 (d, J = 5.6 Hz, 1H), 8.09 (d, J = 8.4 Hz, 1H), 8.01-7.96 (m, 2H), 7.77-7.73 (m, 3H), 7.49-7.48 (m, 1H), 5.45-5.38 (m, 1H), 1.55 (d, J = 6.8 Hz, 6H). |
| I-088 | 2,5'-bipyridine | iPr | 401.2 | DMSO-d₆: δ 10.78 (s, 1H), 10.17 (s, 1H), 8.96 (s, 1H), 8.91 (s, 1H), 8.67 (d, J = 4.0 Hz, 1H), 8.49-8.46 (m, 1H), 8.08 (d, J = 8.4 Hz, 1H), 8.00-7.96 (m, 2H), 7.92-7.88 (m, 1H), 7.78-7.75 (m, 2H), 7.38-7.35 (m, 1H), 5.44-5.38 (m, 1H), 1.55 (d, J = 6.4 Hz, 6H). |
| I-089 | 3,5'-bipyridine | iPr | 401.2 | DMSO-d₆: δ 10.71 (s, 1H), 10.12 (s, 1H), 8.95 (s, 1H), 8.91 (s, 1H), 8.65-8.60 (m, 2H), 8.22-8.19 (m, 1H), 8.14-8.08 (m, 2H), 8.00-7.96 (m, 1H), 7.81-7.75 (m, 2H), 7.53-7.50 (m, 1H), 5.44-5.37 (m, 1H), 1.55 (d, J = 6.4 Hz, 6H). |

TABLE 1-continued

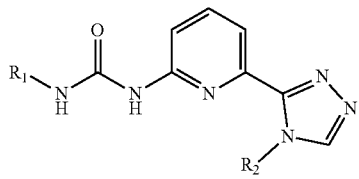

| Compound | R₁ | R₂ | LC-MS (M + H)⁺ | ¹HNMR (ppm) |
|---|---|---|---|---|
| I-090 | 4-(pyridin-4-yl)pyridin-2-yl | isopropyl | 401.2 | DMSO-d₆: δ 10.71 (s, 1H), 10.12 (s, 1H), 8.95-8.91 (m, 2H), 8.64-8.59 (m, 2H), 8.20 (d, J = 8.8 Hz, 1H), 8.14-8.08 (m, 2H), 8.00-7.96 (m, 1H), 7.81-7.75 (m, 2H), 7.53-7.50 (m, 1H), 5.44-5.37 (m, 1H), 1.54 (d, J = 6.5 Hz, 6H). |
| I-091 | 4-(tetrahydropyran-4-yl)pyridin-2-yl | isopropyl | 408.2 | DMSO-d₆: δ 11.27 (s, 1H), 9.96 (s, 1H), 8.90 (s, 1H), 8.18-8.16 (m, 1H), 8.09-8.07 (m, 1H), 7.98-7.94 (m, 1H), 7.74 (d, J = 7.6 Hz, 1H), 7.41 (s, 1H), 7.00 (d, J = 5.2 Hz, 1H), 5.43-5.36 (m, 1H), 3.98-3.94 (m, 2H), 3.47-3.42 (m, 2H), 2.81-2.76 (m, 1H), 1.71-1.67 (m, 2H), 1.65-1.61 (m, 2H), 1.53 (d, J = 6.8 Hz, 6H). |
| I-092 | 4-(tetrahydropyran-4-yl)pyridin-2-yl | 2-methyl-3-hydroxypropyl | 424.2 | CD₃OD-d₄: δ 8.82 (s, 1H), 8.20 (d, J = 5.2 Hz, 1H), 8.11 (d, J = 7.6 Hz, 1H), 7.96-7.92 (m, 1H), 7.76 (d, J = 7.2 Hz, 1H), 7.22 (s, 1H), 7.00-6.98 (m, 1H), 5.49-5.45 (m, 1H), 4.07-4.03 (m, 2H), 3.96-3.85 (m, 2H), 3.59-3.53 (m, 2H), 2.84-2.82 (m, 1H), 1.81-1.76 (m, 4H), 1.63 (d, J = 6.8 Hz, 3H). |
| I-093 | 5-morpholinopyridin-2-yl | isopropyl | 409.3 | DMSO-d₆: δ 9.75 (s, 1H), 8.89 (s, 1H), 8.03 (d, J = 7.8 Hz, 1H), 7.97-7.91 (m, 2H), 7.72-7.69 (m, 1H), 7.51-7.47 (m, 2H), 5.39-5.35 (m, 1H), 3.77-3.73 (m, 4H), 3.10-3.07 (m, 4H), 1.52 (d, J = 6.9 Hz, 6H). |
| I-094 | 4-morpholinopyridin-2-yl | isopropyl | 409.2 | DMSO-d₆: δ 11.85 (s, 1H), 9.66 (s, 1H), 8.88 (s, 1H), 8.08 (d, J = 8.4 Hz, 1H), 7.96-7.89 (m, 2H), 7.73 (d, J = 7.6 Hz, 1H), 6.79 (s, 1H), 6.63-6.61 (m, 1H), 5.42-5.35 (m, 1H), 3.74-3.72 (m, 4H), 3.26-3.24 (m, 4H), 1.54 (d, J = 6.4 Hz, 6H). |

TABLE 1-continued

| Compound | R₁ | R₂ | LC-MS (M + H)⁺ | ¹HNMR (ppm) |
|---|---|---|---|---|
| I-095 | piperazine-pyridine | isopropyl | 408.3 | DMSO-d₆: δ 9.59 (s, 1H), 8.88 (s, 1H), 8.09 (d, J = 8.0 Hz, 1H), 7.95-7.91 (m, 1H), 7.85 (d, J = 6.4 Hz, 1H), 7.73 (d, J = 7.6 Hz, 1H), 6.73 (s, 1H), 6.59-6.57 (m, 1H), 5.42-5.35 (m, 1H), 3.21-3.16 (m, 4H), 2.81-2.78 (m, 4H), 1.54 (d, J = 6.8 Hz, 6H). |
| I-096 | piperazine-pyridine | 2-hydroxymethylpropyl | 424.2 | DMSO-d₆: δ 9.61 (s, 1H), 8.79 (s, 1H), 8.08 (d, J = 8.4 Hz, 1H), 7.95-7.91 (m, 1H), 7.87 (d, J = 6.0 Hz, 1H), 7.72 (d, J = 7.2 Hz, 1H), 6.72 (s, 1H), 6.60-6.58 (m, 1H), 5.34-5.29 (m, 1H), 5.08-5.05 (m, 1H), 3.78-3.71 (m, 2H), 3.21-3.19 (m, 4H), 2.80-2.78 (m, 4H), 1.52 (d, J = 6.8 Hz, 3H). |
| I-097 | piperazine-pyridine | isopropyl | 408.2 | DMSO-d₆: δ 10.77 (s, 1H), 9.74 (s, 1H), 8.89 (s, 1H), 8.03 (d, J = 8.1 Hz, 1H), 7.96-7.87 (m, 2H), 7.72-7.69 (m, 1H), 7.48 (s, 2H), 5.42-5.33 (m, 1H), 3.03-3.00 (m, 4H), 2.85-2.80 (m, 4H), 1.52 (d, J = 6.9 Hz, 6H). |
| I-098 | N-isopropylpiperazine-pyridine | isopropyl | 450.3 | DMSO-d₆: δ 12.01 (s, 1H), 9.63 (s, 1H), 8.89 (s, 1H), 8.09 (d, J = 8.4 Hz, 1H), 7.96-7.92 (m, 1H), 7.86 (d, J = 6.4 Hz, 1H), 7.73 (d, J = 6.8 Hz, 1H), 6.74 (s, 1H), 6.61-6.59 (m, 1H), 5.41-5.34 (m, 1H), 3.45-3.17 (m, 4H), 2.73-2.65 (m, 1H), 2.56-2.50 (m, 4H), 1.54 (d, J = 6.8 Hz, 6H), 1.04-1.01 (m, 6H). |

TABLE 1-continued

| Compound | R₁ | R₂ | LC-MS (M + H)⁺ | ¹HNMR (ppm) |
|---|---|---|---|---|
| I-099 | 4-(4-ethylpiperazin-1-yl)pyridin-2-yl | isopropyl | 436.2 | DMSO-d₆: δ 11.94 (s, 1H), 9.62 (s, 1H), 8.89 (s, 1H), 8.09 (d, J = 8.4 Hz, 1H), 7.96-7.94 (m, 1H), 7.91-7.86 (m, 1H), 7.73 (d, J = 7.5 Hz, 1H), 6.82 (s, 1H), 6.62-6.54 (m, 1H), 5.42-5.33 (m, 1H), 3.32-3.27 (m, 4H), 2.47-2.40 (m, 4H), 2.38-2.27 (m, 2H), 1.54 (d, J = 6.6 Hz, 6H), 1.06-1.01 (m, 3H). |
| I-100 | 4-(4-cyclopropylpiperazin-1-yl)pyridin-2-yl | isopropyl | 448.2 | DMSO-d₆: δ 11.92 (s, 1H), 9.62 (s, 1H), 8.89 (s, 1H), 8.09 (d, J = 8.4 Hz, 1H), 7.96-7.92 (m, 1H), 7.86 (d, J = 6.4 Hz, 1H), 7.74-7.72 (m, 1H), 6.76 (s, 1H), 6.62-6.60 (m, 1H), 5.39-5.36 (m, 1H), 3.31-3.24 (m, 4H), 2.65-2.62 (m, 4H), 1.68-1.64 (m, 1H), 1.54 (d, J = 6.8 Hz, 6H), 0.46-0.43 (m, 2H), 0.38-0.32 (m, 2H). |
| I-101 | 4-(4-(2-hydroxyethyl)piperazin-1-yl)pyridin-2-yl | isopropyl | 452.2 | DMSO-d₆: δ 11.99 (s, 1H), 9.62 (s, 1H), 8.89 (s, 1H), 8.09 (d, J = 8.4 Hz, 1H), 7.96-7.92 (m, 1H), 7.86 (d, J = 6.0 Hz, 1H), 7.74-7.72 (m, 1H), 6.75 (s, 1H), 6.62-6.60 (m, 1H), 5.45-5.35 (m, 1H), 4.48-4.45 (m, 1H), 3.60-3.50 (m, 2H), 3.34-3.27 (m, 4H), 2.54-2.50 (m, 4H), 2.45-2.42 (m, 2H), 1.54 (d, J = 6.8 Hz, 6H). |
| I-102 | 4-(4-(methylsulfonyl)piperazin-1-yl)pyridin-2-yl | isopropyl | 485.9 | DMSO-d₆: δ 11.74 (s, 1H), 9.66 (s, 1H), 8.89 (s, 1H), 8.08 (d, J = 8.8 Hz, 1H), 7.96-7.90 (m, 2H), 7.73 (d, J = 7.6 Hz, 1H), 6.86 (s, 1H), 6.67-6.65 (m, 1H), 5.41-5.34 (m, 1H), 3.45-3.43 (m, 4H), 3.32-3.22 (m, 4H), 2.92 (s, 3H), 1.54 (d, J = 6.8 Hz, 6H). |

TABLE 1-continued
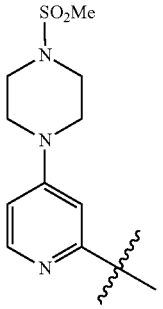 [SMILES: *c1cc(N2CCN(S(C)(=O)=O)CC2)ccn1]
| Compound | R₁ | R₂ | LC-MS (M + H)⁺ | ¹HNMR (ppm) |
|---|---|---|---|---|
| I-103 | 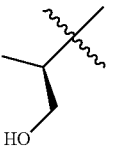 [SMILES: *[C@H](C)CO] | 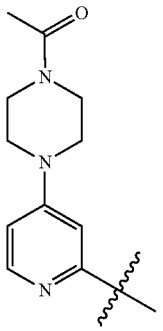 [SMILES: *c1cc(N2CCN(C(C)=O)CC2)ccn1] | 502.2 | DMSO-d₆: δ 11.81 (s, 1H), 9.66 (s, 1H), 8.79 (s, 1H), 8.07 (d, J = 8.4 Hz, 1H), 7.95-7.91 (m, 2H), 7.72 (d, J = 7.6 Hz, 1H), 6.85 (s, 1H), 6.67-6.65 (m, 1H), 5.33-5.29 (m, 1H), 5.07-5.04 (m, 1H), 3.74-3.71 (m, 2H), 3.44-3.40 (m, 4H), 3.24-3.22 (m, 4H), 2.92 (s, 3H), 1.51 (d, J = 6.8 Hz, 3H). |
| I-104 | 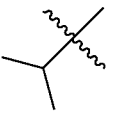 [SMILES: *C(C)C] | 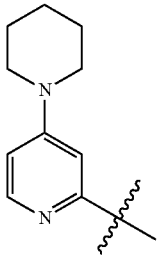 [SMILES: *c1cc(N2CCCCC2)ccn1] | 449.9 | DMSO-d₆: δ 11.95 (s, 1H), 9.66 (s, 1H), 8.89 (s, 1H), 8.09 (d, J = 8.0 Hz, 1H), 7.96-7.88 (m, 2H), 7.74-7.72 (m, 1H), 6.78 (s, 1H), 6.63-6.61 (m, 1H), 5.41-5.35 (m, 1H), 3.59-3.55 (m, 4H), 3.38-3.36 (m, 2H), 3.33-3.30 (m, 2H), 2.33 (s, 3H), 1.54 (d, J = 6.8 Hz, 6H). |
| I-105 |  | 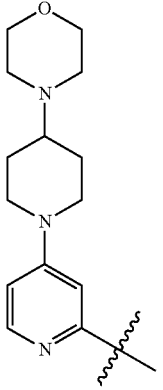 [SMILES: *c1cc(N2CCC(N3CCOCC3)CC2)ccn1] | 407.2 | DMSO-d₆: δ 12.08 (s, 1H), 9.56 (s, 1H), 8.88 (s, 1H), 8.09 (d, J = 8.4 Hz, 1H), 7.95-7.91 (m, 1H), 7.83 (d, J = 6.0 Hz, 1H), 7.73 (d, J = 7.6 Hz 1H), 6.71 (s, 1H), 6.58-6.56 (m, 1H), 5.42-5.35 (m, 1H), 3.34-3.31 (m, 4H), 1.61-1.53 (m, 12H). |
| I-106 |  | | 492.3 | DMSO-d₆: δ 12.02 (s, 1H), 9.59 (s, 1H), 8.89 (s, 1H), 8.09 (d, J = 8.4 Hz, 1H), 7.96-7.92 (m, 1H), 7.84 (d, J = 6.4 Hz, 1H), 7.74-7.72 (m, 1H), 6.74 (s, 1H), 6.61-6.59 (m, 1H), 5.41-5.34 (m, 1H), 3.86-3.82 (m, 2H), 3.57-3.55 (m, 4H), 2.91-2.85 (m, 2H), 2.51-2.45 (m, 4H), 2.43-2.37 (m, 1H), 1.87-1.84 (m, 2H), 1.54 (d, J = 6.8 Hz, 6H), 1.32-1.45 (m, 2H). |

TABLE 1-continued
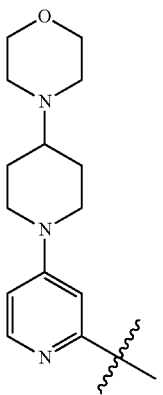 [SMILES: *c1cc(N2CCC(N3CCOCC3)CC2)ccn1]
| Compound | R₁ | R₂ | LC-MS (M + H)⁺ | ¹HNMR (ppm) |
|---|---|---|---|---|
| I-107 | 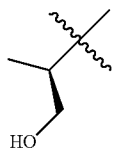 [SMILES: *[C@H](C)CO] | 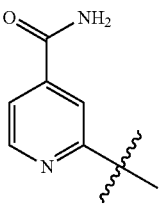 [SMILES: *c1cc(C(N)=O)ccn1] | 508.3 | DMSO-d₆: δ 9.58 (s, 1H), 8.78 (s, 1H), 8.08 (d, J = 8.4 Hz, 1H), 7.95-7.91 (m, 1H), 7.87 (d, J = 6.4 Hz, 1H), 7.72 (d, J = 7.6 Hz, 1H), 6.61-6.59 (m, 1H), 6.53 (s, 1H), 5.33-5.29 (m, 1H), 5.07-5.05 (m, 1H), 3.86-3.83 (m, 2H), 3.74-3.72 (m, 2H), 3.60-3.50 (m, 4H), 2.90-2.84 (m, 2H), 2.49-2.40 (m, 5H), 1.87-1.84 (m, 2H), 1.52 (d, J = 7.6 Hz, 3H), 1.45-1.32 (m, 2H). |
| I-108 | 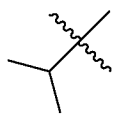 | 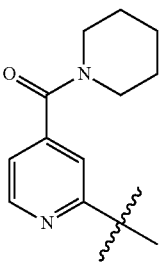 [SMILES: *c1cc(C(=O)N2CCCCC2)ccn1] | 367.2 | DMSO-d₆: δ 10.78 (s, 1H), 10.13 (s, 1H), 8.89 (s, 1H), 8.36 (d, J = 5.2 Hz, 1H), 8.20 (s, 1H), 8.08-7.95 (m, 3H), 7.75 (d, J = 7.6 Hz, 1H), 7.70 (s, 1H), 7.42 (d, J = 4.0 Hz, 1H), 5.45-5.35 (m, 1H), 1.53 (d, J = 6.8 Hz, 6H). |
| I-109 | 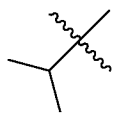 [SMILES: *C(C)C] | 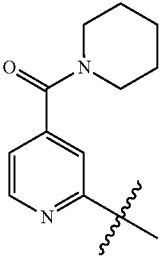 [SMILES: *c1cc(C(=O)N2CCCCC2)ccn1] | 435.2 | CD₃OD-d₄: δ 8.85 (s, 1H), 8.34 (d, J = 5.2 Hz, 1H), 8.10 (d, J = 8.4 Hz, 1H), 7.98-7.94 (m, 1H), 7.75 (d, J = 7.6 Hz, 1H), 7.47 (s, 1H), 7.04-7.02 (m, 1H), 5.55-5.48 (m, 1H), 3.73-3.70 (m, 2H), 3.37-3.34 (m, 2H), 1.74-1.71 (m, 4H), 1.70-1.58 (m, 8H). |
| I-110 | 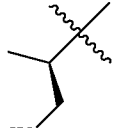 | 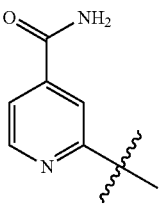 [SMILES: *c1cc(C(N)=O)ccn1] | 451.2 | CD₃OD-d₄: δ 8.83 (s, 1H), 8.38-8.36 (m, 1H), 8.09-8.06 (m, 1H), 7.97-7.93 (m, 1H), 7.76-7.74 (m, 1H), 7.47 (s, 1H), 7.04-7.02 (m, 1H), 5.55-5.45 (m, 1H), 3.94-3.84 (m, 2H), 3.73-3.70 (m, 2H), 3.35-3.32 (m, 2H), 1.74-1.58 (m, 9H). |

TABLE 1-continued

| Compound | R₁ | R₂ | LC-MS (M + H)⁺ | ¹HNMR (ppm) |
|---|---|---|---|---|
| I-111 | piperidine-carbonyl-pyridinyl | phenyl phosphoramidate isopropyl alaninate (S) | 720.3 | DMSO-d₆: δ 10.86 (s, 1H), 9.99 (s, 1H), 8.87 (s, 1H), 8.35 (d, J = 5.2 Hz, 1H), 8.05 (d, J = 8.4 Hz, 1H), 7.98-7.94 (m, 1H), 7.77 (d, J = 7.2 Hz, 1H), 7.53 (s, 1H), 7.26-7.22 (m, 2H), 7.10-7.07 (m, 1H), 7.00-6.95 (m, 3H), 6.03-5.97 (m, 1H), 5.71-5.67 (m, 1H), 4.79-4.74 (m, 1H), 4.40-4.37 (m, 2H), 3.59-3.49 (m, 3H), 3.30-3.19 (m, 2H), 1.63-1.46 (m, 9H), 1.10-1.06 (m, 9H). |
| I-112 | piperidine-carbonyl-pyridinyl | phenyl phosphoramidate isopropyl alaninate (R) | 720.3 | DMSO-d₆: δ 10.86 (s, 1H), 9.99 (s, 1H), 8.79 (s, 1H), 8.36 (d, J = 5.2 Hz, 1H), 8.05 (d, J = 8.4 Hz, 1H), 7.98-7.94 (m, 1H), 7.74 (d, J = 7.2 Hz, 1H), 7.55 (s, 1H), 7.34-7.30 (m, 2H), 7.17-7.10 (m, 3H), 7.01-6.99 (m, 1H), 6.06-6.00 (m, 1H), 5.61-5.50 (m, 1H), 4.79-4.75 (m, 1H), 4.45-4.42 (m, 1H), 4.32-4.29 (m, 1H), 3.65-3.59 (m, 3H), 3.30-3.19 (m, 2H), 1.63-1.46 (m, 9H), 1.13-1.06 (m, 9H). |
| I-113 | piperidine-carbonyl-pyridinyl | 2,2-dimethylbutanoate ester | 549.3 | DMSO-d₆: δ 10.87 (s, 1H), 10.10 (s, 1H), 8.94 (s, 1H), 8.36 (d, J = 5.2 Hz, 1H), 8.10-8.03 (m, 1H), 7.99-7.93 (m, 1H), 7.82-7.75 (m, 1H), 7.53 (s, 1H), 7.07-7.01 (m, 1H), 5.81-5.69 (m, 1H), 4.46-4.32 (m, 2H), 3.64-3.56 (m, 2H), 3.28-3.21 (m, 2H), 1.68-1.53 (m, 7H), 1.50-1.44 (m, 2H), 1.32-1.21 (m, 2H), 0.88 (s, 3H), 0.87 (s, 3H), 0.57-0.51 (m, 3H). |
| I-114 | piperidine-carbonyl-pyridinyl | heptanoate ester | 563.3 | DMSO-d₆: δ 10.75 (s, 1H), 10.10 (s, 1H), 8.93 (s, 1H), 8.36 (d, J = 5.4 Hz, 1H), 8.07-7.95 (m, 2H), 7.78-7.75 (m, 1H), 7.56 (s, 1H), 7.04-7.02 (m, 1H), 5.76-5.64 (m, 1H), 4.49-4.39 (m, 1H), 4.36-4.22 (m, 1H), 3.65-3.51 (m, 2H), 3.26-3.16 (m, 2H), 2.17-1.89 (m, 2H), 1.68-1.37 (m, 9H), 1.34-1.20 (m, 2H), 1.18-1.07 (m, 6H), 0.82-0.77 (m, 3H). |

TABLE 1-continued

| Compound | R₁ | R₂ | LC-MS (M + H)⁺ | ¹HNMR (ppm) |
|---|---|---|---|---|
| I-115 | piperidine-C(O)-pyridinyl | 1-methylcyclopropyl-methyl | 447.2 | DMSO-d₆: δ 11.07 (s, 1H), 10.20 (s, 1H), 8.75 (s, 1H), 8.28 (d, J = 5.1 Hz, 1H), 8.12 (d, J = 7.8 Hz, 1H), 7.97-7.91 (m, 1H), 7.72 (d, J = 6.9 Hz, 1H), 7.39 (s, 1H), 7.01-6.99 (m, 1H), 3.60-3.50 (m, 2H), 3.32-3.22 (m, 2H), 1.73 (s, 3H), 1.60-1.40 (m, 6H), 1.04-1.00 (m, 4H). |
| I-116 | piperidine-C(O)-pyridinyl | 1-(hydroxymethyl-cyclopropyl)-propyl | 477.2 | DMSO-d₆: δ 10.86 (s, 1H), 9.99 (s, 1H), 8.79 (s, 1H), 8.36 (d, J = 5.2 Hz, 1H), 8.05 (d, J = 8.4 Hz, 1H), 7.98-7.94 (m, 1H), 7.74-7.30 (m, 2H), 7.17-7.10 (m, 3H), 7.01-6.99 (m, 1H), 6.06-6.00 (m, 1H), 5.61-5.50 (m, 1H), 4.79-4.75 (m, 1H), 4.45-4.42 (m, 1H), 4.32-4.29 (m, 1H), 3.65-3.59 (m, 3H), 3.30-3.19 (m, 2H), 1.63-1.46 (m, 9H), 1.13-1.06 (m, 9H). |
| I-117 | 4,4-dimethylpiperidine-C(O)-pyridinyl | isopropyl | 463.2 | CD₃OD-d₄: δ 8.89 (s, 1H), 8.37-8.35 (m, 1H), 8.12 (d, J = 8.0 Hz, 1H), 8.00-7.96 (m, 1H), 7.77 (d, J = 7.6 Hz, 1H), 7.49 (s, 1H), 7.06-7.04 (m, 1H), 5.57-5.50 (m, 1H), 3.78-3.75 (m, 2H), 3.41-3.38 (m, 2H), 1.64 (d, J = 6.8 Hz, 6H), 1.52-1.49 (m, 2H), 1.42-1.39 (m, 2H), 1.05 (s, 6H). |
| I-118 | (2S)-2-methylpiperidine-C(O)-pyridinyl | isobutyl | 449.2 | DMSO-d₆: δ10.51 (s, 1H), 9.80 (s, 1H), 8.67 (s, 1H), 8.23 (d, J = 5.1 Hz, 1H), 7.95-7.83 (m, 2H), 7.66 (d, J = 7.5 Hz, 1H), 7.50 (s, 1H), 6.91-6.89 (m, 1H), 5.36-5.31 (m, 1H), 4.24 (s, 1H), 3.76 (s, 1H), 2.86 (s, 1H), 1.60-1.51 (m, 11H), 1.47-1.44 (m, 1H), 1.14 (d, J = 6.9 Hz, 3H). |
| I-119 | (2S)-2-methylpiperidine-C(O)-pyridinyl | 2-methyl-3-hydroxypropyl | 465.2 | CD₃OD-d₄: δ 9.36-9.30 (m, 1H), 8.37 (d, J = 5.2 Hz, 1H), 8.18-8.14 (m, 1H), 8.02-7.97 (m, 1H), 7.80 (d, J = 7.6 Hz, 1H), 7.45 (s, 1H), 7.10-7.00 (m, 1H), 5.68-5.55 (m, 1H), 4.90-4.87 (m, 0.5H), 4.49-4.40 (m, 0.5H), 3.98-3.94 (m, 1H), 3.90-3.84 (m, 1H), 3.48-3.39 (m, 1H), 3.31-3.12 (m, 1H), 1.79-1.52 (m, 9H), 1.30-1.20 (m, 3H). |

TABLE 1-continued
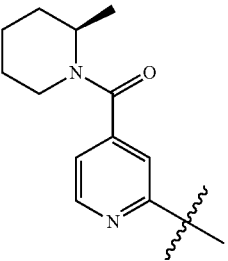 [SMILES: *c1cc(C(=O)N2CCCC[C@H]2C)ccn1]
| Compound | R₁ | R₂ | LC-MS (M + H)⁺ | ¹HNMR (ppm) |
|---|---|---|---|---|
| I-120 |  | 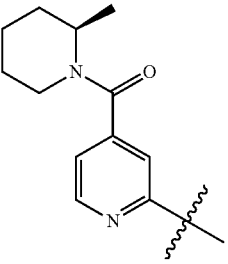 [SMILES: *c1cc(C(=O)N2CCCC[C@H]2C)ccn1] | 449.2 | DMSO-d₆: δ 10.55 (s, 1H), 9.88 (s, 1H), 8.74 (s, 1H), 8.30 (d, J = 4.5 Hz, 1H), 8.01-7.89 (m, 2H), 7.74-7.71 (m, 1H), 7.57 (s, 1H), 6.97-6.95 (m, 1H), 5.45-5.36 (m, 1H), 4.47-4.15 (m, 1H), 3.97-3.64 (s, 1H), 3.00-2.80 (m, 1H), 1.79-1.29 (m, 12H), 1.21 (d, J = 6.9 Hz, 3H). |
| I-121 | 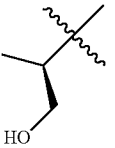 [SMILES: *[C@H](C)CO] | 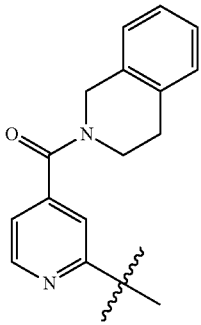 [SMILES: *c1cc(C(=O)N2CCc3ccccc3C2)ccn1] | 465.3 | DMSO-d₆: δ 10.79 (s, 1H), 10.11 (s, 1H), 8.80 (s, 1H), 8.34 (d, J = 5.1 Hz, 1H), 8.06-8.03 (m, 1H), 7.99-7.94 (m, 1H), 7.76-7.73 (m, 1H), 7.55 (s, 1H), 7.02 (d, J = 3.9 Hz, 1H), 5.36-5.30 (m, 1H), 5.08-5.04 (m, 1H), 4.78-4.33 (m, 1H), 3.74-3.70 (m, 2H), 3.32-3.20 (m, 1H), 3.16-2.86 (m, 1H), 1.66-1.10 (m, 12H). |
| I-122 | 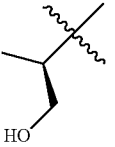 [SMILES: *[C@H](C)CO] | 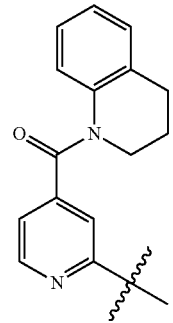 [SMILES: *c1cc(C(=O)N2CCCc3ccccc32)ccn1] | 499.2 | CD₃OD-d₄: δ 9.22 (s, 1H), 8.41 (d, J = 6.0 Hz, 1H), 8.15-8.12 (m, 1H), 8.01-7.96 (m, 1H), 7.81-7.78 (m, 1H), 7.55-7.48 (m, 1H), 7.22-6.97 (m, 5H), 5.60-5.55 (m, 1H), 4.58 (s, 1H), 3.99-3.85 (m, 3H), 3.67-3.63 (m, 1H), 3.02-2.90 (m, 2H), 1.67 (d, J = 6.9 Hz, 3H). |
| I-123 | 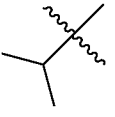 [SMILES: *C(C)C] | 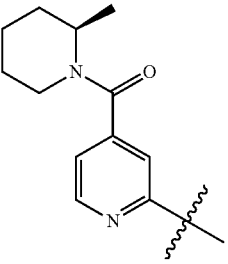 [SMILES: *c1cc(C(=O)N2CCCC[C@H]2C)ccn1] | 483.2 | CD₃OD-d₄: δ 8.86 (s, 1H), 8.24-8.22 (m, 1H), 8.11 (d, J = 8.4 Hz, 1H), 7.99-7.94 (m, 1H), 7.77 (d, J = 7.5 Hz, 1H), 7.41 (s, 1H), 7.25 (d, J = 7.5 Hz, 1H), 7.13-7.07 (m, 1H), 6.97-6.80 (m, 3H), 5.56-5.47 (m, 1H), 3.92-3.88 (m, 2H), 2.93-2.89 (m, 2H), 2.14-2.05 (m, 2H), 1.63 (d, J = 6.9 Hz, 6H). |

TABLE 1-continued

| Compound | R₁ | R₂ | LC-MS (M + H)⁺ | ¹HNMR (ppm) |
|---|---|---|---|---|
| I-124 | (tetrahydroquinoline-carbonyl-pyridinyl group) | (2-hydroxymethyl-propyl group) | 499.2 | DMSO-d₆: δ 10.77 (s, 1H), 10.02 (s, 1H), 8.73 (s, 1H), 8.18-8.11 (m, 1H), 7.96 (d, J = 8.4 Hz, 1H), 7.91-7.87 (m, 1H), 7.78-7.62 (m, 1H), 7.55-7.46 (m, 1H), 7.23-7.15 (m, 1H), 6.99-6.70 (m, 4H), 5.27-5.19 (m, 1H), 5.01-4.95 (m, 1H), 3.67-3.63 (m, 4H), 2.78-2.74 (m, 2H), 1.91-1.88 (m, 2H), 1.44 (d, J = 6.8 Hz, 3H). |
| I-125 | (decahydroquinoline-carbonyl-pyridinyl group) | (isobutyl group) | 489.3 | DMSO-d₆: δ 10.75 (s, 1H), 10.10 (s, 1H), 8.91 (s, 1H), 8.32 (d, J = 5.1 Hz, 1H), 8.07-8.04 (m, 1H), 8.00-7.95 (m, 1H), 7.77-7.74 (m, 1H), 7.56 (s, 1H), 7.02-7.00 (m, 1H), 5.42-5.38 (m, 1H), 3.40-3.31 (m, 2H), 3.28-3.10 (m, 1H), 2.15-2.08 (m, 1H), 1.72-1.63 (m, 7H), 1.53 (d, J = 6.6 Hz, 6H), 1.51-1.45 (m, 1H), 1.35-1.23 (m, 2H), 1.22-1.03 (m, 2H). |
| I-126 | (trans-decahydroquinoline-carbonyl-pyridinyl group) | (2-hydroxymethyl-propyl group) | 505.5 | DMSO-d₆: δ 10.76 (s, 1H), 10.09 (s, 1H), 8.80 (s, 1H), 8.33 (d, J = 5.1 Hz, 1H), 8.03 (d, J = 0.9 Hz, 1H), 7.97 (d, J = 7.5 Hz, 1H), 7.75-7.73 (m, 1H), 7.55 (s, 1H), 7.02-7.00 (m, 1H), 5.45-5.25 (m, 1H), 5.11-4.88 (m, 1H), 3.73-3.67 (m, 2H), 3.27-3.10 (m, 1H), 2.11-2.00 (m, 1H), 1.82-1.57 (m, 7H), 1.56-1.48 (m, 4H), 1.36-0.95 (m, 5H). |
| I-127 | (decahydroisoquinoline-carbonyl-pyridinyl group) | (isobutyl group) | 489.3 | CDCl₃: δ 8.41 (s, 1H), 8.26 (d, J = 5.2 Hz, 1H), 8.10-7.95 (m, 1H), 7.96 (d, J = 7.6 Hz, 1H), 7.87-7.83 (m, 1H), 7.15-700 (m, 1H), 6.97 (d, J = 5.2 Hz, 1H), 5.58-5.54 (m, 1H), 4.79-4.58 (m, 1H), 3.65-3.41 (m, 1H), 3.06-2.35 (m, 2H), 1.89-1.54 (m, 9H), 1.42-0.86 (m, 9H). |

TABLE 1-continued

| Compound | R₁ | R₂ | LC-MS (M + H)⁺ | ¹HNMR (ppm) |
|---|---|---|---|---|
| I-128 | (3-oxo-9-azaspiro[5.5]undecane carbonyl pyridine) | isopropyl | 503.3 | CD₃OD-d₄: δ 8.87 (s, 1H), 8.36 (d, J = 4.8 Hz, 1H), 8.12 (d, J = 8.7 Hz, 1H), 8.00-7.95 (m, 1H), 7.77 (d, J = 7.5 Hz, 1H), 7.49 (s, 1H), 7.05 (d, J = 5.4 Hz, 1H), 5.58-5.49 (m, 1H), 3.77-3.73 (m, 2H), 3.49-3.36 (m, 2H), 1.64 (d, J = 6.6 Hz, 6H), 1.61-1.40 (m, 14H). |
| I-129 | (3-oxo-9-azaspiro[5.5]undecane carbonyl pyridine) | 1-hydroxy-2-methylpropan-2-yl | 519.3 | CD₃OD-d₄: δ 8.83 (s, 1H), 8.37 (d, J = 5.2 Hz, 1H), 8.08 (d, J = 8.4 Hz, 1H), 7.97-7.93 (m, 1H), 7.76 (d, J = 7.6 Hz, 1H), 7.46 (s, 1H), 7.04-7.02 (m, 1H), 5.52-5.44 (m, 1H), 3.94-3.84 (m, 2H), 3.74-3.71 (m, 2H), 3.37-3.34 (m, 2H), 1.63 (d, J = 7.2 Hz, 3H), 1.58-1.55 (m, 2H), 1.48-1.40 (m, 12H). |
| I-130 | (4-morpholinopiperidine carbonyl pyridine) | isopropyl | 520.4 | CD₃OD-d₄: δ 8.88 (s, 1H), 8.38 (d, J = 5.1 Hz, 1H), 8.26 (s, 1H), 8.10 (d, J = 7.5 Hz, 1H), 8.00-7.95 (m, 1H), 7.77 (d, J = 7.2 Hz, 1H), 7.60-7.50 (m, 1H), 7.09-7.07 (m, 1H), 5.57-5.48 (m, 1H), 4.76-4.71 (m, 1H), 3.83-3.76 (m, 5H), 3.24-3.16 (m, 1H), 3.00-2.80 (m, 6H), 2.20-2.10 (m, 1H), 2.05-1.95 (m, 1H), 1.64 (d, J = 6.9 Hz, 6H), 1.63-1.50 (m, 2H). |
| I-131 | (4-morpholinopiperidine carbonyl pyridine) | 1-hydroxy-2-methylpropan-2-yl | 536.2 | CD₃OD-d₄: δ 8.85 (s, 1H), 8.41-8.39 (m, 1H), 8.11-8.09 (m, 1H), 8.00-7.95 (m, 1H), 7.79-7.77 (m, 1H), 7.51 (s, 1H), 7.09-7.06 (m, 1H), 5.51-5.49 (m, 1H), 4.70-4.60 (m, 1H), 4.00-3.89 (m, 2H), 3.80-3.74 (m, 5H), 3.21-3.08 (m, 1H), 3.01-2.83 (m, 1H), 2.64-2.54 (m, 5H), 2.06-1.91 (m, 2H), 1.65 (d, J = 6.9 Hz, 3H), 1.55-1.49 (m, 2H). |

TABLE 1-continued

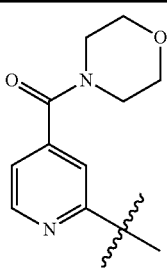

| Compound | R₁ | R₂ | LC-MS (M + H)⁺ | ¹HNMR (ppm) |
|---|---|---|---|---|
| I-132 | 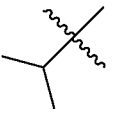 | 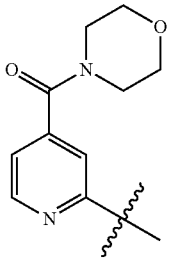 [SMILES: *c1cc(C(=O)N2CCOCC2)ccn1] | 437.2 | DMSO-d₆: δ 10.79 (s, 1H), 10.13 (s, 1H), 8.90 (s, 1H), 8.34 (d, J = 5.2 Hz, 1H), 8.05 (d, J = 8.0 Hz, 1H), 7.99-7.95 (m, 1H), 7.75 (d, J = 6.8 Hz, 1H), 7.61 (s, 1H), 7.08-7.06 (m, 1H), 5.41-5.38 (m, 1H), 3.66-3.54 (m, 6H), 1.53 (d, J = 6.8 Hz, 6H). |
| I-133 | 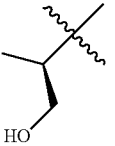 [SMILES: *[C@H](C)CO] | 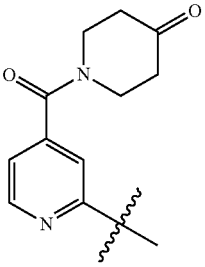 [SMILES: *c1cc(C(=O)N2CCC(=O)CC2)ccn1] | 453.2 | DMSO-d₆: δ 10.75 (s, 1H), 10.12 (s, 1H), 8.79 (s, 1H), 8.35 (d, J = 5.2 Hz, 1H), 8.04 (d, J = 8.4 Hz, 1H), 7.98-7.94 (m, 1H), 7.74 (d, J = 7.2 Hz, 1H), 7.60 (s, 1H), 7.07 (d, J = 4.8 Hz, 1H), 5.35-5.25 (m, 1H), 5.06-5.03 (m, 1H), 3.73-3.64 (m, 6H), 3.58-3.52 (m, 2H), 1.51 (d, J = 7.2 Hz, 3H). |
| I-134 |  | 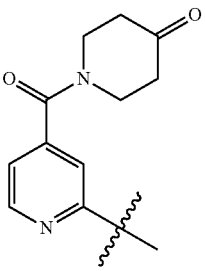 [SMILES: *c1cc(C(=O)N2CCC(=O)CC2)ccn1] | 449.2 | CD₃OD-d₄: δ 8.87 (s, 1H), 8.40-8.36 (m, 1H), 8.13-8.10 (m, 1H), 7.99-7.95 (m, 1H), 7.77 (d, J = 7.6 Hz, 1H), 7.60-7.49 (m, 1H), 7.17-7.06 (m, 1H), 5.55-5.51 (m, 1H), 4.08-3.74 (m, 3H), 3.44-3.42 (m, 1H), 2.68-2.45 (m, 1H), 1.88-1.84 (m, 3H), 1.64 (d, J = 6.8 Hz, 6H). |
| I-135 | 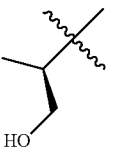 [SMILES: *[C@H](C)CO] | 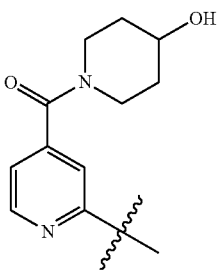 [SMILES: *c1cc(C(=O)N2CCC(O)CC2)ccn1] | 465.2 | DMSO-d₆: δ 10.79 (s, 1H), 10.19 (s, 1H), 8.80 (s, 1H), 8.37 (d, J = 5.2 Hz, 1H), 8.04 (d, J = 8.4 Hz, 1H), 7.98-7.94 (m, 1H), 7.75-7.69 (m, 2H), 7.15 (d, J = 5.6 Hz, 1H), 5.37-5.32 (m, 1H), 5.09-5.03 (m, 1H), 3.90-3.80 (m, 2H), 3.71-3.65 (m, 2H), 3.60-3.50 (m, 2H), 2.45-2.38 (m, 2H), 1.51 (d, J = 7.2 Hz, 3H). |
| I-136 |  | 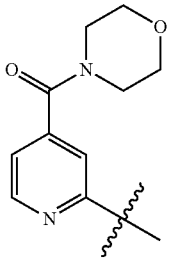 [SMILES: *c1cc(C(=O)N2CCOCC2)ccn1] | 451.2 | DMSO-d): δ 10.79 (s, 1H), 10.11 (s, 1H), 8.90 (s, 1H), 8.33 (d, J = 4.8 Hz, 1H), 8.06 (d, J = 8.0 Hz, 1H), 7.99-7.95 (m, 1H), 7.76-7.74 (m, 1H), 7.57 (s, 1H), 7.04-7.02 (m, 1H), 5.41-5.38 (m, 1H), 4.84 (d, J = 4.0 Hz, 1H), 4.02-3.98 (m, 1H), 3.77-3.74 (m, 1H), 3.45-3.41 (m, 1H), 3.33-3.25 (m, 1H), 3.13-3.10 (m, 1H), 1.82-1.80 (m, 1H), 1.71-1.68 (m, 1H), 1.53 (d, J = 6.8 Hz, 6H), 1.41-1.32 (m, 2H). |

TABLE 1-continued

| Compound | R₁ | R₂ | LC-MS (M + H)⁺ | ¹HNMR (ppm) |
|---|---|---|---|---|
| I-137 | piperidine-4-ol carbonyl linked to pyridine with methyl attachment | CH(CH₃)CH₂OH | 467.2 | DMSO-d₆: δ 10.79 (s, 1H), 10.11 (s, 1H), 8.80 (s, 1H), 8.35 -8.33 (m, 1H), 8.06-8.03 (m, 1H), 7.98-7.94 (m, 1H), 7.75-7.73 (m, 1H), 7.57 (s, 1H), 7.05-7.03 (m, 1H), 7.35-5.29 (m, 1H), 5.07-5.05 (m, 1H), 4.84 (d, J = 4.0 Hz, 1H), 4.05-3.95 (m, 1H), 3.73-3.70 (m, 3H), 3.47-3.41 (m, 1H), 3.29-3.21 (m, 1H), 3.15-3.05 (m, 1H), 1.88-1.79 (m, 1H), 1.75-1.65 (m, 1H), 1.52 (d, J = 6.8 Hz, 3H), 1.45-1.27 (m, 2H). |
| I-138 | 4-methyl-4-hydroxypiperidine carbonyl pyridine | isopropyl | 465.3 | DMSO-d₆: δ 10.82 (s, 1H), 10.09 (s, 1H), 8.88 (s, 1H), 8.31 (d, J = 5.1 Hz, 1H), 8.05-7.92 (m, 2H), 7.75-7.72 (m, 1H), 7.54 (s, 1H), 7.03-7.01 (m, 1H), 5.40-5.36 (m, 1H), 4.46 (s, 1H), 4.08-4.03 (m, 1H), 3.28-3.21 (m, 3H), 1.53-1.51 (m, 8H), 1.44-1.39 (m, 2H), 1.15 (s, 3H). |
| I-139 | piperazine carbonyl pyridine | isopropyl | 436.2 | CD₃OH-d₄: δ 8.88 (s, 1H), 8.37 (d, J = 5.4 Hz, 1H), 8.12 (d, J = 8.4 Hz, 1H), 7.99-7.94 (m, 1H), 7.77 (d, J = 7.5 Hz, 1H), 7.51 (s, 1H), 7.08 (d, J = 4.8 Hz, 1H), 5.57-5.48 (m, 1H), 3.80-3.70 (m, 2H), 3.45-3.38 (m, 2H), 2.98-2.90 (m, 2H), 2.88-2.80 (m, 2H), 1.64 (d, J = 6.9 Hz, 6H). |
| I-140 | piperazine carbonyl pyridine | CH(CH₃)CH₂OH | 452.2 | DMSO-d₆: δ 10.80 (s, 1H), 10.13 (s, 1H), 8.80 (s, 1H), 8.35 (d, J = 5.1 Hz, 1H), 8.06-7.94 (m, 2H), 7.76-7.74 (m, 1H), 7.58 (s, 1H), 7.06-7.03 (m, 1H), 5.39-5.28 (m, 1H), 5.07 (s, 1H), 3.75-3.71 (m, 2H), 3.60-3.50 (m, 2H), 3.33-3.18 (m, 2H), 2.80-2.60 (m, 4H), 1.52 (d, J = 6.9 Hz, 3H). |
| I-141 | 4-methylpiperazine carbonyl pyridine | isopropyl | 450.2 | CD₃OD-d₄: δ 8.86 (s, 1H), 8.34 (d, J = 5.2 Hz, 1H), 8.09 (d, J = 8.4 Hz, 1H), 7.96-7.92 (m, 1H), 7.75 (d, J = 7.6 Hz, 1H), 7.49 (s, 1H), 7.05 (d, J = 4.4 Hz, 1H), 5.54-5.47 (m, 1H), 3.88-3.75 (m, 2H), 3.47-3.41 (m, 2H), 2.58-2.49 (s, 2H), 2.45-2.40 (s, 2H), 2.34 (s, 3H), 1.61 (d, J = 6.8 Hz, 6H). |

TABLE 1-continued

| Compound | R₁ | R₂ | LC-MS (M + H)⁺ | ¹HNMR (ppm) |
|---|---|---|---|---|
| I-142 | (4-methylpiperazin-1-yl)carbonyl-pyridin-2-yl (attached via methyl) | 2-hydroxy-1-methylethyl | 466.2 | DMSO-d₆: δ 10.80 (s, 1H), 10.13 (s, 1H), 8.81 (s, 1H), 8.38-8.35 (m, 1H), 8.05 (d, J = 8.4 Hz, 1H), 7.99-7.95 (m, 1H), 7.76-7.71 (m, 1H), 7.58 (s, 1H), 7.05-7.03 (m, 1H), 5.37-5.29 (m, 1H), 5.10-5.07 (m, 1H), 3.74-3.71 (m, 2H), 3.68-3.60 (m, 2H), 3.30-3.25 (m, 2H), 2.40-2.34 (m, 2H), 2.30-2.25 (m, 2H), 2.20 (s, 3H), 1.53 (d, J = 6.8 Hz, 3H). |
| I-143 | (4,4-difluoropiperidin-1-yl)carbonyl-pyridin-2-yl (attached via methyl) | isopropyl | 471.2 | CD₃OD-d₄: δ 8.87 (s, 1H), 8.38 (d, J = 5.1 Hz, 1H), 8.12 (d, J = 8.4 Hz, 1H), 8.00-7.95 (m, 1H), 7.77 (d, J = 7.2 Hz, 1H), 7.56 (s, 1H), 7.12 (d, J = 6.0 Hz, 1H), 5.60-5.49 (m, 1H), 3.91-3.83 (m, 2H), 3.60-3.50 (m, 2H), 2.12-1.95 (m, 4H), 1.64 (d, J = 6.6 Hz, 6H). |
| I-144 | (4,4-difluoropiperidin-1-yl)carbonyl-pyridin-2-yl (attached via methyl) | 2-hydroxy-1-methylethyl | 487.2 | DMSO-d₆: δ 10.75 (s, 1H), 10.14 (s, 1H), 8.80 (s, 1H), 8.36 (d, J = 5.2 Hz, 1H), 8.04 (d, J = 7.6 Hz, 1H), 7.98-7.94 (m, 1H), 7.75-7.73 (m, 1H), 7.64 (s, 1H), 7.14-7.12 (m, 1H), 5.35-5.31 (m, 1H), 5.07-5.04 (m, 1H), 3.73-3.70 (m, 4H), 3.39-3.33 (m, 2H), 2.10-2.02 (m, 4H), 1.51 (d, J = 6.8 Hz, 3H). |
| I-145 | (pyrrolidin-1-yl)carbonyl-pyridin-2-yl (attached via methyl) | isopropyl | 421.2 | CD₃OD-d₄: δ 8.87 (s, 1H), 8.37 (d, J = 5.2 Hz, 1H), 8.12 (d, J = 8.4 Hz, 1H), 7.99-7.95 (m, 1H), 7.77 (d, J = 7.6 Hz, 1H), 7.58 (s, 1H), 7.16-7.14 (m, 1H), 5.57-5.50 (m, 1H), 3.64-3.61 (m, 2H), 3.49-3.45 (m, 2H), 2.06-1.90 (m, 4H), 1.64 (d, J = 6.8 Hz, 6H). |
| I-146 | (pyrrolidin-1-yl)carbonyl-pyridin-2-yl (attached via methyl) | 2-hydroxy-1-methylethyl | 437.2 | DMSO-d₆: δ 10.78 (s, 1H), 10.11 (s, 1H), 8.79 (s, 1H), 8.34 (d, J = 5.2 Hz, 1H), 8.04 (d, J = 8.0 Hz, 1H), 7.98-7.94 (m, 1H), 7.74 (d, J = 7.2 Hz, 1H), 7.67 (s, 1H), 7.15-7.13 (m, 1H), 5.38-5.32 (m, 1H), 5.04 (s, 1H), 3.73-3.70 (m, 2H), 3.49-3.46 (m, 2H), 3.36-3.31 (m, 2H), 1.90-1.82 (m, 4H), 1.51 (d, J = 7.2 Hz, 3H). |

TABLE 1-continued

| Compound | R₁ | R₂ | LC-MS (M + H)⁺ | ¹HNMR (ppm) |
|---|---|---|---|---|
| I-147 | azepane-carbonyl-pyridinyl (methyl) | isopropyl | 449.2 | CD₃OD-d₄: δ 8.87 (s, 1H), 8.36 (d, J = 5.2 Hz, 1H), 8.12 (d, J = 8.0 Hz, 1H), 7.99-7.95 (m, 1H), 7.77 (d, J = 6.8 Hz, 1H), 7.49 (s, 1H), 7.06-7.04 (m, 1H), 5.57-5.50 (m, 1H), 3.72-3.69 (m, 2H), 3.43-3.40 (m, 2H), 1.86-1.83 (m, 2H), 1.73-1.63 (m, 12H). |
| I-148 | azepane-carbonyl-pyridinyl (methyl) | HOCH₂-CH(CH₃)- | 465.2 | CD₃OD-d₄: δ 8.84 (s, 1H), 8.38 (d, J = 5.2 Hz, 1H), 8.09 (d, J = 8.4 Hz, 1H), 7.99-7.95 (m, 1H), 7.77 (d, J = 7.6 Hz, 1H), 7.49 (s, 1H), 7.05 (d, J = 4.4 Hz, 1H), 5.54-5.46 (m, 1H), 3.97-3.86 (m, 2H), 3.72-3.69 (m, 2H), 3.43-3.40 (m, 2H), 1.86-1.83 (m, 2H), 1.71-1.61 (m, 9H). |
| I-149 | azabicyclic-carbonyl-pyridinyl (methyl) | isopropyl | 461.3 | CD₃OD-d₄: δ 8.87 (s, 1H), 8.37 (d, J = 5.2 Hz, 1H), 8.13-8.10 (m, 1H), 7.99-7.95 (m, 1H), 7.77 (d, J = 7.2 Hz, 1H), 7.58 (s, 1H), 7.12 (d, J = 4.8 Hz, 1H), 5.57-5.50 (m, 1H), 4.76-4.72 (m, 1H), 4.05-4.00 (m, 1H), 2.09-2.02 (m, 2H), 1.93-1.75 (m, 5H), 1.68-1.55 (m, 9H). |
| I-150 | azabicyclic-carbonyl-pyridinyl (methyl) | HOCH₂-CH(CH₃)- | 477.2 | DMSO-d₆: δ 10.77 (s, 1H), 10.10 (s, 1H), 8.79 (s, 1H), 8.35 (d, J = 5.2 Hz, 1H), 8.04 (d, J = 8.4 Hz, 1H), 7.98-7.94 (m, 1H), 7.74 (d, J = 7.6 Hz, 1H), 7.66 (s, 1H), 7.09 (d, J = 5.2 Hz, 1H), 5.35-5.30 (m, 1H), 5.06-5.03 (m, 1H), 4.61-4.55 (m, 1H), 3.93-3.89 (m, 1H), 3.73-3.70 (m, 2H), 1.94-1.90 (m, 2H), 1.76-1.72 (m, 4H), 1.64-1.55 (m, 7H). |

TABLE 1-continued
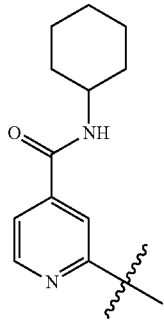 [SMILES: *c1cc(C(=O)NC2CCCCC2)ccn1]
| Compound | R₁ | R₂ | LC-MS (M + H)⁺ | ¹HNMR (ppm) |
|---|---|---|---|---|
| I-151 | 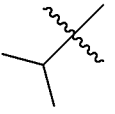 [SMILES: *C(C)C] | 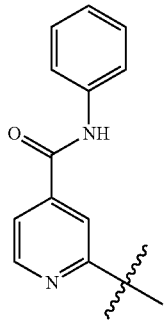 [SMILES: *c1cc(C(=O)Nc2ccccc2)ccn1] | 449.2 | CD₃OD-d₄: δ 8.86 (s, 1H), 8.36-8.34 (m, 1H), 8.12 (d, J = 8.0 Hz, 1H), 7.98-7.94 (m, 1H), 7.76-7.74 (m, 2H), 7.35-7.33 (m, 1H), 5.54-5.47 (m, 1H), 3.89-3.83 (m, 1H), 2.00-1.95 (m, 2H), 1.85-1.81 (m, 2H), 1.72-1.68 (m, 1H), 1.62 (d, J = 6.8 Hz, 6H), 1.45-1.35 (m, 5H). |
| I-152 |  | 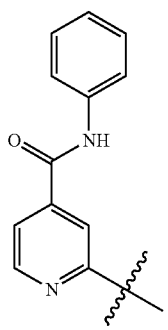 [SMILES: *c1cc(C(=O)Nc2ccccc2)ccn1] | 443.2 | DMSO-d₆: δ 10.71 (s, 1H), 10.54 (s, 1H), 10.19 (s, 1H), 8.91 (s, 1H), 8.45 (d, J = 5.2 Hz, 1H), 8.10-8.06 (m, 2H), 8.00-7.96 (m, 1H), 7.78-7.74 (m, 3H), 7.53-7.51 (m, 1H), 7.41-7.37 (m, 2H), 7.17-7.13 (m, 1H), 5.44-5.37 (m, 1H), 1.54 (d, J = 6.8 Hz, 6H). |
| I-153 | 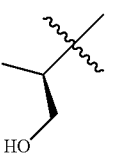 [SMILES: *[C@H](C)CO] | 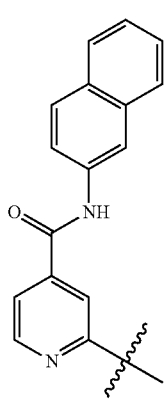 [SMILES: *c1cc(C(=O)Nc2ccc3ccccc3c2)ccn1] | 459.3 | CD₃OD-d₄: δ 8.83 (s, 1H), 8.44 (d, J = 5.2 Hz, 1H), 8.10 (d, J = 8.4 Hz, 1H), 7.98-7.94 (m, 1H), 7.90 (s, 1H), 7.77-7.75 (m, 1H), 7.70 (d, J = 7.6 Hz, 2H), 7.49-7.47 (m, 1H), 7.40-7.36 (m, 2H), 7.20-7.16 (m, 1H), 5.49-5.46 (m, 1H), 3.95-3.85 (m, 2H), 1.64 (d, J = 7.2 Hz, 3H). |
| I-154 |  | | 493.3 | DMSO-d₆: δ 10.75 (s, 2H), 10.22 (s, 1H), 8.91 (s, 1H), 8.48-8.45 (m, 2H), 8.15 (s, 1H), 8.08 (d, J = 8.4 Hz, 1H), 8.03-7.90 (m, 4H), 7.88-7.77 (m, 2H), 7.59-7.52 (m, 1H), 7.50-7.44 (m, 2H), 5.43-5.39 (m, 1H), 1.54 (d, J = 6.8 Hz, 6H). |

TABLE 1-continued
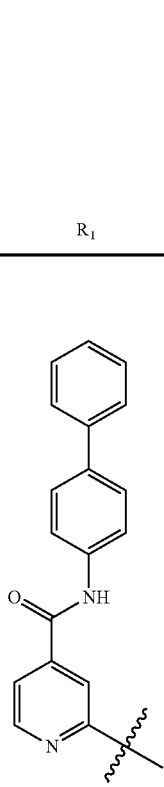
| Compound | R₁ | R₂ | LC-MS (M + H)⁺ | ¹HNMR (ppm) |
|---|---|---|---|---|
| I-155 |  | 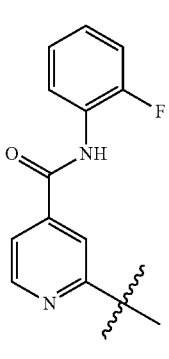 [SMILES: *c1cc(C(=O)Nc2ccccc2F)ccn1] | 519.4 | DMSO-d₆: δ 10.72 (s, 1H), 10.66 (s, 1H), 10.22 (s, 1H), 8.96 (s, 1H), 8.47 (d, J = 5.1 Hz, 1H), 8.13-8.08 (m, 2H), 8.02-7.97 (m, 1H), 7.91-7.85 (m, 2H), 7.78-7.64 (m, 5H), 7.56-7.54 (m, 1H), 7.50-7.45 (m, 2H), 7.38-7.33 (m, 1H), 5.46-5.37 (m, 1H), 1.55 (d, J = 6.6 Hz, 6H). |
| I-156 | 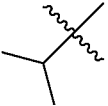 [SMILES: *C(C)C] | 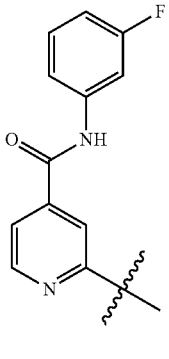 [SMILES: *c1cc(C(=O)Nc2cccc(F)c2)ccn1] | 461.3 | DMSO-d₆: δ 10.69 (s, 1H), 10.45 (s, 1H), 10.20 (s, 1H), 8.91 (s, 1H), 8.46-8.44 (m, 1H), 8.14 (s, 1H), 8.07 (d, J = 8.0 Hz, 1H), 8.00-7.96 (m, 1H), 7.75 (d, J = 7.2 Hz, 1H), 7.62 (s, 1H), 7.54 (d, J = 4.0 Hz, 1H), 7.34-7.25 (m, 3H), 5.42-5.39 (m, 1H), 1.54 (d, J = 6.8 Hz, 6H). |
| I-157 | 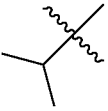 [SMILES: *C(C)C] | 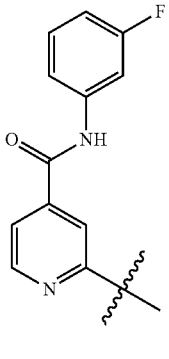 [SMILES: *c1cc(C(=O)Nc2cccc(F)c2)ccn1] | 461.2 | DMSO-d₆: δ 10.74 (s, 1H), 10.66 (s, 1H), 10.21 (s, 1H), 8.91 (s, 1H), 8.47 (d, J = 5.4 Hz, 1H), 8.11-8.06 (m, 2H), 8.01-7.95 (m, 1H), 7.77-7.71 (m, 2H), 7.58-7.51 (m, 2H), 7.47-7.39 (m, 1H), 7.02-6.96 (m, 1H), 5.43-5.38 (m, 1H), 1.54 (d, J = 6.9 Hz, 6H). |

TABLE 1-continued
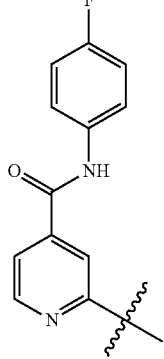
| Compound | R₁ | R₂ | LC-MS (M + H)⁺ | ¹HNMR (ppm) |
|---|---|---|---|---|
| I-158 | 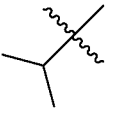 [SMILES: *C(C)C] | 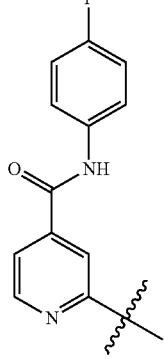 | 461.2 | DMSO-d₆: δ 10.70 (s, 1H), 10.61 (s, 1H), 10.21 (s, 1H), 8.92 (s, 1H), 8.46 (d, J = 5.1 Hz, 1H), 8.14-8.04 (m, 2H), 8.01-7.95 (m, 1H), 7.82-7.75 (m, 3H), 7.53-7.51 (m, 1H), 7.27-7.21 (m, 2H), 5.45-5.36 (m, 1H), 1.54 (d, J = 6.6 Hz, 6H). |
| I-159 | 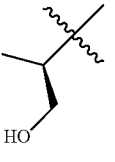 [SMILES: *[C@H](C)CO] | 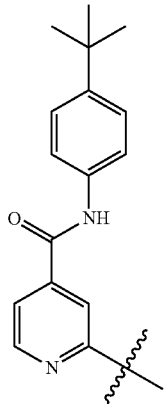 [SMILES: *c1cc(C(=O)Nc2ccc(C(C)(C)C)cc2)ccn1] | 477.2 | CD₃OD-d₄: δ 8.85 (s, 1H), 8.47 (d, J = 4.8 Hz, 1H), 8.11 (d, J = 8.4 Hz, 1H), 8.00-7.93 (m, 2H), 7.79-7.71 (m, 3H), 7.49 (d, J = 4.0 Hz, 1H), 7.16-7.12 (m, 2H), 5.54-5.50 (m, 2H), 3.97-3.87 (m, 2H), 1.66 (d, J = 6.8 Hz, 3H). |
| I-160 | 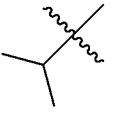 [SMILES: *C(C)C] | 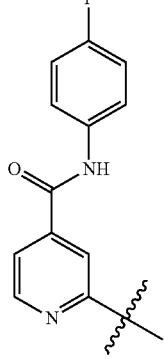 | 499.3 | DMSO-d₆: δ 10.74 (s, 1H), 10.47 (s, 1H), 10.19 (s, 1H), 8.91 (s, 1H), 8.44 (d, J = 5.2 Hz, 1H), 8.07 (d, J = 8.4 Hz, 2H), 8.00-7.96 (m, 1H), 7.76-7.74 (m, 1H), 7.67 (d, J = 8.8 Hz, 2H), 7.52 (s, 1H), 7.41-7.39 (m, 2H), 5.42-5.39 (m, 1H), 1.54 (d, J = 6.8 Hz, 6H), 1.28 (s, 9H). |

TABLE 1-continued

| Compound | R₁ | R₂ | LC-MS (M + H)⁺ | ¹HNMR (ppm) |
|---|---|---|---|---|
| I-161 | pyridin-2-yl-C(O)NH-pyridin-2-yl (nicotinamide linked) | isopropyl | 444.1 | DMSO-d₆: δ 11.14 (s, 1H), 10.79 (s, 1H), 10.21 (s, 1H), 8.92 (s, 1H), 8.43 (d, J = 5.4 Hz, 2H), 8.21-8.19 (m, 1H), 8.15-8.04 (m, 2H), 8.02-8.19 (m, 1H), 7.92-7.86 (m, 1H), 7.76 (d, J = 7.5 Hz, 1H), 7.60-7.58 (m, 1H), 7.24-7.20 (m, 1H), 5.43-5.39 (m, 1H), 1.54 (d, J = 6.6 Hz, 6H). |
| I-162 | pyridin-3-yl-NHC(O)- nicotinamide | isopropyl | 444.2 | DMSO-d₆: δ 10.76 (s, 1H), 10.64 (s, 1H), 10.22 (s, 1H), 8.93 (d, J = 2.4 Hz, 1H), 8.91 (s, 1H), 8.47 (d, J = 5.4 Hz, 1H), 8.37-8.35 (m, 1H), 8.20-8.15 (m, 2H), 8.07 (d, J = 8.1 Hz, 1H), 8.01-7.95 (m, 1H), 7.75 (d, J = 7.5 Hz, 1H), 7.55 (d, J = 5.1 Hz, 1H), 7.46-7.42 (m, 1H), 5.43-5.38 (m, 1H), 1.54 (d, J = 6.6 Hz, 6H). |
| I-163 | pyridin-4-yl-NHC(O)- nicotinamide | isopropyl | 444.1 | DMSO-d₆: δ 10.90 (s, 1H), 10.60 (s, 1H), 10.22 (s, 1H), 8.91 (s, 1H), 8.52 (s, 2H), 8.48 (d, J = 5.2 Hz, 1H), 8.13 (s, 1H), 8.07 (d, J = 8.0 Hz, 1H), 8.00-7.96 (m, 1H), 7.79-7.74 (m, 3H), 7.53-7.52 (m, 1H), 5.42-5.38 (m, 1H), 1.52 (d, J = 6.8 Hz, 6H). |
| I-164 | pyridin-4-yl-NHC(O)- nicotinamide | 1-hydroxypropan-2-yl | 460.1 | CD₃OD-d₄: δ 8.84 (s, 1H), 8.50-8.40 (m, 3H), 8.09 (d, J = 8.0 Hz, 1H), 7.98-7.94 (m, 2H), 7.84 (d, J = 4.0 Hz, 2H), 7.77-7.75 (m, 1H), 7.50-7.48 (m, 1H), 5.50-5.46 (m, 1H), 3.94-3.85 (m, 2H), 1.64 (d, J = 6.8 Hz, 3H). |

TABLE 1-continued

| Compound | R₁ | R₂ | LC-MS (M + H)⁺ | ¹HNMR (ppm) |
|---|---|---|---|---|
| I-165 | 5-(pyrrolidin-1-yl)pyridin-2-yl | isopropyl | 393.3 | DMSO-d₆: δ 9.60 (s, 1H), 8.89 (s, 1H), 8.04 (d, J = 8.4 Hz, 1H), 7.95-7.90 (m, 1H), 7.69 (d, J = 6.9 Hz, 1H), 7.57 (d, J = 2.7 Hz, 1H), 7.44 (d, J = 2.4 Hz, 1H), 7.09-7.06 (m, 1H), 5.43-5.34 (m, 1H), 3.24-3.20 (m, 4H), 1.98-1.90 (m, 4H), 1.52 (d, J = 6.6 Hz, 6H). |
| I-166 | 6-(pyrrolidin-1-yl)pyridin-2-yl | isopropyl | 393.3 | DMSO-d₆: δ 11.88 (s, 1H), 8.89 (s, 1H), 8.51 (s, 1H), 8.07 (d, J = 8.0 Hz, 1H), 7.99-7.91 (m, 2H), 7.75 (d, J = 7.2 Hz, 1H), 7.51-7.49 (m, 1H), 7.11-7.08 (m, 1H), 5.39-5.35 (m, 1H), 3.16-3.09 (m, 4H), 1.92-1.89 (m, 4H), 1.54 (d, J = 6.8 Hz, 6H). |
| I-167 | 4-(pyrrolidin-1-yl)pyridin-2-yl | isopropyl | 393.1 | DMSO-d₆: δ 9.56 (s, 1H), 8.88 (s, 1H), 8.09 (d, J = 8.4 Hz, 1H), 7.95-7.91 (m, 1H), 7.80 (d, J = 6.0 Hz, 1H), 7.72 (d, J = 7.2 Hz, 1H), 6.38 (s, 1H), 6.26-6.24 (m, 1H), 5.43-5.36 (m, 1H), 3.30-3.24 (m, 4H), 1.98-1.95 (m, 4H), 1.55 (d, J = 6.8 Hz, 6H). |
| I-168 | 5-(1H-imidazol-1-yl)pyridin-2-yl | isopropyl | 390.3 | DMSO-d₆: δ 9.74 (s, 1H), 9.48 (s, 1H), 8.90 (s, 1H), 8.57 (s, 1H), 8.47 (s, 1H), 8.19 (s, 1H), 8.00-7.91 (m, 3H), 7.81-7.71 (m, 2H), 7.12 (s, 1H), 5.50-5.45 (m, 1H), 1.48 (d, J = 6.6 Hz, 6H). |
| I-169 | 5-(4-cyclopropyl-1H-imidazol-1-yl)pyridin-2-yl | isopropyl | 430.2 | DMSO-d₆: δ 10.28 (s, 1H), 10.09 (s, 1H), 8.90 (s, 1H), 8.54 (d, J = 2.4 Hz, 1H), 8.07-8.03 (m, 3H), 7.99-7.94 (m, 1H), 7.86 (d, J = 9.0 Hz, 1H), 7.75-7.72 (m, 1H), 7.48 (d, J = 1.2 Hz, 1H), 5.40-5.36 (m, 1H), 1.87-1.81 (m, 1H), 1.52 (d, J = 6.6 Hz, 6H), 0.83-0.81 (m, 2H), 0.80-0.77 (m, 2H). |
| I-170 | 5-(5-cyclopropyl-1H-imidazol-1-yl)pyridin-2-yl | isopropyl | 430.4 | DMSO-d₆: δ 10.65 (s, 1H), 10.07 (s, 1H), 8.89 (s, 1H), 8.30 (d, J = 5.7 Hz, 1H), 8.23 (d, J = 1.2 Hz, 1H), 8.07-8.04 (m, 1H), 7.98-7.93 (m, 1H), 7.79-7.72 (m, 2H), 7.52 (d, J = 1.2 Hz, 1H), 7.37-7.35 (m, 1H), 5.40-5.36 (m, 1H), 1.90-1.85 (s, 1H), 1.51 (d, J = 6.9 Hz, 6H), 0.84-0.69 (m, 4H). |

TABLE 1-continued

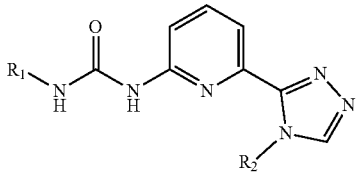

| Compound | R₁ | R₂ | LC-MS (M + H)⁺ | ¹HNMR (ppm) |
|---|---|---|---|---|
| I-171 |  | 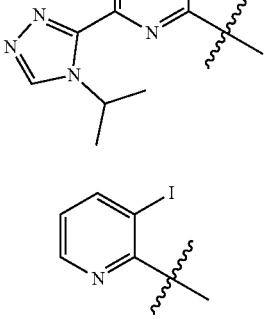 | 433.1 | DMSO-d₆: δ 9.87 (s, 2H), 8.88 (s, 2H), 8.06-8.04 (m, 2H), 8.00-7.96 (m, 2H), 7.73-7.70 (m, 2H), 5.37-5.30 (m, 2H), 1.43 (d, J = 6.8 Hz, 12H). |
| I-172 |  | 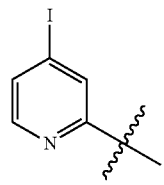 [SMILES: *c1cc(I)ccn1] | 450.0 | DMSO-d₆: δ 11.30 (s, 1H), 8.90 (s, 1H), 8.54 (s, 1H), 8.37-8.34 (m, 2H), 8.05-8.03 (m, 1H), 8.00-7.96 (m, 1H), 7.78-7.76 (m, 1H), 7.00-6.97 (m, 1H), 5.41-5.34 (m, 1H), 1.53 (d, J = 6.8 Hz, 6H). |
| I-173 |  | 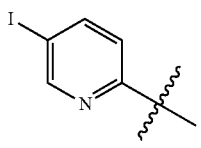 [SMILES: *c1ccc(I)cn1] | 449.9 | DMSO-d₆: δ 10.65 (s, 1H), 10.03 (s, 1H), 8.90 (s, 1H), 8.12 (s, 1H), 8.05-8.03 (m, 1H), 8.00-7.95 (m, 2H), 7.75 (d, J = 6.8 Hz, 1H), 7.48-7.46 (m, 1H), 5.40-5.37 (m, 1H), 1.52 (d, J = 6.8 Hz, 6H). |
| I-174 |  | 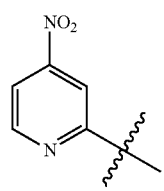 [SMILES: *c1cc([N+](=O)[O-])ccn1] | 450.1 | DMSO-d₆: δ 10.32 (s, 1H), 10.03 (s, 1H), 8.90 (s, 1H), 8.47-8.46 (d, J = 4.0 Hz, 1H), 8.13-8.10 (m, 1H), 8.04-8.02 (d, J = 8.0 Hz, 1H), 7.99-7.95 (m, 1H), 7.75-7.73 (d, J = 8.0 Hz, 1H), 7.65-7.62 (d, J = 12.0 Hz, 1H), 5.41-5.35 (m, 1H), 1.53-1.51 (d, J = 8.0 Hz, 6H). |
| I-175 |  | 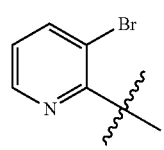 | 368.9 | DMSO-d₆: δ 10.45 (s, 1H), 10.16 (s, 1H), 8.91 (s, 1H), 8.62 (d, J = 5.6 Hz, 1H), 8.55 (d, J = 2.0 Hz, 1H), 8.07-7.97 (m, 2H), 7.78-7.76 (m, 2H), 5.42-5.39 (m, 1H), 1.52 (d, J = 6.4 Hz, 6H). |
| I-176 |  | 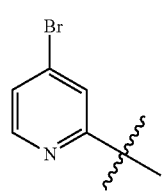 [SMILES: *c1cc(Cl)ccn1] | 402.1 404.1 | DMSO-d₆: δ 11.39 (s, 1H), 8.91 (s, 2H), 8.36 (d, J = 4.4 Hz, 1H), 8.20 (d, J = 8.0 Hz, 1H), 8.07 (d, J = 8.4 Hz, 1H), 8.01-7.97 (m, 1H), 7.78 (d, J = 7.2 Hz, 1H), 7.17-7.13 (m, 1H), 5.39-5.36 (m, 1H), 1.54 (d, J = 6.4 Hz, 6H). |
| I-177 |  | | 402.0 | DMSO-d₆: δ 10.54 (s, 1H), 10.12 (s, 1H), 8.89 (s, 1H), 8.18 (d, J = 5.6 Hz, 1H), 8.05-8.03 (m, 1H), 8.00-7.94 (m, 2H), 7.76-7.74 (m, 1H), 7.33-7.31 (m, 1H), 5.40-5.37 (m, 1H), 1.52 (d, J = 6.4 Hz, 6H). |

… TABLE 1-continued

| Compound | R₁ | R₂ | LC-MS (M + H)⁺ | ¹HNMR (ppm) |
|---|---|---|---|---|
| I-178 | 5-Br-pyridin-2-yl | isopropyl | 402.0 | CD₃OD-d₄: δ 8.89 (s, 1H), 8.09-8.07 (d, J = 8.0 Hz, 1H), 7.99-7.91 (m, 2H), 7.87-7.86 (m, 1H), 7.76-7.75 (d, J = 4.0 Hz, 1H), 7.56-7.55 (m, 1H), 5.68-5.52 (m, 1H), 1.63-1.62 (d, J = 4.0 Hz, 6H). |
| I-179 | 6-Br-pyridin-2-yl | isopropyl | 402.1 | DMSO-d₆: δ 10.22 (s, 1H), 9.98 (s, 1H), 9.23-9.22 (m, 1H), 8.10-8.02 (m, 1H), 8.01-7.99 (m, 1H), 7.84-7.72 (m, 3H), 7.31-7.29 (m, 1H), 5.55-5.48 (m, 1H), 1.53 (d, J = 6.8 Hz, 6H). |
| I-180 | 3-Cl-pyridin-2-yl | isopropyl | 358.1 | DMSO-d₆: δ 11.59 (s, 1H), 9.19 (s, 1H), 8.91 (s, 1H), 8.32 (d, J = 4.4 Hz, 1H), 8.09-7.97 (m, 3H), 7.79 (d, J = 7.2 Hz, 1H), 7.23-7.20 (m, 1H), 5.41-5.35 (m, 1H), 1.55 (d, J = 6.4 Hz, 6H). |
| I-181 | 4-Cl-pyridin-2-yl | isopropyl | 357.9 | DMSO-d₆: δ 10.52 (s, 1H), 10.15 (s, 1H), 8.90 (s, 1H), 8.27 (d, J = 5.6 Hz, 1H), 8.03-8.02 (m, 1H), 8.00-7.98 (m, 1H), 7.80-7.75 (m, 2H), 7.22-7.20 (m, 1H), 5.42-5.36 (m, 1H), 1.52 (d, J = 6.8 Hz, 6H). |
| I-182 | 4-Cl-pyridin-2-yl | (S)-1-hydroxypropan-2-yl | 374.2 | DMSO-d₆: δ 10.52 (s, 1H), 10.14 (s, 1H), 8.79 (s, 1H), 8.28-8.24 (m, 1H), 8.04-7.90 (m, 2H), 7.78-7.73 (m, 2H), 7.21-7.17 (m, 1H), 5.34-5.29 (m, 1H), 5.05-5.02 (m, 1H), 3.71-3.68 (m, 2H), 1.50 (d, J = 7.2 Hz, 3H). |
| I-183 | 4-Cl-pyridin-2-yl | (R)-1-hydroxypropan-2-yl | 374.2 | DMSO-d₆: δ 10.52 (s, 1H), 10.14 (s, 1H), 8.79 (s, 1H), 8.27 (d, J = 5.2 Hz, 1H), 8.04-8.02 (m, 1H), 7.99-7.95 (m, 1H), 7.79-7.73 (m, 2H), 7.21-7.19 (m, 1H), 5.34-5.33 (m, 1H), 5.05-5.02 (m, 1H), 3.72-3.69 (m, 2H), 1.50 (d, J = 6.8 Hz, 3H). |
| I-184 | 5-Cl-pyridin-2-yl | isopropyl | 358.3 | CD₃OD-d₄: δ 8.87 (s, 1H), 8.25 (s, 1H), 8.10-8.08 (d, J = 8.0 Hz, 1H), 8.03-7.95 (m, 1H), 7.82-7.75 (m, 2H), 7.62-7.60 (m, 1H), 5.54-5.47 (m, 1H), 1.64-1.62 (d, J = 8.0 Hz, 6H). |
| I-185 | 6-Cl-pyridin-2-yl | isopropyl | 358.1 | DMSO-d₆: δ 10.19 (s, 1H), 9.97 (s, 1H), 8.90-8.89 (m, 1H), 8.06-8.04 (m, 1H), 8.00-7.96 (m, 1H), 7.88-7.84 (m, 1H), 7.79-7.75 (m, 2H), 7.18-7.16 (m, 1H), 5.49-5.45 (m, 1H), 1.51 (d, J = 6.4 Hz, 6H). |

TABLE 1-continued
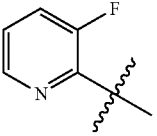 [SMILES: *c1ncccc1F]
| Compound | R₁ | R₂ | LC-MS (M + H)⁺ | ¹HNMR (ppm) |
|---|---|---|---|---|
| I-186 | 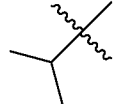 [SMILES: *C(C)C] | 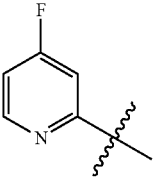 [SMILES: *c1cc(F)ccn1] | 342.0 | DMSO-d₆: δ 11.72 (s, 1H), 9.82 (s, 1H), 8.90 (s, 1H), 8.15-8.10 (m, 2H), 8.00-7.96 (m, 1H), 7.83-7.78 (m, 2H), 7.23-7.19 (m, 1H), 5.43-5.36 (m, 1H), 1.57 (d, J = 6.8 Hz, 6H). |
| I-187 | 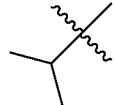 | 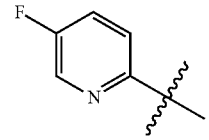 | 342.2 | DMSO-d₆: δ 8.89 (s, 1H), 8.33-8.29 (m, 1H), 8.05-8.03 (m, 1H), 7.99-7.95 (m, 1H), 7.76-7.74 (m, 1H), 7.53-7.50 (m, 1H), 7.03-6.99 (m, 1H), 5.44-5.37 (m, 1H), 1.52 (d, J = 6.4 Hz, 6H). |
| I-188 | 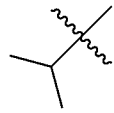 [SMILES: *C(C)C] | 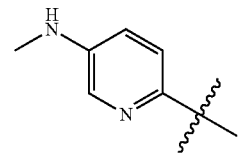 [SMILES: *c1ccc(NC)cn1] | 342.2 | DMSO-d₆: δ 10.26 (s, 1H), 10.02 (s, 1H), 8.89 (s, 1H), 8.27-8.27 (d, J = 1.2 Hz, 1H), 8.04-7.93 (m, 2H), 7.80-7.72 (m, 3H), 5.41-5.36 (m, 1H), 1.53-1.50 (d, J = 12.0 Hz, 6H). |
| I-189 | 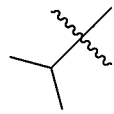 [SMILES: *C(C)C] | 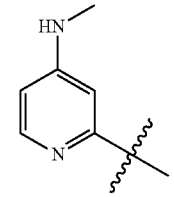 [SMILES: *c1cc(NC)ccn1] | 353.2 | DMSO-d₆: δ 9.59 (s, 1H), 8.89 (s, 1H), 8.04 (d, J = 8.4 Hz, 1H), 7.95-7.91 (m, 1H), 7.70 (d, J = 7.2 Hz, 1H), 7.60 (d, J = 2.8 Hz, 1H), 7.33 (s, 1H), 7.06-7.03 (m, 1H), 5.67-5.63 (m, 1H), 5.44-5.37 (m, 1H), 2.69 (d, J = 4.8 Hz, 3H), 1.53 (d, J = 6.4 Hz, 6H). |
| I-190 | 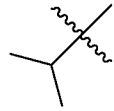 [SMILES: *C(C)C] | 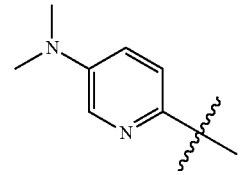 [SMILES: *c1ccc(N(C)C)cn1] | 353.0 | DMSO-d₆: δ 9.56 (s, 1H), 8.88 (s, 1H), 8.18 (s, 1H), 8.09 (d, J = 8.4 Hz, 1H), 7.95-7.91 (m, 1H), 7.74-7.71 (m, 2H), 6.74-6.73 (m, 1H), 6.36 (s, 1H), 6.25-6.23 (m, 1H), 5.42-5.36 (m, 1H), 2.69 (d, J = 4.8 Hz, 3H), 1.54 (d, J = 6.4 Hz, 6H). |
| I-191 | 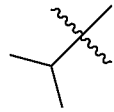 [SMILES: *C(C)C] | 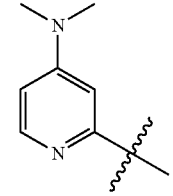 [SMILES: *c1cc(N(C)C)ccn1] | 367.1 | DMSO-d₆: δ 10.76 (s, 1H), 9.66 (s, 1H), 8.90 (s, 1H), 8.05-8.03 (m, 1H), 7.96-7.92 (m, 1H), 7.75-7.69 (m, 2H), 7.47 (s, 1H), 7.32-7.29 (m, 1H), 5.42-5.36 (m, 1H), 2.88 (s, 6H), 1.54 (d, J = 6.8 Hz, 6H). |
| I-192 | 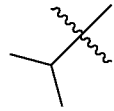 [SMILES: *C(C)C] | | 367.2 | DMSO-d₆, ppm): δ 9.89 (s, 1H), 8.27-8.26 (m, 1H), 8.12-8.08 (m, 1H), 7.94-7.92(m, 1H), 7.87-7.85(m, 1H), 6.83-6.80 (m, 1H), 6.43-6.42 (m, 1H), 5.90-5.84 (m, 1H), 3.33-3.32 (m, 6H), 1.69 (d, J = 6.8 Hz, 6H). |

TABLE 1-continued

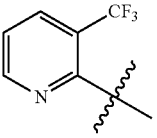 [SMILES: *c1ncccc1C(F)(F)F]

| Compound | R₁ | R₂ | LC-MS (M + H)⁺ | ¹HNMR (ppm) |
|---|---|---|---|---|
| I-193 | 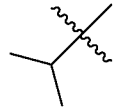 [SMILES: *C(C)C] | 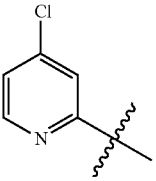 | 392.0 | DMSO-d₆: δ 10.52 (s, 1H), 9.17 (s, 1H), 8.89 (s, 1H), 8.69 (d, J = 4.0 Hz, 1H), 8.25 (d, J = 6.8 Hz, 1H), 7.97 (d, J = 4.4 Hz, 2H), 7.75-7.73 (m, 1H), 7.47-7.44 (m, 1H), 5.40-5.34 (m, 1H), 1.49 (d, J = 6.8 Hz, 6H). |
| I-194 |  | 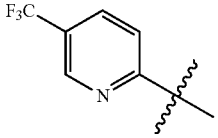 [SMILES: *c1ccc(C(F)(F)F)cn1] | 392.2 | DMSO-d₆: δ 10.30 (brs, 2H), 8.91-8.90 (m, 1H), 8.56-8.55(m, 1H), 8.13-8.12 (m, 1H), 8.07-8.05 (m, 1H), 7.99-7.96 (m, 1H), 7.77-7.76 (m, 1H), 7.43-7.42 (m, 1H), 5.44-5.37 (m, 1H), 1.52 (d, J = 6.4 Hz, 6H). |
| I-195 | 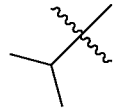 [SMILES: *C(C)C] | 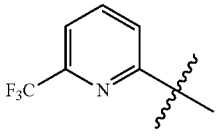 [SMILES: *c1cccc(C(F)(F)F)n1] | 392.2 | DMSO-d₆: δ 10.34 (s, 1H), 10.27 (s, 1H), 8.90 (s, 1H), 8.65 (s, 1H), 8.20-8.17 (m, 1H), 8.05 (d, J = 7.2 Hz, 1H), 8.01-7.97 (m, 2H), 8.78-7.76 (m, 1H), 5.41-5.38 (m, 1H), 1.52 (d, J = 6.4 Hz, 6H). |
| I-196 | 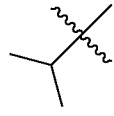 [SMILES: *C(C)C] | 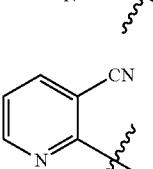 | 392.1 | DMSO-d₆: δ 10.30 (s, 1H), 9.88 (s, 1H), 8.89 (s, 1H), 8.10-8.05 (m, 3H), 8.00-7.96 (m, 1H), 7.79-7.77 (m, 1H), 7.56-7.54 (m, 1H), 5.50-5.43 (m, 1H), 1.49 (d, J = 6.8 Hz, 6H). |
| I-197 | 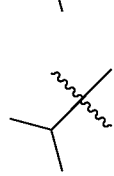 | 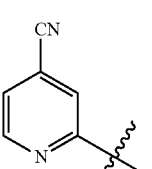 | 349.0 | DMSO-d₆: δ 11.51 (s, 1H), 9.22 (s, 1H), 8.86 (s, 1H), 8.60-8.42 (m, 2H), 8.30-8.10 (m, 2H), 7.70-7.50 (m, 1H), 7.40-7.25 (m, 1H), 5.31-5.13 (m, 1H), 1.41 (d, J = 6.3 Hz, 6H). |
| I-198 | 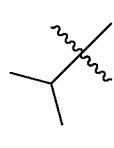 [SMILES: *C(C)C] | 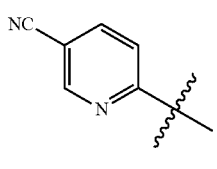 [SMILES: *c1ccc(C#N)cn1] | 349.3 | DMSO-d₆: δ 10.29 (s, 1H), 10.20 (s, 1H), 8.90 (s, 1H), 8.52 (d, J = 5.2 Hz, 1H), 8.10 (s, 1H), 8.04-7.97 (m, 2H), 7.77-7.75 (m, 1H), 7.51-7.50 (m, 1H), 5.42-5.36 (m, 1H), 1.51 (d, J = 6.8 Hz, 6H). |
| I-199 | 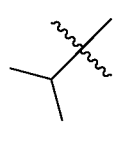 [SMILES: *C(C)C] | 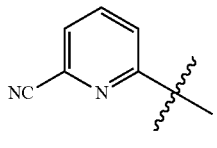 [SMILES: *c1cccc(C#N)n1] | 349.2 | DMSO-d₆: δ 10.68 (s, 1H), 10.56 (s, 1H), 9.53 (s, 1H), 8.74-8.73 (d, J = 1.2 Hz, 1H), 8.25-8.22 (m, 1H), 8.15-8.12 (d, J = 12.0 Hz, 1H), 8.06-8.02 (m, 1H), 7.96-7.94 (d, J = 8.0 Hz, 1H), 7.83-7.81 (d, J = 8.0 Hz, 1H), 5.60-5.53 (m, 1H), 1.57-1.56 (d, J = 4.0 Hz, 6H). |
| I-200 | 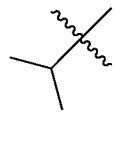 [SMILES: *C(C)C] | | 349.3 | DMSO-d₆: δ 10.34 (s, 1H), 10.00 (s, 1H), 8.89 (s, 1H), 8.10-7.96 (m, 4H), 7.78 (d, J = 7.2 Hz, 1H), 7.70 (d, J = 7.2 Hz, 1H), 5.47-5.41 (m, 1H), 1.51 (d, J = 6.4 Hz, 6H). |

TABLE 1-continued

| Compound | R₁ | R₂ | LC-MS (M + H)⁺ | ¹HNMR (ppm) |
|---|---|---|---|---|
| I-201 | 3-carboxy-pyridin-2-yl (with methyl at attachment) | isopropyl | 368.2 | CD₃OD-d₄: δ 8.88 (s, 1H), 8.48-8.45 (m, 1H), 8.33-8.31 (m, 1H), 8.28-8.26 (m, 1H), 7.99-7.95 (m, 1H), 7.80-7.78 (m, 1H), 7.12-7.09 (m, 1H), 5.59-5.53 (m, 1H), 1.70 (d, J = 6.8 Hz, 6H). |
| I-202 | 4-carboxy-pyridin-2-yl (with methyl at attachment) | isopropyl | 368.1 | DMSO-d₆: δ 10.09 (s, 1H), 8.89 (s, 1H), 8.34-8.33 (m, 1H), 8.15-8.07 (m, 2H), 7.99-7.95 (m, 1H), 7.75 (d, J = 7.6 Hz, 1H), 7.43 (d, J = 4.4 Hz, 1H), 5.42-5.39 (m, 1H), 1.54 (d, J = 6.4 Hz, 6H). |
| I-203 | 4-(2-hydroxypropan-2-yl)pyridin-2-yl (with methyl at attachment) | isopropyl | 402.1 | DMSO-d₆: δ 10.45 (s, 1H), 10.30 (s, 1H), 8.90 (s, 1H), 8.73 (d, J = 2.1 Hz, 1H), 8.30-8.26 (m, 1H), 8.07-7.97 (m, 3H), 7.79-7.76 (m, 1H), 5.42-5.38 (m, 1H), 3.28 (s, 3H), 1.52 (d, J = 6.6 Hz, 6H). |
| I-204 | 4-(methylsulfonyl)pyridin-2-yl (with methyl at attachment) | isopropyl | 402.2 | DMSO-d₆: δ 10.37 (s, 1H), 10.27 (s, 1H), 8.91 (s, 1H), 8.58 (d, J = 5.4 Hz, 1H), 8.29 (s, 1H), 8.08-7.96 (m, 2H), 7.78-7.75 (m, 1H), 7.58-7.56 (m, 1H), 5.42-5.38 (m, 1H), 1.52 (d, J = 6.6 Hz, 6H). |
| I-205 | 4-sulfamoylpyridin-2-yl (with methyl at attachment) | isopropyl | 403.2 | DMSO-d₆: δ 10.42 (s, 1H), 10.31 (s, 1H), 8.90 (s, 1H), 8.50 (d, J = 5.4 Hz, 1H), 8.20 (s, 1H), 8.07-7.96 (m, 2H), 7.87-7.75 (m, 3H), 7.43-7.40 (m, 1H), 5.45-5.36 (m, 1H), 1.53 (d, J = 6.6 Hz, 6H). |
| I-206 | 4-(piperidin-1-ylsulfonyl)pyridin-2-yl (with methyl at attachment) | isopropyl | 471.2 | DMSO-d₆: δ 10.29 (s, 2H), 8.91 (s, 1H), 8.55 (d, J = 4.8 Hz, 1H), 8.10-7.95 (m, 3H), 7.76 (d, J = 6.9 Hz, 1H), 7.33-7.31 (m, 1H), 5.43-5.38 (m, 1H), 3.01-2.97 (m, 4H), 1.56-1.40 (m, 12H). |

TABLE 1-continued

| Compound | R₁ | R₂ | LC-MS (M + H)⁺ | ¹HNMR (ppm) |
|---|---|---|---|---|
| I-207 | morpholine-sulfonyl-pyridin-2-yl | isopropyl | 473.2 | DMSO-d₆: δ 10.32 (s, 1H), 10.26 (s, 1H), 8.91 (s, 1H), 8.58 (d, J = 5.4 Hz, 1H), 8.12-8.01 (m, 2H), 7.98-7.95 (m, 1H), 7.78-7.75 (m, 1H), 7.34-7.32 (m, 1H), 5.45-5.36 (m, 1H), 3.68-3.65 (m, 4H), 3.00-2.97 (m, 4H), 1.52 (d, J = 6.9 Hz, 6H). |
| I-208 | 5-(hydroxymethyl)pyridin-2-yl | isopropyl | 354.2 | DMSO-d₆: δ 11.11 (s, 1H), 9.98 (s, 1H), 8.90 (s, 1H), 8.19 (d, J = 2.0 Hz, 1H), 8.08 (d, J = 8.4 Hz, 1H), 7.98-7.94 (m, 1H), 7.76-7.73 (m, 2H), 7.53-7.51 (m, 1H), 5.44-5.37 (m, 1H), 5.26-5.23 (m, 1H), 4.48 (d, J = 5.6 Hz, 2H), 1.55 (d, J = 6.8 Hz, 6H). |
| I-209 | 5-aminopyridin-2-yl | isopropyl | 339.2 | DMSO-d₆: δ 11.18 (s, 1H), 9.57 (s, 1H), 8.89 (s, 1H), 8.04 (d, J = 8.1 Hz, 1H), 7.95-7.90 (m, 1H), 7.71 (d, J = 7.5 Hz, 1H), 7.64 (d, J = 2.7 Hz, 1H), 7.20 (s, 1H), 7.07-7.03 (m, 1H), 5.46-5.37 (m, 1H), 5.06 (s, 2H), 1.55 (d, J = 6.6 Hz, 6H). |
| I-210 | 5-nitropyridin-2-yl | isopropyl | 369.2 | DMSO-d₆: δ 10.55 (s, 1H), 10.22 (s, 1H), 9.12 (d, J = 2.8 Hz, 1H), 8.91 (m, 1H), 8.62-8.59 (m, 1H), 8.07-7.98 (m, 3H), 7.80-7.78 (m, 1H), 5.44-5.37 (m, 1H), 1.52 (d, J = 6.8 Hz, 6H). |
| I-211 | 5-methylpyrimidin-2-yl | isopropyl | 339.2 | DMSO-d₆: δ 12.06 (s, 1H), 10.32 (s, 1H), 8.90 (s, 1H), 8.52 (s, 2H), 8.15 (d, J = 7.6 Hz, 1H), 8.00-7.96 (m, 1H), 7.79 (d, J = 7.2 Hz, 1H), 5.39-5.32 (m, 1H), 2.25 (s, 3H), 1.58 (d, J = 6.8 Hz, 6H). |
| I-212 | pyrimidin-2-yl | isopropyl | 325.2 | DMSO-d₆: δ 12.13 (s, 1H), 8.89 (s, 1H), 8.67 (d, J = 4.8 Hz, 2H), 8.15 (d, J = 8.4 Hz, 1H), 8.01-7.97 (m, 1H), 7.80 (d, J = 7.6 Hz, 1H), 7.20-7.17 (m, 1H), 5.40-5.33 (m, 1H), 1.57 (d, J = 6.8 Hz, 6H). |
| I-213 | 4-(2-hydroxypropan-2-yl)pyridin-2-yl | isopropyl | 382.0 | DMSO-d₆: δ 11.42 (s, 1H), 9.95 (s, 1H), 8.90 (s, 1H), 8.16 (d, J = 5.2 Hz, 1H), 8.10-8.08 (m, 1H), 7.98-7.94 (m, 1H), 7.75-7.74 (m, 1H), 7.63 (s, 1H), 7.12-7.11 (m, 1H), 5.43-5.36 (m, 1H), 5.28 (s, 1H), 1.54 (d, J = 6.8 Hz, 6H), 1.41 (s, 6H). |

TABLE 1-continued

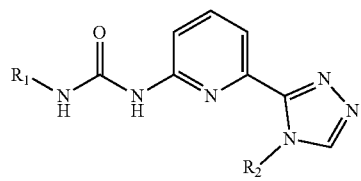

| Compound | R₁ | R₂ | LC-MS (M + H)⁺ | ¹HNMR (ppm) |
|---|---|---|---|---|
| I-214 | 2-(5-(pyridin-2-yl))propan-2-ol group with HO and methyl substituents | isopropyl | 382.2 | DMSO-d₆: δ 11.07 (s, 1H), 9.91 (s, 1H), 8.89 (s, 1H), 8.33 (d, J = 2.0 Hz, 1H), 8.07 (d, J = 8.0 Hz, 1H), 7.97-7.93 (m, 1H), 7.87-7.84 (m, 1H), 7.74 (d, J = 7.2 Hz, 1H), 7.50 (d, J = 8.0 Hz, 1H), 5.44-5.37 (m, 1H), 5.15 (s, 1H), 1.54 (d, J = 6.8 Hz, 6H), 1.44 (s, 6H). |
| I-215 | oxazol-2-yl-methyl | isopropyl | 314.2 | DMSO-d₆: δ 11.2-11.1 (m, 2H), 8.89 (s, 1H), 8.09-8.07 (m, 1H), 8.01-7.97 (m, 1H), 7.80-7.78 (m, 2H), 7.17-7.16 (m, 1H), 5.34 (s, 1H), 1.53 (d, J = 6.4 Hz, 6H). |
| I-216 | benzoxazol-2-yl-methyl | isopropyl | 364.2 | DMSO-d₆: δ 11.78 (s, 1H), 11.38 (s, 1H), 8.92 (s, 1H), 8.15 (d, J = 8.0 Hz, 1H), 8.04-8.00 (m, 1H), 7.84 (d, J = 7.6 Hz, 1H), 7.62 (d, J = 7.6 Hz, 1H), 7.48 (d, J = 7.6 Hz, 1H), 5.55-5.45 (m, 1H), 1.60 (d, J = 6.8 Hz, 6H). |
| I-217 | benzoxazol-2-yl-methyl | 1-hydroxy-2-methylpropyl | 380.2 | DMSO-d₆: δ 11.76 (s, 1H), 11.42 (s, 1H), 8.83 (s, 1H), 8.14 (d, J = 8.0 Hz, 1H), 8.05-8.01 (m, 1H), 7.84 (d, J = 7.2 Hz, 1H), 7.65-7.62 (m, 1H), 7.55-7.52 (m, 1H), 7.37-7.26 (m, 2H), 5.40-5.30 (m, 1H), 5.13-5.04 (m, 1H), 3.90-3.78 (m, 2H), 1.58 (d, J = 6.4 Hz, 3H). |
| I-218 | tert-butyl/isopropyl | isopropyl | 380.1 | DMSO-d₆: δ 11.30 (s, 1H), 9.74 (s, 1H), 8.91 (s, 1H), 8.02-7.94 (m, 3H), 7.82-7.77 (m, 1H), 7.69 (d, J = 8.1 Hz, 1H), 7.44-7.39 (m, 1H), 7.31-7.25 (m, 1H), 5.58-5.35 (m, 1H), 1.50 (d, J = 6.6 Hz, 6H). |

Example 17: Synthesis of Compounds 11-01

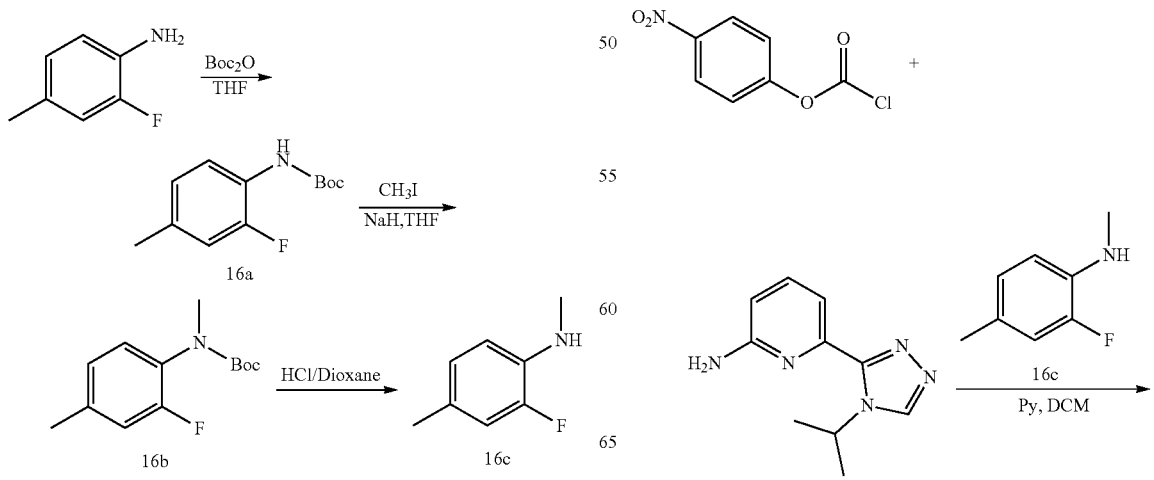

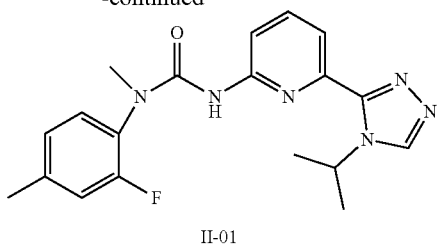

II-01 tert-Butyl 2-fluoro-4-methylphenylcarbamate (Compound 16a)

To a solution of 2-fluoro-4-methylaniline (250 mg, 2.0 mmol) in THF (7 mL) was added di-tert-butyl dicarbonate (117 mg, 0.54 mmol). The resulting solution was stirred overnight at 60° C. The resulting mixture was concentrated under vacuum. The residue was applied onto a silica gel column with ethyl acetate/petroleum ether (15:85). This resulted in 300 mg (67%) of the title compound as a colorless oil. LCMS (ESI, m/z): [M+H]$^+$=226.1.

tert-Butyl 2-fluoro-4-methylphenyl(methyl)carbamate (Compound 16b)

To a solution of Compound 16a (100 mg, 0.44 mmol) in THF (2 mL) was added NaH (20 mg, 0.87 mmol). The mixed was stirred for 30 min at 0° C., then CH$_3$I (189 mg, 1.33 mmol) was added dropwise. The resulting mixture was stirred overnight at room temperature. The reaction was then quenched by the addition of water. The resulting mixture was extracted with ethyl acetate and the organic layers were combined. The resulted mixture was dried over anhydrous sodium sulfate and concentrated under vacuum. The residue was applied onto a silica gel column with ethyl acetate/petroleum ether (17:83). This resulted in 70 mg (66%) of the title compound as a light yellow solid. LCMS (ESI, m/z): [M+H]$^+$=240.1.

2-Fluoro-N,4-dimethylaniline (Compound 16c)

To a solution of Compound 16b (110 mg, 0.46 mmol) in dioxane (2 mL) was added a solution of HCl in dioxane (4 mL, 4M). The mixture solution was stirred for 1 h at room temperature. The resulting mixture was concentrated under vacuum. This resulted in 60 mg (94%) of the title compound as a white solid. LCMS (ESI, m/z): [M+H]$^+$=140.1.

1-(2-Fluoro-4-methylphenyl)-3-(6-(4-isopropyl-4H-1,2,4-triazol-3-yl) pyridin-2-yl)-1-methylurea (Compound III-01)

To a solution of 4-nitrophenyl chloroformate (146 mg, 0.72 mmol) in dichloromethane (4 mL) was added a solution of pyridine (60 mg, 0.72 mmol) and 6-[4-(propan-2-yl)-4H-1,2,4-triazol-3-yl] pyridin-2-amine (144 mg, 0.72 mmol) in DCM (2 mL) was added dropwise. The mixture solution was stirred overnight at room temperature, then pyridine (120 mg, 1.52 mmol) and Compound 16c (76 mg, 0.54 mmol) was added. The resulting solution was stirred for 2 h at room temperature. The reaction mixture was concentrated under vacuum. The residue was applied onto a silica gel column with dichloromethane/methanol (9:1). This resulted in 5 mg (3%) of the title compound as a white solid. LCMS (ESI, m/z): [M+H]$^+$=369.1. $^1$HNMR (300 MHz, DMSO-d$_6$, ppm): δ 8.81 (s, 1H), 8.20 (s, 1H), 7.92-7.88 (m, 1H), 7.83-7.80 (m, 1H), 7.77-7.65 (m, 1H), 7.42-7.38 (m, 1H), 7.22-7.19 (m, 1H), 7.12-7.10 (m, 1H), 5.29-5.23 (m, 1H), 3.33 (d, J=7.5 Hz, 3H), 2.35 (s, 3H), 1.35 (d, J=6.4 Hz, 6H).

Example 18: Synthesis of Compounds III-01

2-Fluoro-1-isocyanato-4-methylbenzene (Compound 17a)

To a solution of 2-fluoro-4-methylaniline (250 mg, 2.0 mmol) in DCM (6 mL) was added saturated NaHCO$_3$ aqueous solution (6 mL). After the mixture cooling to 0° C., triphosgene (238 mg, 7.97 mmol) was added in one portion. The resulting solution was stirred for 1 h at room temperature. The resulting aqueous phase was extracted with DCM several times after separation. The resulted organic phases were combined and washed with brine. The residue was concentrated under vacuum after dried over anhydrous sodium. This resulted in 240 mg (79%) of the title compound as a yellowish oil. LCMS (ESI, m/z): [M+H]⁺=152.0.

3-(2,2-Dimethoxyethyl)-1-(2-fluoro-4-methylphenyl) urea (Compound 17b)

To a solution of Compound 17a (151 mg, 1.0 mmol) in DCM (3 mL) was added TEA (202 mg, 2.00 mmol) and 2,2-dimethoxyethan-1-amine (105 mg, 1.0 mmol). The resulting solution was stirred for overnight at room temperature. The resulting mixture was concentrated under vacuum. The residue was applied onto a silica gel column with ethyl acetate/petroleum ether (32:68). This resulted in 150 mg (62%) of the title compound as a white solid. LCMS (ESI, m/z): [M+H]⁺=257.1.

1-(2-Fluoro-4-methylphenyl)-2,3-dihydro-1H-imidazol-2-one (Compound 17c)

To a solution of Compound 17b (150 mg, 0.59 mmol) in CH₃COOH (3 mL) was added 4-methylbenzene-1-sulfonic acid (101 mg, 0.59 mmol). The mixture solution was stirred for 2 h at 80° C. The resulting mixture was concentrated under vacuum. The residue was applied onto a silica gel column with dichloromethane/methanol (88:12). This resulted in 70 mg (62%) of the title compound as a white solid. LCMS (ESI, m/z): [M+H]⁺=193.1.

3-(2-Fluoro-4-methylphenyl)-1-(6-(4-isopropyl-4H-1,2,4-triazol-3-yl)pyridin-2-yl)-1H-imidazol-2(3H)-one (Compound III-01)

To a solution of Compound 17c (80 mg, 0.33 mmol) and 2-bromo-6-[4-(propan-2-yl)-4H-1,2,4-triazol-3-yl]pyridine (88 mg, 0.33 mmol) in dioxane (2 mL) was added Pd₂(dba)₃·CHCl₃ (34 mg, 0.03 mmol), Xantphos (35 mg, 0.06 mmol) and Cs₂CO₃ (215 mg, 0.66 mmol). The mixture solution was stirred for 2 h at 80° C. under N₂ atmosphere. The mixture was diluted with ethyl acetate. The resulted mixture was washed with water and brine. The resulting mixture was dried over anhydrous sodium sulfate and concentrated under vacuum. The residue was applied onto a silica gel column with MeOH/DCM (7:93). The resulted crude was purified by a C₁₈ column with ACN/H₂O (42:58). This resulted in 6.0 mg (4%) of the title compound as a white solid. LCMS (ESI, m/z): [M+H]⁺=379.3. ¹HNMR (300 MHz, DMSO-d₆, ppm): δ 8.93 (s, 1H), 8.42-8.39 (m, 1H), 8.15-8.13 (m, 1H), 8.00-7.98 (m, 1H), 7.51-7.06 (m, 5H), 5.43-5.34 (m, 1H), 2.37 (s, 3H), 1.54-1.45 (m, 6H).

Example 19: Synthesis of Compounds III-02

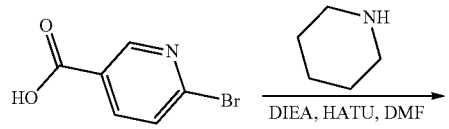

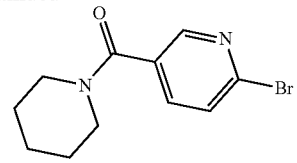

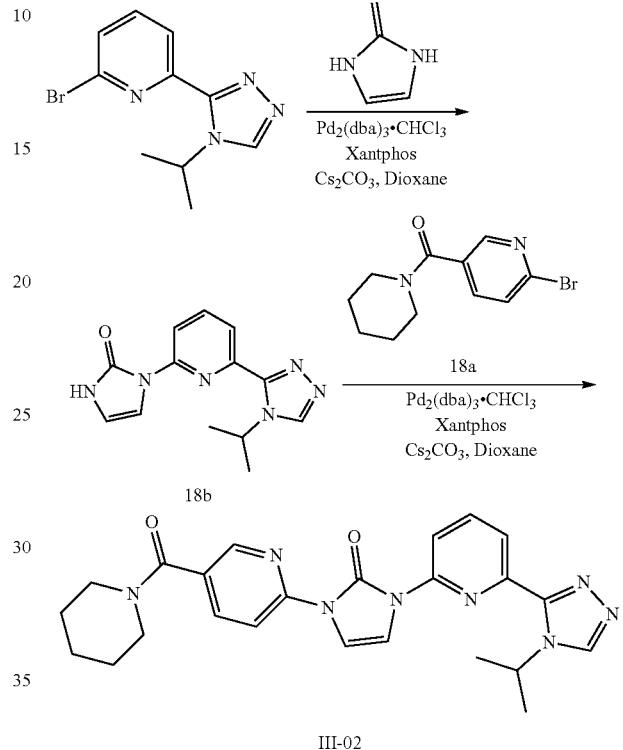

(6-Bromopyridin-3-yl)(piperidin-1-yl)methanone (Compound 18a)

To a solution of 6-bromonicotinic acid (1.0 g, 4.95 mmol) in DMF (6 mL) was added piperidine (422 mg, 4.95 mmol), DIEA (1.9 g, 14.9 mmol) and HATU (2.2 g, 5.94 mmol). The resulting mixture was stirred at room temperature for 2 h. After the reaction was completed, the mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with DCM/CH₃OH (20/1, v/v) to afford the title compound (800 mg, 60%) as a brown solid. LCMS (ESI, m/z): [M+H]⁺=269.2.

1-(6-(4-Isopropyl-4H-1,2,4-triazol-3-yl)pyridin-2-yl)-1H-imidazol-2(3H)-one (Compound 18b)

To a solution of 2-bromo-6-(4-isopropyl-4H-1,2,4-triazol-3-yl)pyridine (200 mg, 0.75 mmol) in DMF (5 mL) was added 2,3-dihydro-H-imidazol-2-one (94.4 mg, 1.12 mmol), Pd₂(dba)₃·CHCl₃ (77.5 mg, 0.08 mmol), Xantphos (86.6 mg, 0.15 mmol) and Cs₂CO₃ (731.8 mg, 2.25 mmol). The resulting mixture was stirred at 60° C. for 5 h under N₂ atmosphere. The resulting mixture was diluted with H₂O and extracted with ethyl acetate. The combined organic layer

1-(6-(4-Isopropyl-4H-1,2,4-triazol-3-yl)pyridin-2-yl)-3-(5-(piperidine-1-carbonyl)pyridin-2-yl)-1H-imidazol-2(3H)-one (Compound III-02)

To a solution of Compound 18b (80.3 mg, 0.30 mmol) in DMF (3 mL) was added Compound 18a (80.0 mg, 0.30 mmol), Pd$_2$(dba)$_3$·CHCl$_3$ (30.8 mg, 0.03 mmol), Xantphos (34.4 mg, 0.06 mmol) and Cs$_2$CO$_3$ (291 mg, 0.89 mmol). The resulting mixture was stirred at 100° C. for 2 h under N$_2$ atmosphere. The resulting mixture was diluted with H$_2$O and then filtered. The solid was collected and purified by flash column chromatography with dichloromethane/methanol (10/1, v/v) to afford the title compound (19.9 mg, 15%) as a white solid. LCMS (ESI, m/z): [M+H]$^+$=459.2. $^1$H NMR (400 MHz, DMSO-d$_6$, ppm): δ 8.95 (s, 1H), 8.53 (d, J=2.0 Hz, 1H), 8.45-8.42 (m, 2H), 8.21-8.17 (m, 1H), 8.05-8.02 (m, 2H), 7.66 (d, J=3.6 Hz, 1H), 7.48 (d, J=3.2 Hz, 1H), 5.41-5.37 (m, 1H), 3.65-3.55 (m, 2H), 3.50-3.33 (m, 2H), 1.64-1.54 (m, 12H).

Example 20: Synthesis of Compounds III-03

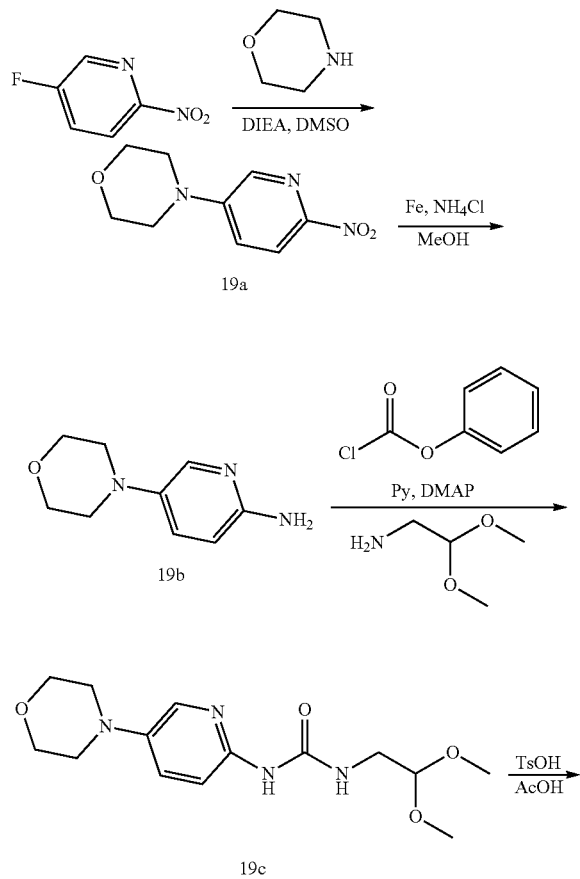

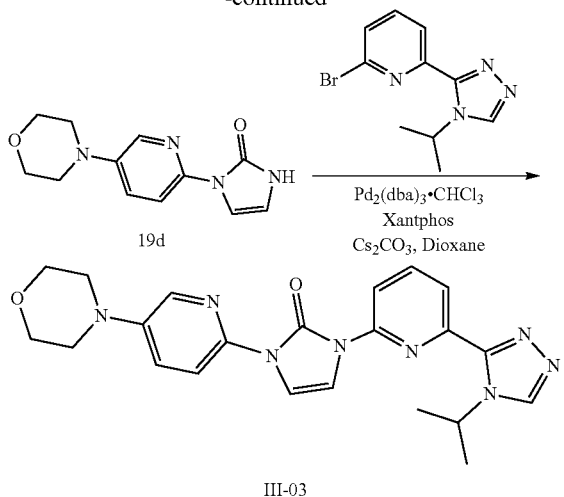

4-(6-Nitropyridin-3-yl)morpholine (Compound 19a)

To a solution of 5-fluoro-2-nitropyridine (2.0 g, 14.1 mmol) in DMSO (20 mL) was added morpholine (1.5 g, 16.9 mmol) and DIEA (5.5 g, 42.2 mmol). The reaction mixture was stirred at 70° C. for 2 h under N$_2$ atmosphere. The mixture was diluted with EtOAc. The resulting organic layer was washed with brine, dried over anhydrous sodium sulfate and filtered. The filtrate was concentrated under vacuum. The residue was purified by flash column chromatography with dichloromethane/methanol (10/1) to afford the title compound (2.5 g, 82%) as a yellow solid. LCMS (ESI, m/z): [M+H]$^+$=209.1.

5-Morpholinopyridin-2-amine (Compound 19b)

To a mixture of Compound 19a (3.0 g, 14.0 mmol) and Fe (3.2 g, 57.0 mmol) in methanol (30 mL) was added NH$_4$Cl solution (12 mL, 220 mmol). The reaction mixture was stirred at 85° C. for 16 h. The resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with dichloromethane/methanol (5/1, v/v) to afford the title compound (2.5 g, 94%) as a brown solid. LCMS (ESI, m/z): [M+H]$^+$=179.1.

1-(2,2-Dimethoxyethyl)-3-(5-morpholinopyridin-2-yl) urea (Compound 19c)

To a solution of Compound 19b (2.0 g, 11.2 mmol) in pyridine (20 mL) was added DMAP (67.8 mg, 0.55 mmol). Then a solution of phenyl carbonochloridate (2.1 g, 13.3 mmol) was added dropwise to the mixture at −20° C. The reaction mixture was stirred at room temperature for 16 h. Then 2,2-dimethoxyethan-1-amine (1.2 g, 11.2 mmol) was added dropwise to the mixture at −20° C. The resulting mixture was stirred at 55° C. for 16 h. The reaction mixture was concentrated under vacuum. The residue was purified by flash column chromatography with dichloromethane/methanol (5/1, v/v) to afford the title compound (800 mg, 16%) as a red solid. LCMS (ESI, m/z): [M+H]$^+$=310.2.

3-(5-Morpholinopyridin-2-yl)-1H-imidazol-2(3H)-one (Compound 19d)

To a solution of Compound 19c (800 mg, 2.58 mmol) in CH₃COOH (15 mL) was added 4-methylbenzene-1-sulfonic acid (487 mg, 2.83 mmol). The reaction mixture was stirred at 80° C. for 2 h. The reaction mixture was concentrated under vacuum. The residue was diluted with H₂O and extracted with ethyl acetate. The combined organic layer was washed with brine, dried over anhydrous sodium sulfate and filtered. The filtrate was concentrated under vacuum. The residue was purified by flash column chromatography with dichloromethane/methanol (10/1, v/v) to afford the title compound (400 mg, 58%) as an off-white solid. LCMS (ESI, m/z): [M+H]⁺=246.1.

1-(6-(4-Isopropyl-4H-1, 2, 4-triazol-3-yl) pyridin-2-yl)-3-(5-morpholinopyridin-2-yl)-1H-imidazol-2(3H)-one (Compound III-03)

To a mixture of Compound 19d (300 mg, 1.22 mmol) and 2-bromo-6-[4-(propan-2-yl)-4H-1,2,4-triazol-3-yl]pyridine (323 mg, 1.21 mmol) in DMF (4 mL) was added Pd₂(dba)₃.CHCl₃ (55.6 mg, 0.05 mmol), XantPhos (70.2 mg, 0.12 mmol) and Cs₂CO₃ (1.18 g, 3.63 mmol). The reaction mixture was stirred at 100° C. for 16 h under N₂ atmosphere. The resulting mixture was diluted with H₂O and extracted with ethyl acetate. The combined organic layer was washed with brine, dried over anhydrous sodium sulfate and filtered. The filtrate was concentrated under vacuum. The residue was purified by Prep-HPLC with the following conditions: Column: XBridge Prep OBD C18 Column 30×150 mm, 5 um; Mobile Phase A: Water (10 mmol/L NH₄HCO₃), Mobile Phase B: ACN; Flow rate: 60 mL/min; Gradient: 23% B to 40% B in 7 min; 254/220 nm; Rt: 6.75 min to afford the title compound (36.7 mg, 7%) as a yellow solid. LCMS (ESI, m/z): [M+H]⁺=433.2. ¹H NMR (300 MHz, DMSO-d₆, ppm): δ 8.95 (s, 1H), 8.47 (d, J=7.8 Hz, 1H), 8.19-8.13 (m, 3H), 8.03 (d, J=7.2 Hz, 1H), 7.62-7.58 (m, 1H), 7.53 (d, J=3.3 Hz, 1H), 7.42 (d, J=3.3 Hz, 1H), 5.44-5.35 (m, 1H), 3.79-3.76 (m, 4H), 3.21-3.18 (m, 4H), 1.56 (d, J=6.6 Hz, 6H).

Example 21: Synthesis of Compounds III-04

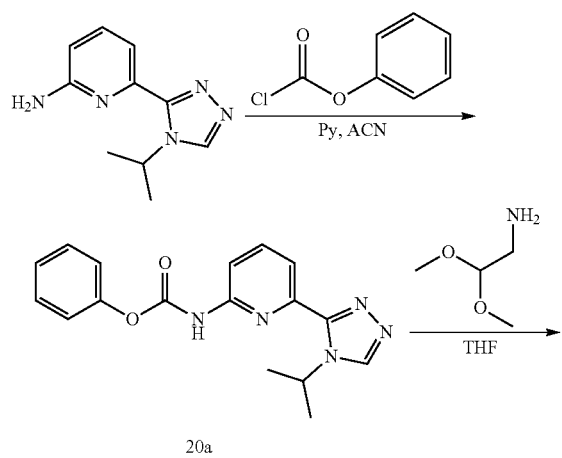

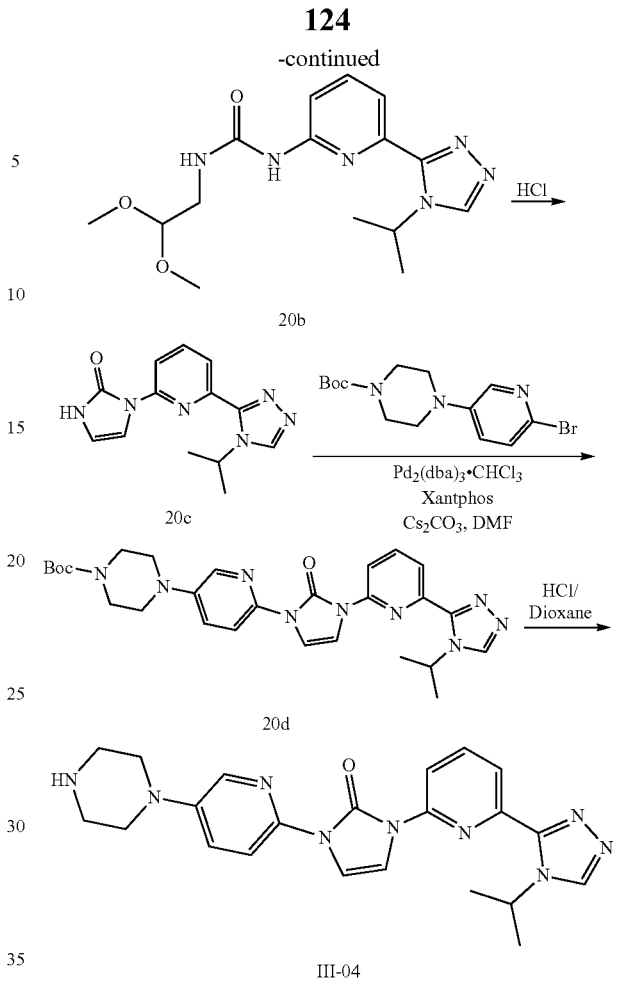

Phenyl 6-(4-isopropyl-4H-1,2,4-triazol-3-yl)pyridin-2-ylcarbamate (Compound 20a)

To a stirred solution of 6-[4-(propan-2-yl)-4H-1,2,4-triazol-3-yl]pyridin-2-amine (500 mg, 2.46 mmol) in CH₃CN (10 mL) was added phenyl carbonochloridate (462 mg, 2.95 mmol) and pyridine (292 mg, 3.69 mmol). The resulting mixture was stirred at room temperature for 3 h under N₂. The resulting mixture was diluted with water and extracted with EtOAc. The combined organic layer was washed with brine, dried over anhydrous Na₂SO₄ and filtered. The filtrate was concentrated in vacuo to afford the title compound (700 mg, crude) as a yellow oil. LCMS (ESI, m/z): [M+H]⁺=324.2.

3-(2,2-Dimethoxyethyl)-1-[6-[4-(propan-2-yl)-4H-1,2,4-triazol-3-yl]pyridin-2-yl]urea (Compound 20b)

To a stirred solution of Compound 20a (1.3 g, 4.02 mmol) in THF (20 mL) were added 2,2-dimethoxyethan-1-amine (4.2 g, 40.2 mmol) under N₂. The resulting mixture was stirred at 60° C. for 3 h. The resulting mixture was concentrated under vacuum. The residue was purified by flash column chromatography with CH₂Cl₂/MeOH (10/1, v/v) to afford the title compound (800 mg, 60%) as a yellow solid. LCMS (ESI, m/z): [M+H]⁺=335.1

1-[6-[4-(Propan-2-yl)-4H-1,2,4-triazol-3-yl]pyridin-2-yl]-2,3-dihydro-1H-imidazol-2-one (Compound 20c)

A solution of Compound 20b (500 mg, 0.15 mmol) in HCl (2 mL, 2.5 M) was stirred at room temperature for 3 h. The mixture was acidified to pH 8 with saturated NaHCO$_3$ (aq.). The resulting mixture was extracted with EtOAc. The combined organic layer was washed with brine, dried over anhydrous Na$_2$SO$_4$ and filtered. The filtrate was concentrated under vacuum. The residue was purified by reverse phase flash column chromatography with 0-100% CH$_3$CN in H$_2$O to afford the title compound (220 mg, 49%) as a yellow solid. LCMS (ESI, m/z): [M+H]$^+$=271.2.

tert-Butyl 4-(6-(1-(6-(4-isopropyl-4H-1,2,4-triazol-3-yl)pyridin-2-yl)-2-oxo-1,2-dihydroimidazol-3-yl)pyridin-3-yl)piperazine-1-carboxylate (Compound 20d)

To a solution of Compound 20c (100 mg, 0.37 mmol) in DMF (5 mL) was added tert-butyl 4-(6-bromopyridin-3-yl)piperazine-1-carboxylate (190 mg, 0.56 mmol), Pd$_2$(dba)$_3$-CHCl$_3$ (38.3 mg, 0.03 mmol), Xantphos (42.8 mg, 0.07 mmol) and Cs$_2$CO$_3$ (362 mg, 1.11 mmol). The resulting mixture was stirred at 100° C. for 3 h under N$_2$ atmosphere. The resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with dichloromethane/methanol (10/1, v/v) to afford the title compound (120 mg, 61%) as a yellow solid. LCMS (ESI, m/z): [M+H]$^+$=532.2.

1-(6-(4-Isopropyl-4H-1,2,4-triazol-3-yl)pyridin-2-yl)-3-(5-(piperazin-1-yl)pyridin-2-yl)-1H-imidazol-2(3H)-one (Compound III-04)

A solution of Compound 20d (250 mg, 0.18 mmol) in HCl/Dioxane (10 mL, 4 mol/L) was stirred at room temperature for 3 h. After the reaction was completed, the mixture was evaporated in vacuo. The residue was purified by Prep-HPLC with the following conditions: Column: XBridge Shield RP18 OBD Column 30×150 mm, 5 um; Mobile Phase A: Water (10 mmol/L NH$_4$HCO$_3$), Mobile Phase B: ACN; Flow rate: 60 mL/min; Gradient: 14% B to 30% B in 10 min; 254/220 nm; Rt: 10.25 min to afford the title compound (9.7 mg, 10%) as a white solid. LCMS (ESI, m/z): [M+H]=432.2. $^1$HNMR (300 MHz, DMSO-d$_6$, ppm): δ 8.95 (s, 1H), 8.47-8.44 (m, 1H), 8.19-8.10 (m, 3H), 8.02-7.99 (m, 1H), 7.58-7.50 (m, 2H), 7.40 (d, J=3.3 Hz, 1H), 5.41-5.36 (m, 1H), 3.13-3.10 (m, 4H), 2.87-2.83 (m, 4H), 1.54 (d, J=6.6 Hz, 6H).

Example 22: Synthesis of Compounds III-05 to III-10

Following the procedure described above and substituting the appropriate reagents, starting materials and purification methods known to those skilled in the art, the following compounds of the present invention were prepared.

TABLE 2

| Compound | R$_1$ | R$_2$ | LC-MS (M + H)$^+$ | $^1$HNMR (ppm) |
|---|---|---|---|---|
| III-05 | 5-methylpyridin-2-yl | isopropyl | 362.0 | DMSO-d$_6$: δ 8.95 (s, 1H), 8.46 (d, J = 8.4 Hz, 1H), 8.34 (s, 1H), 8.26-8.16 (m, 2H), 8.04 (d, J = 7.2 Hz, 1H), 7.84 (d, J = 8.0 Hz, 1H), 7.61 (s, 1H), 7.45 (s, 1H), 5.41-5.38 (m, 1H), 2.34 (s, 3H), 1.56 (d, J = 6.4 Hz, 6H). |
| III-06 | 5-phenylpyridin-2-yl | isopropyl | 424.2 | DMSO-d$_6$: δ 8.96 (s, 1H), 8.84 (s, 1H), 8.51-8.45 (m, 2H), 8.35-8.31 (m, 1H), 8.20-8.15 (m, 1H), 8.06-8.00 (m, 1H), 7.82-7.75 (m, 2H), 7.69 (s, 1H), 7.55-7.44 (m, 4H), 5.42-5.39 (m, 1H), 1.57 (d, J = 6.8 Hz, 6H). |
| III-07 | 5-phenylpyridin-2-yl | 1-hydroxy-2-methylpropan-2-yl | 440.2 | DMSO-d$_6$: δ 8.87-8.83 (m, 2H), 8.48-8.45 (m, 2H), 8.34-8.32 (m, 1H), 8.21-8.17 (m, 1H), 8.03 (d, J = 8.0 Hz, 1H), 7.80-7.78 (m, 2H), 7.67 (d, J = 3.2 Hz, 1H), 7.55-7.51 (m, 3H), 7.46-7.42 (m, 1H), 5.37-5.33 (m, 1H), 5.13-5.10 (m, 1H), 3.78-3.69 (m, 2H), 1.52 (d, J = 7.2 Hz, 3H). |

TABLE 2-continued

[Structure: R1-N-C(=O)-N(imidazole)-pyridine-triazole-R2]

| Compound | R₁ | R₂ | LC-MS (M + H)⁺ | ¹HNMR (ppm) |
|---|---|---|---|---|
| III-08 | 4-phenyl-pyridin-2-yl (with gem-dimethyl linker) | -C(CH₃)₂-CH₂OH (isobutanol-like) | 440.2 | DMSO-d₆: δ 8.86 (s, 1H), 8.68 (d, J = 0.8 Hz, 1H), 8.57 (d, J = 5.2 Hz, 1H), 8.47 (d, J = 0.8 Hz, 1H), 8.18-8.15 (m, 1H), 8.04 (d, J = 0.8 Hz, 1H), 7.83 (d, J = 6.8 Hz, 2H), 7.68-7.67 (m, 2H), 7.60-7.53 (m, 4H), 5.31-5.28 (m, 1H), 5.10-5.03 (m, 1H), 3.79-3.65 (m, 2H), 1.52 (d, J = 6.8 Hz, 3H). |
| III-09 | 4-morpholino-pyridin-2-yl (with gem-dimethyl linker) | isopropyl | 433.2 | DMSO-d₆: δ 8.95 (s, 1H), 8.46 (d, J = 8.0 Hz, 1H), 8.17-8.11 (m, 2H), 8.02 (d, J = 7.6 Hz, 1H), 7.86 (d, J = 2.4 Hz, 1H), 7.59 (d, J = 3.2 Hz, 1H), 7.41 (d, J = 3.6 Hz, 1H), 6.84-6.82 (m, 1H), 5.42-5.35 (m, 1H), 3.77-3.74 (m, 4H), 3.35-3.30 (m, 4H), 1.54 (d, J = 6.8 Hz, 6H). |
| III-10 | 5-morpholino-pyridin-2-yl (with gem-dimethyl linker) | -C(CH₃)₂-CH₂OH | 449.3 | DMSO-d₆: δ 8.87 (s, 1H), 8.46-8.44 (m, 1H), 8.22-8.13 (m, 3H), 8.01-7.99 (m, 1H), 7.62-7.59 (m, 1H), 7.51 (d, J = 3.6 Hz, 1H), 7.45 (d, J = 3.6 Hz, 1H), 5.40-5.30 (m, 1H), 5.13-5.10 (m, 1H), 3.78-3.67 (m, 6H), 3.21-3.18 (m, 4H), 1.51 (d, J = 7.2 Hz, 3H). |

Example 23: Synthesis of Compounds IV-01

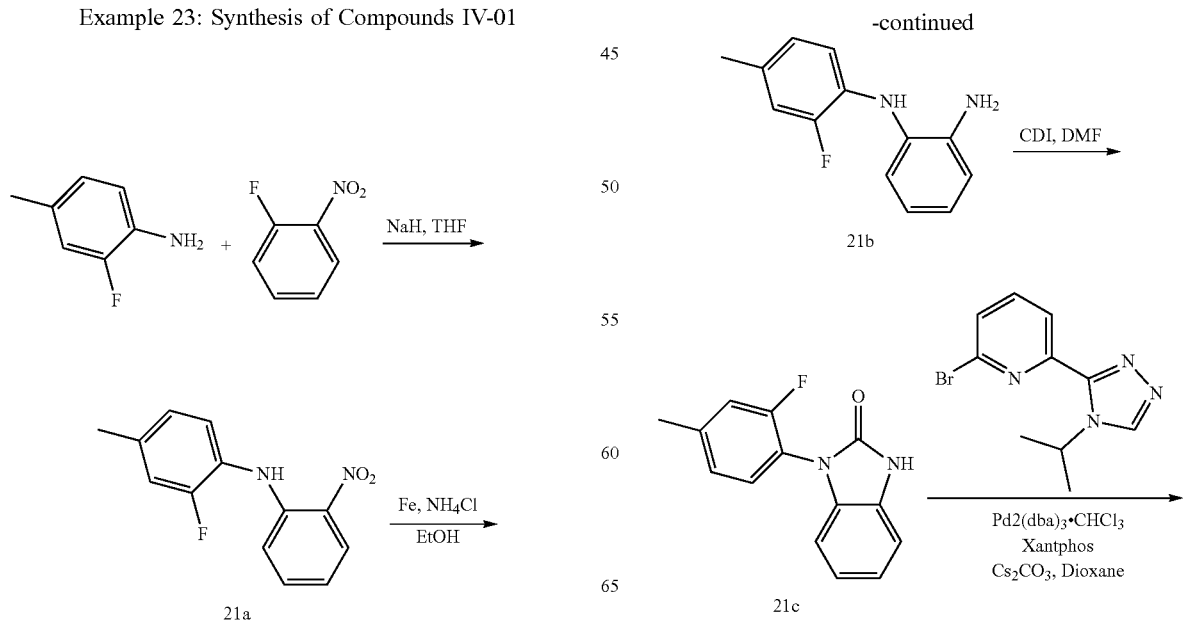

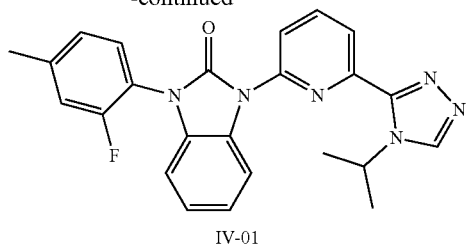

IV-01

2-Fluoro-4-methyl-N-(2-nitrophenyl) benzenamine (Compound 21a)

To a solution of 2-fluoro-4-methylaniline (125 mg, 1.0 mmol) in THF (3 mL) was added sodium hydride (96 mg, 4.0 mmol) batchwise at 0° C. The mixture was stirred for 30 min at this temperature then 1-fluoro-2-nitrobenzene (141 mg, 1.0 mmol) was added. The resulting mixture was stirred for 3 h at room temperature. The reaction was then quenched by the addition of 3 mL of saturated $NH_4Cl$ aqueous solution. The resulting solution was extracted with ethyl acetate several times. The resulted organic layers were combined and washed with brine. The mixture was dried over anhydrous magnesium sulfate and concentrated under vacuum. The residue was applied onto a silica gel column with ethyl acetate/petroleum ether (25:75). This resulted in 200 mg (81%) of the title compound as a yellow solid. LCMS (ESI, m/z): [M+H]$^+$=247.1.

N1-(2-Fluoro-4-methylphenyl) benzene-1,2-diamine (Compound 21b)

To a solution of Compound 21a (350 mg, 1.42 mmol) in ethanol (5 mL) was added saturated $NH_4Cl$ aqueous solution (1 mL), iron powder (907 mg, 16.2 mmol). The mixture was stirred for 2 h at 80° C. The solids were filtered out. The resulting mixture was concentrated under vacuum. The resulted solid was washed with water and further dried under vacuum. This resulted in 300 mg (98%) of the title compound as a yellow solid. LCMS (ESI, m/z): [M+H]$^+$=217.1.

1-(2-Fluoro-4-methylphenyl)-1H-benzo[d]imidazol-2(3H)-one (Compound 21c)

To a solution of Compound 21b (100 mg, 0.46 mmol) in DMF (2 mL) was added CDI (91 mg, 0.64 mmol). The resulting solution was stirred overnight at 60° C. The resulting solution was diluted with ethyl acetate. The resulting mixture was washed with water and brine. The mixture was dried over anhydrous sodium sulfate and concentrated under vacuum. The residue was applied onto a silica gel column with dichloromethane/methanol (91:9). This resulted in 80 mg (71%) of the title compound as a yellow solid. LCMS (ESI, m/z): [M+H]$^+$=243.0.

1-(2-Fluoro-4-methylphenyl)-3-(6-(4-isopropyl-4H-1,2,4-triazol-3-yl) pyridin-2-yl)-1H-benzo[d]imidazol-2(3H)-one (Compound IV-01)

To a solution of Compound 21c (60 mg, 0.25 mmol) in dioxane (2 mL) was added 2-bromo-6-[4-(propan-2-yl)-4H-1,2,4-triazol-3-yl]pyridine (54 mg, 0.20 mmol) and $Pd_2(dba)_3 \cdot CHCl_3$ (24 mg, 0.025 mmol), Xantphos (27 mg, 0.05 mmol) and $Cs_2CO_3$ (225 mg, 0.69 mmol). The mixed was stirred for 2 h at 100° C. The reaction was diluted with ethyl acetate. The resulting mixture was washed with brine and dried over anhydrous sodium sulfate. The residue was applied onto a silica gel column with dichloromethane/methanol (92:8). This resulted in 17.7 mg (17%) of the title compound as a white solid. LCMS (ESI, m/z): [M+H]$^+$=429.2. $^1$HNMR (300 MHz, DMSO-d$_6$, ppm): δ 8.99 (s, 1H), 8.28-8.23 (m, 1H), 8.15-8.08 (m, 2H), 7.85-7.81 (m, 1H), 7.65-7.60 (m, 1H), 7.42-7.38 (m, 1H), 7.29-7.20 (m, 1H), 7.19-7.16 (m, 2H), 6.90-6.89 (m, 1H), 5.54-5.45 (m, 1H), 2.45 (s, 3H), 1.45 (d, J=6.6 Hz, 6H).

Example 24: Synthesis of Compounds V-01

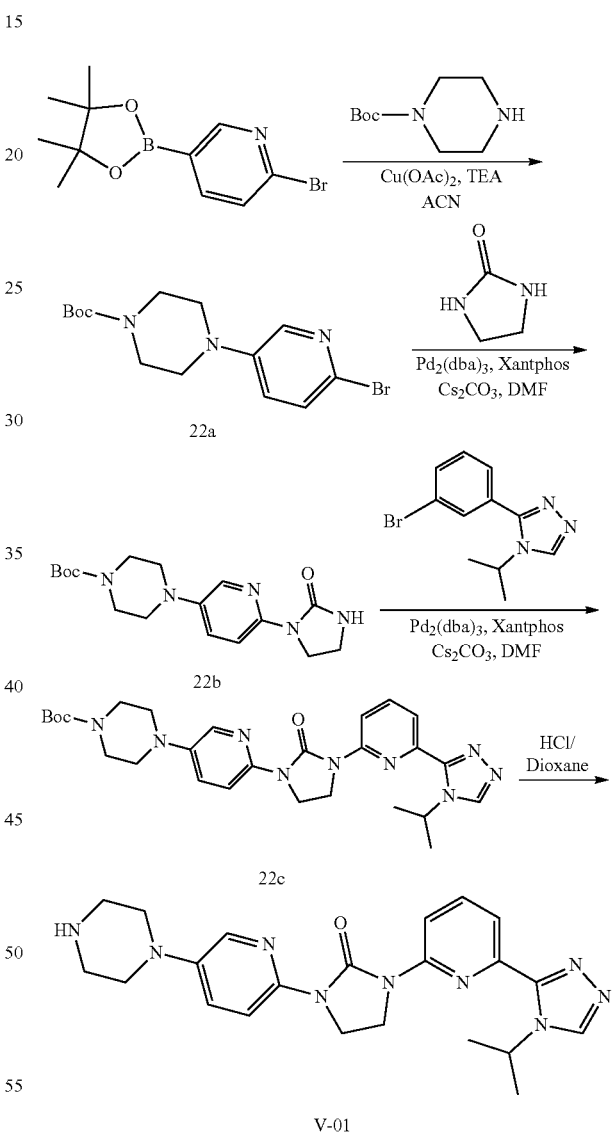

V-01 tert-Butyl 4-(6-bromopyridin-3-yl)piperazine-1-carboxylate (Compound 22a)

To a solution of 2-bromo-5-(4,4,5,5-tetramethyl-1,3,2-dioxaborolan-2-yl)pyridine (3.0 g, 10.6 mmol) in CH$_3$CN (50 mL) was added Cu(OAc)$_2$ (1.9 g, 10.6 mmol), tert-butyl piperazine-1-carboxylate (3.9 g, 21.2 mmol), Et$_3$N (2.1 g, 21.1 mmol) and 4A MS (5.0 g). The reaction mixture was stirred at 80° C. for 16 h under N₂ atmosphere. After the reaction was completed, the reaction mixture was cooled to room temperature and then filtered. The filtrate was diluted with H₂O and extracted with ethyl acetate. The combined organic layer was washed with brine, dried over anhydrous sodium sulfate and filtered. The filtrate was concentrated under vacuum. The residue was purified by flash column chromatography with petroleum ether/EtOAc (5/1, v/v) to afford the title compound (500 mg, 11%) as a white solid. LCMS (ESI, m/z): [M+H]⁺=342.1.

tert-Butyl 4-(6-(2-oxoimidazolidin-1-yl)pyridin-3-yl)piperazine-1-carboxylate (Compound 22b)

To a solution of Compound 22a (300 mg, 0.87 mmol) in DMF (15 mL) was added imidazolidin-2-one (757 mg, 8.78 mmol), Cs₂CO₃ (858 mg, 2.63 mmol), Pd₂(dba)₃ (45.5 mg, 0.04 mmol) and XantPhos (50.8 mg, 0.09 mmol). The reaction mixture was stirred at 100° C. for 1 h under N₂ atmosphere. The resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with dichloromethane/methanol (10/1, v/v) to afford the title compound (200 mg, 52%) as a yellow solid. LCMS (ESI, m/z): [M+H]⁺=348.2.

tert-Butyl 4-(6-(3-(6-(4-isopropyl-4H-1,2,4-triazol-3-yl)pyridin-2-yl)-2-oxoimidazolidin-1-yl)pyridin-3-yl)piperazine-1-carboxylate (Compound 22c)

To a solution of Compound 22b (200 mg, 0.57 mmol) in DMF (5 mL) was added 2-bromo-6-[4-(propan-2-yl)-4H-1,2,4-triazol-3-yl]pyridine (195 mg, 0.73 mmol), Cs₂CO₃ (562 mg, 1.72 mmol), Pd₂(dba)₃ (29.8 mg, 0.03 mmol) and XantPhos (33.3 mg, 0.06 mmol). The reaction mixture was stirred at 100° C. for 1 h under N₂ atmosphere. The resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with dichloromethane/methanol (10/1, v/v) to afford the title compound (100 mg, 26%) as a yellow solid. LCMS (ESI, m/z): [M+H]⁺=534.3.

1-(6-(4-Isopropyl-4H-1,2,4-triazol-3-yl)pyridin-2-yl)-3-(5-(piperazin-1-yl)pyridin-2-yl)imidazolidin-2-one (Compound V-01)

A solution of Compound 22c (100 mg, 0.19 mmol) in HCl/dioxane (5 mL, 4 mol/L) was stirred at room temperature for 2 h. After the reaction was completed, the reaction mixture was concentrated under vacuum. The residue was purified by Prep-HPLC with the following conditions: Column: Xcelect CSH F-pheny OBD Column 19×250 mm, 5 um; Mobile Phase A: Water (10 mmol/L NH₄HCO₃), Mobile Phase B: ACN; Flow rate: 60 mL/min; Gradient: 13% B to 42% B in 7 min; 254/220 nm; Rt: 6.72 min to afford the title compound (15.9 mg, 19%) as a white solid. LCMS (ESI, m/z): [M+H]⁺=434.2. ¹H NMR (400 MHz, DMSO-d₆, ppm): δ 8.90 (s, 1H), 8.35-8.33 (m, 1H), 8.08-8.03 (m, 2H), 7.99-7.95 (m, 1H), 7.81-7.79 (m, 1H), 7.49 (d, J=2.8 Hz, 1H), 5.55-5.45 (m, 1H), 4.13-4.08 (m, 4H), 3.05-3.03 (m, 4H), 2.85-2.83 (m, 4H), 1.52 (d, J=6.8 Hz, 6H).

Example 25: Synthesis of Compounds V-02 to V-27

Following the procedure described above and substituting the appropriate reagents, starting materials and purification methods known to those skilled in the art, the following compounds of the present invention were prepared.

TABLE 3

| Compound | R₁ | R₂ | LC-MS (M + H)⁺ | ¹HNMR (ppm) |
|---|---|---|---|---|
| V-02 | 5-fluoropyridin-2-yl | isopropyl | 368.1 | DMSO-d₆: δ 8.92 (s, 1H), 8.41 (d, J = 3.2 Hz, 1H), 8.36-8.29 (m, 2H), 8.03-7.99 (m, 1H), 7.86-7.78 (m, 2H), 5.54-5.47 (m, 1H), 4.19-4.10 (m, 4H), 1.54 (d, J = 6.8 Hz, 6H). |
| V-03 | 5-fluoropyridin-2-yl | 1-hydroxypropan-2-yl | 384.2 | DMSO-d₆: δ 8.74 (s, 1H), 8.33 (d, J = 2.4 Hz, 1H), 8.27-8.21 (m, 2H), 7.94-7.90 (m, 1H), 7.76-7.72 (m, 2H), 5.39-5.35 (m, 1H), 5.05-4.95 (m, 1H), 4.06 (s, 4H), 3.68-3.63 (m, 2H), 1.42 (d, J = 6.8 Hz, 3H). |

TABLE 3-continued

| Compound | R₁ | R₂ | LC-MS (M + H)⁺ | ¹HNMR (ppm) |
|---|---|---|---|---|
| V-04 | isoquinolin-3-yl | (S)-1-hydroxypropan-2-yl | 416.2 | DMSO-d₆: δ 9.23 (s, 1H), 8.82 (s, 1H), 8.60 (s, 1H), 8.40 (d, J = 8.0 Hz, 1H), 8.07 (d, J = 8.0 Hz, 1H), 8.02-7.94 (m, 2H), 7.83 (d, J = 7.2 Hz, 1H), 7.75-7.71 (m, 1H), 7.56-7.52 (m, 1H), 5.49-5.45 (m, 1H), 5.09-5.07 (m, 1H), 4.30-4.26 (m, 2H), 4.20-4.15 (m, 2H), 3.78-3.68 (m, 2H), 1.51 (d, J = 7.2 Hz, 3H). |
| V-05 | 5-phenylpyridin-2-yl | isopropyl | 426.2 | DMSO-d₆: δ 8.92 (s, 1H), 8.73 (d, J = 2.1 Hz, 1H), 8.40-8.35 (m, 2H), 8.19-8.15 (m, 1H), 8.04-7.99 (m, 1H), 7.85 (d, J = 7.2 Hz, 1H), 7.75-7.73 (m, 2H), 7.53-7.48 (m, 2H), 7.42-7.37 (m, 1H), 5.53-5.48 (m, 1H), 4.19 (s, 4H), 1.53 (d, J = 6.6 Hz, 6H). |
| V-06 | 5-(4-fluorophenyl)pyridin-2-yl | isopropyl | 444.2 | DMSO-d₆: δ 8.91 (s, 1H), 8.71 (d, J = 2.0 Hz, 1H), 8.40-8.31 (m, 2H), 8.19-8.10 (m, 1H), 8.05-7.96 (m, 1H), 7.87-7.74 (m, 3H), 7.41-7.27 (m, 2H), 5.57-5.45 (m, 1H), 4.18 (s, 4H), 1.53 (d, J = 6.8 Hz, 6H). |
| V-07 | [3,4'-bipyridin]-6-yl | isopropyl | 427.2 | DMSO-d₆: δ 8.92-8.90 (m, 2H), 8.67-8.65 (m, 2H), 8.43-8.30 (m, 3H), 8.04-7.99 (m, 1H), 7.86-7.79 (m, 3H), 5.52-5.48 (m, 1H), 4.19 (s, 4H), 1.53 (d, J = 6.6 Hz, 6H). |
| V-08 | 5-phenylpyridin-2-yl | (S)-1-hydroxypropan-2-yl | 442.1 | DMSO-d₆: δ 8.82 (s, 1H), 8.74 (d, J = 2.1 Hz, 1H), 8.39-8.35 (m, 2H), 8.20-8.16 (m, 1H), 8.05-7.98 (m, 1H), 7.84 (d, J = 7.2 Hz, 1H), 7.75-7.73 (m, 2H), 7.53-7.48 (m, 2H), 7.42-7.38 (m, 1H), 5.47-5.44 (m, 1H), 5.09-5.06 (m, 1H), 4.18 (s, 4H), 3.78-3.67 (m, 2H), 1.51 (d, J = 6.9 Hz, 3H). |
| V-09 | 4-phenylpyridin-2-yl | (S)-1-hydroxypropan-2-yl | 442.1 | DMSO-d₆: δ 8.82 (s, 1H), 8.59 (s, 1H), 8.46 (d, J = 5.2 Hz, 1H), 8.38 (d, J = 8.4 Hz, 1H), 7.99-7.97 (m, 1H), 7.83 (d, J = 7.6 Hz, 1H), 7.78-7.76 (m, 2H), 7.59-7.49 (m, 3H), 7.45 (d, J = 5.6 Hz, 1H), 5.47-5.43 (m, 1H), 5.09-5.06 (m, 1H), 4.22-4.10 (m, 4H), 3.79-3.67 (m, 2H), 1.50 (d, J = 7.2 Hz, 3H). |

TABLE 3-continued

| Compound | R₁ | R₂ | LC-MS (M + H)⁺ | ¹HNMR (ppm) |
|---|---|---|---|---|
| V-10 | 4-phenylpyridin-2-yl | isopropyl | 426.1 | DMSO-d₆: δ 8.92 (s, 1H), 8.58 (d, J = 0.8 Hz, 1H), 8.46 (d, J = 5.2 Hz, 1H), 8.38 (d, J = 8.0 Hz, 1H), 8.02-7.97 (m, 1H), 7.84 (d, J = 7.2 Hz, 1H), 7.78-7.76 (m, 2H), 7.59-7.49 (m, 3H), 7.46-7.44 (m, 1H), 5.54-5.47 (m, 1H), 4.18 (s, 4H), 1.53 (d, J = 6.4 Hz, 6H). |
| V-11 | 4-morpholinophenyl | isopropyl | 434.2 | DMSO-d₆: δ 8.91 (s, 1H), 8.33 (d, J = 7.6 Hz, 1H), 8.00-7.90 (m, 1H), 7.81-7.74 (m, 1H), 7.54-7.47 (m, 2H), 7.03-6.94 (m, 2H), 5.57-5.46 (m, 1H), 4.19-4.07 (m, 2H), 4.02-3.91 (m, 2H), 3.82-3.68 (m, 4H), 3.16-3.00 (m, 4H), 1.52 (d, J = 6.8 Hz, 6H). |
| V-12 | 5-morpholinopyridin-2-yl | isopropyl | 435.4 | DMSO-d₆: δ 8.91 (s, 1H), 8.35-8.33 (m, 1H), 8.11-8.07 (m, 2H), 7.99-7.95 (m, 1H), 7.81-7.79 (m, 1H), 7.53-7.50 (m, 1H), 5.51-5.48 (m, 1H), 4.15-4.08 (m, 4H), 3.77-3.75 (m, 4H), 3.13-3.11 (m, 4H), 1.52 (d, J = 6.8 Hz, 6H). |
| V-13 | 5-((S)-3-methylmorpholino)pyridin-2-yl | isopropyl | 449.3 | CDCl₃: δ 8.43-8.37 (m, 2H), 8.22 (d, J = 9.0 Hz, 1H), 8.01-7.97 (m, 2H), 7.87-7.81 (m, 1H), 7.37-7.33 (m, 1H), 5.64-5.59 (m, 1H), 4.21-4.14 (m, 4H), 3.99-3.86 (m, 2H), 3.80-3.73 (m, 1H), 3.70-3.61 (m, 2H), 3.15-3.07 (m, 2H), 1.59 (d, J = 6.9 Hz, 6H), 1.05 (d, J = 6.3 Hz, 3H). |
| V-14 | 5-((S)-3-methylmorpholino)pyridin-2-yl | isopropyl | 449.3 | DMSO-d₆: δ 10.75 (s, 1H), 10.10 (s, 1H), 8.93 (s, 1H), 8.36 (d, J = 5.4 Hz, 1H), 8.07-7.95 (m, 2H), 7.78-7.75 (m, 1H), 7.56 (s, 1H), 7.04-7.02 (m, 1H), 5.76-5.64 (m, 1H), 4.49-4.39 (m, 1H), 4.36-4.22 (m, 1H), 3.65-3.51 (m, 2H), 3.26-3.16 (m, 2H), 2.17-1.89 (m, 2H), 1.68-1.37 (m, 9H), 1.34-1.20 (m, 2H), 1.18-1.07 (m, 6H), 0.82-0.77 (m, 3H). |
| V-15 | 5-(8-oxa-3-azabicyclo[3.2.1]octan-3-yl)pyridin-2-yl | isopropyl | 461.2 | DMSO-d₆: δ 8.91 (s, 1H), 8.36-8.33 (m, 1H), 8.06 (d, J = 9.2 Hz, 1H), 7.99-7.95 (m, 2H), 7.81-7.79 (m, 1H), 7.43-7.40 (m, 1H), 5.51-5.48 (m, 1H), 4.44 (s, 2H), 4.16-4.07 (m, 4H), 3.42-3.40 (m, 2H), 2.83-2.80 (m, 2H), 1.86 (s, 4H), 1.53 (d, J = 6.8 Hz, 6H). |

TABLE 3-continued

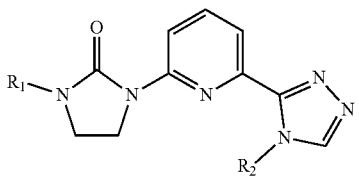

| Compound | R₁ | R₂ | LC-MS (M + H)⁺ | ¹HNMR (ppm) |
|---|---|---|---|---|
| V-16 |  | 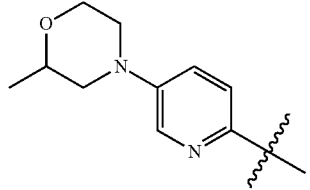 [SMILES: *c1ccc(N2CCOC(C)C2)cn1] | 463.2 | DMSO-d₆: δ 10.75 (s, 1H), 10.10 (s, 1H), 8.93 (s, 1H), 8.36 (d, J = 5.4 Hz, 1H), 8.07-7.95 (m, 2H), 7.78-7.75 (m, 1H), 7.56 (s, 1H), 7.04-7.02 (m, 1H), 5.76-5.64 (m, 1H), 4.49-4.39 (m, 1H), 4.36-4.22 (m, 1H), 3.65-3.51 (m, 2H), 3.26-3.16 (m, 2H), 2.17-1.89 (m, 2H), 1.68-1.37 (m, 9H), 1.34-1.20 (m, 2H), 1.18-1.07 (m, 6H), 0.82-0.77 (m, 3H). |
| V-17 |  | 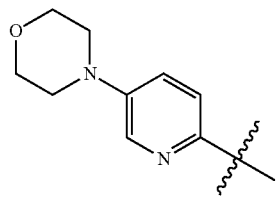 [SMILES: *c1ccc(N2CCOCC2)cn1] | 449.3 | DMSO-d₆: δ 8.91 (s, 1H), 8.34 (d, J = 7.2 Hz, 1H), 8.11-8.07 (m, 2H), 8.00-7.94 (m, 1H), 7.80 (d, J = 6.9 Hz, 1H), 7.54-7.49 (m, 1H), 5.51-5.47 (m, 1H), 4.13-4.08 (m, 4H), 3.95-3.90 (m, 1H), 3.69-3.57 (m, 3H), 3.50-3.45 (m, 1H), 2.72-2.58 (m, 1H), 2.40-2.24 (m, 1H), 1.50 (d, J = 6.9 Hz, 6H), 1.14 (d, J = 6.3 Hz, 3H). |
| V-18 |  | 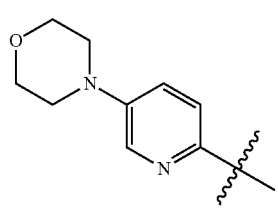 [SMILES: *c1ccc(N2CCOCC2)cn1] | 451.4 | CD₃OD-d₄: δ 8.82 (s, 1H), 8.46-8.43 (m, 1H), 8.17-8.14 (m, 1H), 8.02 (d, J = 2.7 Hz, 1H), 7.96-7.91 (m, 1H), 7.80-7.77 (m, 1H), 7.50-7.46 (m, 1H), 5.64-5.59 (m, 1H), 4.22-4.16 (m, 4H), 3.89-3.84 (m, 6H), 3.17-3.08 (m, 4H), 1.61 (d, J = 6.9 Hz, 3H). |
| V-19 | 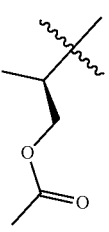 [SMILES: *[C@H](C)COC(C)=O] | 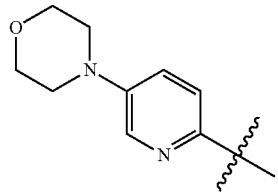 [SMILES: *c1ccc(N2CCOCC2)cn1] | 493.2 | DMSO-d₆: δ 8.93 (s, 1H), 8.35 (d, J = 7.6 Hz, 1H), 8.11-8.07 (m, 2H), 8.01-7.97 (m, 1H), 7.82 (d, J = 7.2 Hz, 1H), 7.54-7.51 (m, 1H), 5.82-5.76 (m, 1H), 4.39-4.35 (m, 2H), 4.10-4.00 (m, 4H), 3.77-3.75 (m, 4H), 3.13-3.09 (m, 4H), 1.86 (s, 3H), 1.57 (d, J = 7.2 Hz, 3H). |
| V-20 | 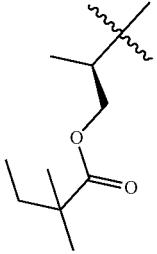 [SMILES: *[C@H](C)COC(=O)C(C)(C)CC] | 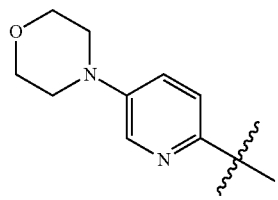 [SMILES: *c1ccc(N2CCOCC2)cn1] | 549.3 | DMSO-d₆: δ 10.08 (s, 1H), 10.01 (s, 1H), 9.14 (s, 1H), 8.94 (s, 1H), 8.20 (s, 1H), 8.07-7.88 (m, 4H), 7.77-7.68 (m, 2H), 7.53-7.48 (m, 1H), 5.83-5.76 (m, 1H), 4.39-4.31 (m, 2H), 1.64 (d, J = 6.9 Hz, 3H), 1.29-1.24 (m, 2H), 0.90 (s, 6H), 0.58-0.50 (m, 3H). |
| V-21 | 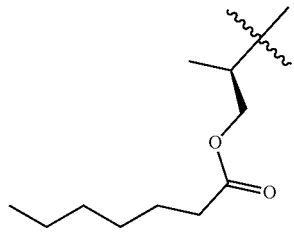 [SMILES: *[C@H](C)COC(=O)CCCCCC] |  | 563.3 | DMSO-d₆: δ 8.94 (s, 1H), 8.36 (d, J = 8.4 Hz, 1H), 8.11-8.07 (m, 2H), 8.00-7.96 (m, 1H), 7.83 (d, J = 7.6 Hz, 1H), 7.54-7.51 (m, 1H), 5.92-5.85 (m, 1H), 4.40-4.36 (m, 2H), 4.13-4.09 (m, 4H), 3.77-3.75 (m, 4H), 3.13-3.11 (m, 4H), 2.16-2.10 (m, 1H), 2.07-2.01 (m, 1H), 1.58 (d, J = 6.8 Hz, 3H), 1.31-1.10 (m, 8H), 0.82-0.78 (m, 3H). |

TABLE 3-continued
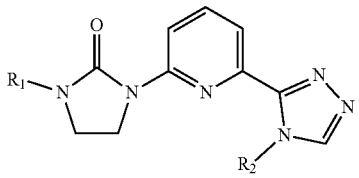
| Compound | R₁ | R₂ | LC-MS (M + H)⁺ | ¹HNMR (ppm) |
|---|---|---|---|---|
| V-22 | 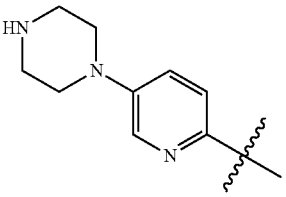 [SMILES: *c1ccc(N2CCNCC2)cn1] | 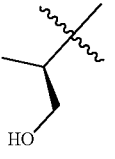 [SMILES: *[C@H](C)CO] | 450.2 | DMSO-d₆: δ 8.81 (s, 1H), 8.34-8.32 (m, 1H), 8.09-8.04 (m, 2H), 7.99-7.95 (m, 1H), 7.80-7.78 (m, 1H), 7.50-7.47 (m, 1H), 5.46-5.42 (m, 1H), 5.08-5.06 (m, 1H), 4.14-4.06 (m, 4H), 3.77-3.67 (m, 2H), 3.03-3.06 (m, 4H), 2.86-2.83 (m, 4H), 1.49 (d, J = 7.2 Hz, 3H). |
| V-23 | 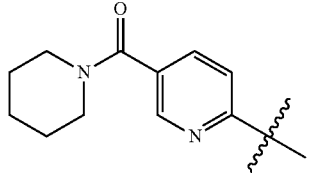 [SMILES: *c1ccc(C(=O)N2CCCCC2)cn1] | 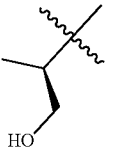 | 477.2 | DMSO-d₆: δ 8.82 (s, 1H), 8.43 (d, J = 1.6 Hz, 1H), 8.36-8.31 (m, 2H), 8.03-7.99 (m, 1H), 7.89-7.83 (m, 2H), 5.47-5.42 (m, 1H), 5.08-5.05 (m, 1H), 4.16 (s, 4H), 3.78-3.50 (m, 6H), 1.68-1.59 (m, 2H), 1.58-1.47 (m, 7H). |
| V-24 | 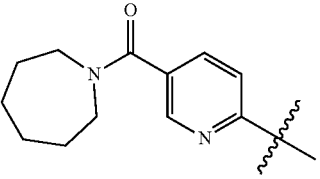 [SMILES: *c1ccc(C(=O)N2CCCCCC2)cn1] | 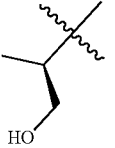 | 491.3 | DMSO-d₆: δ 8.82 (s, 1H), 8.43-8.42 (m, 1H), 8.37-8.30 (m, 2H), 8.04-7.99 (m, 1H), 7.90-7.83 (m, 2H), 5.47-5.41 (m, 1H), 5.08-5.05 (m, 1H), 4.16 (s, 4H), 3.78-3.67 (m, 2H), 3.59-3.55 (m, 2H), 3.40-3.33 (m, 2H), 1.78-1.70 (m, 2H), 1.57-1.49 (m, 9H). |
| V-25 | 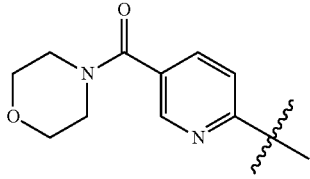 [SMILES: *c1ccc(C(=O)N2CCOCC2)cn1] | 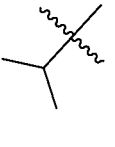 | 463.3 | DMSO-d₆: δ 8.92 (s, 1H), 8.48-8.46 (m, 1H), 8.37-8.32 (m, 2H), 8.03-7.99 (m, 1H), 7.93-7.90 (m, 1H), 7.85 (d, J = 7.6 Hz, 1H), 5.52-5.45 (m, 1H), 4.16 (s, 4H), 3.80-3.62 (m, 8H), 1.52 (d, J = 6.8 Hz, 6H). |
| V-26 | 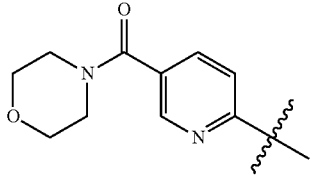 [SMILES: *c1ccc(C(=O)N2CCOCC2)cn1] | 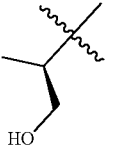 | 479.3 | DMSO-d₆: δ 8.81 (s, 1H), 8.48 (s, 1H), 8.41-8.29 (m, 2H), 8.08-7.98 (m, 1H), 7.96-7.81 (m, 2H), 5.52-5.40 (m, 1H), 5.12-5.03 (m, 1H), 4.16 (s, 4H), 3.82-3.45 (m, 10H), 1.50 (d, J = 6.6 Hz, 3H). |
| V-27 | 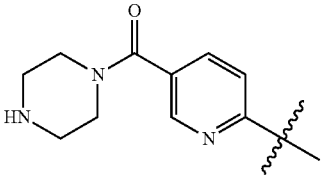 [SMILES: *c1ccc(C(=O)N2CCNCC2)cn1] | 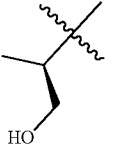 [SMILES: *[C@H](C)CO] | 478.2 | DMSO-d₆: δ 8.82 (s, 1H), 8.45 (d, J = 2.0 Hz, 1H), 8.36-8.32 (m, 2H), 8.18 (s, 1H), 8.03-7.96 (m, 1H), 7.91-7.84 (m, 2H), 5.46-5.42 (m, 1H), 4.16 (s, 4H), 3.78-3.67 (m, 3H), 2.89-2.73 (m, 4H), 1.50 (d, J = 7.2 Hz, 3H). |

Example 26: Synthesis of Compounds VI-01

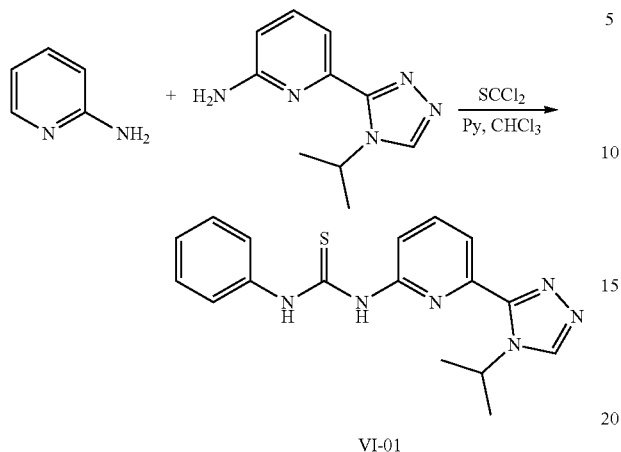

VI-01

1-(6-(4-Isopropyl-4H-1,2,4-triazol-3-yl)pyridin-2-yl)-3-(pyridin-2-yl)thiourea (Compound VI-01)

To a solution of pyridin-2-amine (190 mg, 2.0 mmol) in CHCl$_3$ (5 m) was added pyridine (320 mg, 4.0 mmol). Then a solution of SCCl$_2$ (230 mg, 2.0 mmol) in CHCl$_3$ (1 mL) was added dropwise to the mixture at −50° C. under N$_2$. The mixture was stirred at −50° C. for 16 h. Then a mixture of pyridine (320 mg, 4.0 mmol) and 6-[4-(propan-2-yl)-4H-1,2,4-triazol-3-yl]pyridin-2-amine (408 mg, 2.0 mmol) in CHCl$_3$ (3 mL) was added dropwise to the mixture at −50° C. The resulting mixture was stirred at −50° C. for another 2 h. The reaction mixture was diluted with H$_2$O and extracted with DCM. The resulted organic layer was washed with brine, dried over anhydrous sodium sulfate and filtered. The filtrate was concentrated under vacuum. The residue was purified by Prep-HPLC with the following conditions: Column: SunFire Prep C18 OBD Column 19×150 mm 5 um 10 nm; Mobile Phase A: Water (0.1% FA), Mobile Phase B: ACN; Flow rate: 25 mL/min; Gradient: 27% B to 44% B in 10 min; 254/220 nm to afford the title compound (21.0 mg, 3%) as a white solid. LCMS (ESI, m/z): [M+H]$^+$=340.1. $^1$HNMR (400 MHz, DMSO-d$_6$, ppm): δ 14.34 (s, 1H), 11.36 (s, 1H), 8.91 (s, 1H), 8.85 (s, 1H), 8.28-8.26 (m, 1H), 8.07-8.03 (m, 1H), 7.90-7.87 (m, 2H), 7.46 (s, 1H), 7.20-7.16 (m, 1H), 5.45-5.38 (m, 1H), 1.54 (d, J=6.8 Hz, 6H).

Example 27: Biological Activity of Compounds

Assay Protocol

Reagents: Recombinant human ASK1 kinase was from Invitrogen Inc. HTRF KinEASETM-STK S3 kit was obtained from Cisbio (Bedford, Mass.). All other reagents were of the highest grade commercially available.

Assay: The assay measures the phosphorylation level of a biotinylatd peptide substrate by the ASK1 kinase using HTRF detection. ASK1 kinase assay is based on HTRF KinEASETM-STK manual from Cisbio. Test compound, 1 uM STK-substrate-biotin, 3 nM of ASK1 kinase are incubated with 1*Kinase buffer with 5 mM MgCl2 and 1 mM DTT. 250 nM Sa-XL 665(4*) and STK-antibody-Cryptate work solution are added to stop the reaction and phosphorylated peptide substrate is detected using Envision 2104 Multilabeled reader from PerkinElmer. The fluorescence is measured at 615 nm (Cryptate) and 665 nm (XL665) and a ratio of 665 nm/615 nm is calculated for each well. The resulting TR-FRET level (a ratio of 665 nm/615 nm) is proportional to the phosphorylation level of substrate.

Biology Data

| Code | EC50 (nM) |
|---|---|
| I-001 | A |
| I-002 | A |
| I-003 | A |
| I-004 | A |
| I-005 | A |
| I-006 | A |
| I-007 | A |
| I-008 | A |
| I-009 | A |
| I-012 | B |
| I-013 | A |
| I-014 | A |
| I-015 | A |
| I-016 | B |
| I-017 | B |
| I-018 | B |
| I-020 | C |
| I-025 | A |
| I-026 | A |
| I-027 | B |
| I-028 | A |
| I-029 | A |
| I-030 | B |
| I-031 | B |
| I-032 | B |
| I-033 | B |
| I-034 | B |
| I-035 | A |
| I-036 | A |
| I-037 | B |
| I-038 | A |
| I-039 | A |
| I-040 | A |
| I-041 | B |
| I-042 | A |
| I-043 | A |
| I-044 | A |
| I-045 | A |
| I-046 | A |
| I-047 | A |
| I-048 | A |
| I-049 | A |
| I-050 | A |
| I-051 | A |
| I-052 | A |
| I-053 | A |
| I-054 | B |
| I-055 | A |
| I-056 | A |
| I-057 | A |
| I-058 | A |
| I-059 | A |
| I-061 | B |
| I-062 | A |
| I-065 | B |
| I-066 | A |
| I-067 | A |
| I-068 | A |
| I-069 | A |
| I-070 | A |
| I-071 | A |
| I-072 | A |
| I-073 | B |
| I-074 | A |
| I-075 | B |
| I-076 | A |
| I-077 | A |
| I-078 | A |
| I-079 | A |
| I-080 | A |

| Code | EC50 (nM) |
|---|---|
| I-081 | A |
| I-082 | A |
| I-083 | B |
| I-084 | A |
| I-085 | A |
| I-086 | A |
| I-087 | A |
| I-088 | A |
| I-089 | A |
| I-090 | A |
| I-091 | A |
| I-092 | A |
| I-093 | A |
| I-094 | A |
| I-095 | A |
| I-096 | A |
| I-097 | A |
| I-098 | A |
| I-099 | A |
| I-100 | A |
| I-101 | A |
| I-102 | A |
| I-103 | A |
| I-104 | A |
| I-105 | A |
| I-106 | A |
| I-107 | A |
| I-108 | A |
| I-109 | A |
| I-110 | A |
| I-115 | A |
| I-117 | A |
| I-118 | A |
| I-119 | A |
| I-120 | A |
| I-121 | A |
| I-122 | A |
| I-123 | A |
| I-124 | A |
| I-125 | A |
| I-126 | A |
| I-127 | A |
| I-128 | A |
| I-129 | A |
| I-130 | A |
| I-131 | A |
| I-132 | A |
| I-133 | A |
| I-134 | A |
| I-135 | A |
| I-136 | A |
| I-137 | A |
| I-138 | A |
| I-139 | A |
| I-140 | A |
| I-141 | A |
| I-142 | A |
| I-143 | A |
| I-144 | A |
| I-145 | A |
| I-146 | A |
| I-147 | A |
| I-148 | A |
| I-149 | A |
| I-150 | A |
| I-151 | A |
| I-152 | A |
| I-153 | A |
| I-154 | A |
| I-155 | A |
| I-156 | A |
| I-157 | A |
| I-158 | A |
| I-159 | A |
| I-160 | A |
| I-161 | A |
| I-162 | A |
| I-163 | A |
| I-164 | A |
| I-165 | A |
| I-166 | B |
| I-167 | A |
| I-168 | B |
| I-169 | A |
| I-170 | A |
| I-171 | B |
| I-172 | A |
| I-173 | A |
| I-174 | A |
| I-175 | A |
| I-176 | A |
| I-177 | A |
| I-178 | A |
| I-179 | A |
| I-180 | A |
| I-181 | A |
| I-182 | A |
| I-183 | A |
| I-184 | A |
| I-185 | A |
| I-186 | A |
| I-187 | A |
| I-188 | A |
| I-189 | A |
| I-190 | A |
| I-191 | A |
| I-192 | A |
| I-193 | A |
| I-194 | A |
| I-195 | A |
| I-196 | A |
| I-198 | A |
| I-199 | A |
| I-200 | A |
| I-201 | B |
| I-202 | A |
| I-203 | A |
| I-204 | A |
| I-205 | A |
| I-206 | A |
| I-207 | A |
| I-208 | A |
| I-209 | A |
| I-210 | A |
| I-211 | A |
| I-212 | A |
| I-213 | A |
| I-214 | A |
| I-215 | A |
| I-216 | A |
| I-217 | A |
| I-218 | A |
| II-01 | C |
| III-01 | B |
| III-02 | A |
| III-03 | A |
| III-04 | A |
| III-05 | A |
| III-06 | A |
| III-07 | A |
| III-08 | B |
| III-10 | A |
| V-01 | A |
| V-02 | A |
| V-03 | A |
| V-04 | A |
| V-05 | A |
| V-06 | A |
| V-07 | A |
| V-08 | A |
| V-11 | A |
| V-12 | A |
| V-14 | A |
| V-15 | A |

| Code | EC50 (nM) |
|---|---|
| V-16 | A |
| V-17 | A |
| V-18 | A |
| V-19 | B |
| V-22 | A |
| V-23 | A |
| V-25 | A |
| V-26 | A |
| V-27 | A |
| VI-01 | B |

A: $EC_{50} \leq 50$ nM;
B: 50 nM $< EC_{50} \leq 500$ nM;
C: 500 nM $< EC_{50} \leq 5000$ nM

EQUIVALENTS

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A compound of Formula IC:

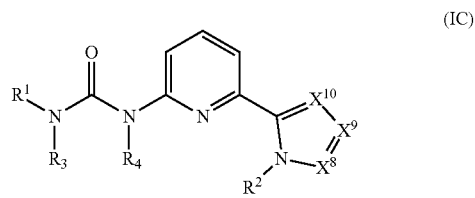

(IC)

wherein
 $X^8$, $X^9$, and $X^{10}$ are independently CH or N;
 $R^1$ is a substituted or unsubstituted aryl or heteroaryl group;
 $R^2$ is substituted or unsubstituted alkyl or cycloalkyl group; and
 $R^3$ and $R^4$ are independently H or a substituted or unsubstituted alkyl or cycloalkyl group, or $R^3$ and $R^4$ together are a $C_2$-$C_3$ alkylene or alkenylene group or a phenylene group;
 or a pharmaceutically acceptable salt thereof.

2. The compound of claim 1 wherein $X^8$ is CH.

3. The compound of claim 1 wherein $X^9$ is N.

4. The compound of claim 1 wherein $X^{10}$ is N.

5. The compound of claim 1 having the Formula ID:

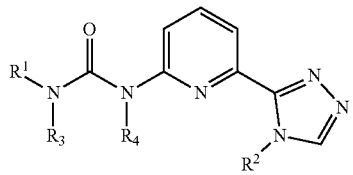
(ID)

or a pharmaceutically acceptable salt thereof.

6. The compound of claim 1 wherein the compound is a compound of Formula IE, IF, or IG:

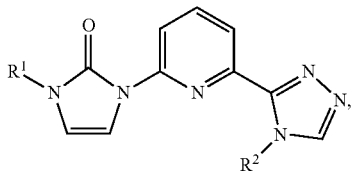
(IE)

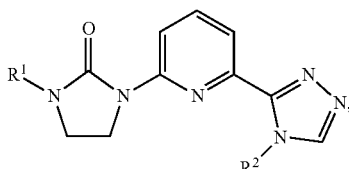
(IF)

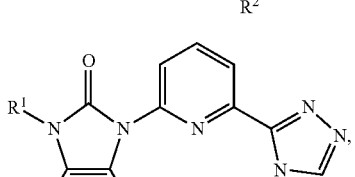
(IG)

or a pharmaceutically acceptable salt thereof.

7. The compound of claim 1 wherein $R^1$ is a substituted or unsubstituted phenyl, pyridinyl, pyrazinyl, pyrimidinyl, isoquinolinyl, quinolinyl, oxazolyl, benzoxazolyl, or benzthiazolyl group.

8. The compound of claim 7 wherein $R^1$ is substituted with one or more substituents selected from the group consisting of F, Cl, Br, I, OH, CN, COOH, C(O)O(unsubstituted alkyl), C(O)O(aralkyl), C(O)O(alkenyl), C(O)NH(cycloalkyl), C(O)NH(aryl), C(O)NH(pyridinyl), C(O)(aryl), C(O)(unsubstituted alkyl), C(O)(arlkyl), C(O)(alkenyl), C(O)(piperidinyl), C(O)(morpholinyl), C(O)(piperazinyl), C(O)(pyrrolidinyl), C(O)(azepanyl), C(O)(quinolyl), C(O)(tetrahydroquinolinyl), C(O)(decahydroquinolinyl), C(O)(isoquinolinyl), C(O)(tetrahydroisoquinolinyl), C(O)(3-azaspiro[5,5]-undecanyl), C(O)(8-azabicyclo[3.2.1]octanyl), $NH_2$, $NO_2$, $C(O)NH_2$, NH(alkyl), N(alkyl)$_2$, $SO_2$(alkyl), $SO_2$NH(phenyl), $SO_2NH_2$, $NHSO_2$(aryl), $SO_2$(piperidinyl), $SO_2$(morpholinyl), alkyl, thioalkyl, haloalkyl, alkoxy, aralkoxy, aralkylthio, haloalkoxy, hydroxyalkyl, cycloalkyl, phenyl, pyrrolidinyl, morpholinyl, 3-oxa-8-azabicyclo[3.2.1]octanyl, piperidinyl, piperazinyl, imidazolyl, triazolyl, tetrahydropyran, and pyridinyl, wherein the alkyl groups are unsubstituted except as indicated, and wherein the phenyl, pyridinyl, piperidinyl, piperazinyl, imidazolyl, triazolyl, and morpholinyl substituents are themselves optionally substituted with one or more secondary substituents selected from halo, OH, oxo, unsubstituted alkyl, hydroxyalkyl, cycloalkyl, phenyl, $SO_2$(alkyl), C(O)(alkyl), and morpholinyl.

9. The compound of claim 1 wherein $R^2$ is $C_1$-$C_6$ akyl, $C_3$-$C_6$ cycloalkyl or $C_4$-$C_8$ cycloalkylalkyl group optionally substituted with one or more groups selected from the group consisting of halo, OH, $NH_2$, $OCH_3$, $OP(O)(OH)_2$, OC(O)(substituted or unsubstituted alkyl), and OP(O)(OPh)NHC(unsubstituted alkyl)C(O)(unsubstituted alkyl).

10. A composition comprising a compound of claim 1 and a pharmaceutically acceptable carrier.

11. A pharmaceutical composition comprising an effective amount of the compound of claim 1 for treating an ASK1-mediated disorder or condition.

12. The pharmaceutical composition of claim 11 wherein the disorder or condition is selected from the group consisting of fibrotic diseases, acute and chronic liver diseases, kidney diseases, autoimmune disorders, inflammatory diseases, cardiovascular diseases, diabetes, diabetic nephropathy, cardio-renal diseases, and neurodegenerative diseases.

13. The pharmaceutical composition of claim 12 wherein the disorder or condition is a selected from the group consisting of liver fibrosis, lung fibrosis, kidney fibrosis, idiopathic pulmonary fibrosis (IPF), and non-alcoholic steatohepatitis (NASH).

14. The pharmaceutical composition of claim 12 wherein the disorder or condition is liver fibrosis or NASH.

15. A method of treating a disease or disorder comprising administering an effective amount of a compound of claim 1 or an effective amount of a composition of claim 10 to a subject suffering from the disease or disorder mediated by ASK1.

16. The method of claim 15, wherein the disorder or condition is selected from the group consisting of fibrotic diseases, acute and chronic liver diseases, kidney diseases, autoimmune disorders, inflammatory diseases, cardiovascular diseases, diabetes, diabetic nephropathy, cardio-renal diseases, and neurodegenerative diseases.

17. The method of claim 16, wherein the disorder or condition is liver fibrosis, lung fibrosis, kidney fibrosis, idiopathic pulmonary fibrosis (IPF), and non-alcoholic steatohepatitis (NASH).

18. A method comprising inhibiting ASK1 by contacting ASK1 with an effective amount of a compound of claim 1.

* * * * *